(12) United States Patent
Sprecher et al.

(10) Patent No.: US 7,682,787 B2
(45) Date of Patent: Mar. 23, 2010

(54) COMPOSITIONS AND METHODS FOR TREATING DISORDERS ASSOCIATED WITH ABNORMAL PHOSPHATE METABOLISM

(75) Inventors: Eli Sprecher, Kiryat Tivon (IL); Reuven Bergman, Haifa (IL)

(73) Assignee: Technion Research & Development Foundation Ltd., Haifa (IL)

( * ) Notice: Subject to any disclaimer, the term of this patent is extended or adjusted under 35 U.S.C. 154(b) by 278 days.

(21) Appl. No.: 10/870,030

(22) Filed: Jun. 18, 2004

(65) Prior Publication Data

US 2005/0249718 A1 Nov. 10, 2005

(30) Foreign Application Priority Data

May 9, 2004 (IL) ..................................... 161886

(51) Int. Cl.
*C12Q 1/68* (2006.01)
*C12P 19/34* (2006.01)
*C07H 21/02* (2006.01)
*C07H 21/04* (2006.01)

(52) U.S. Cl. .......................... 435/6; 435/91.1; 435/91.2; 536/23.1

(58) Field of Classification Search ........................ None
See application file for complete search history.

(56) References Cited

U.S. PATENT DOCUMENTS

2003/0181379 A1 9/2003 Econs et al.

OTHER PUBLICATIONS

Topaz et al; Nature Genetics, vol. 36, pp. 579-581, May 9, 2004.*
Campagnoli et al; Journal of Clinical Pathology, vol. 59, pp. 440-442, 2006.*
Frishberg et al; J. Mol. Med. vol. 83, pp. 33-38; 2005.*
Introduction to Genetic Analysis, 3rd Edition, Eds: Suzuki D, Griffiths JF, Miller JH, Lewontin Rc, 1986 p. 582.*
Garringer et al; J. Clin. Endo&Metabolism, vol 91, pp. 4037-4042, 2006.*
Barbieri et al; J Hum Genet. vol. 52, pp. 464-468, 2007.*
??? "SMART™ PCR cDNA Synthesis Kit / SMART™ cDNA Library Construction Kit", Clontech, p. 50, 2000.
White et al. "Molecular Cloning of A Novel Human UDP-GalNAc: Polypeptide N-Acetylgalactosaminyltransferase, GalNAc-T8, and Analysis as A Candidate Autosomal Dominant Hypophosphatemic Rickets (ADHR) Gene", Gene, 246(1-2): 347-356, 2000.
Topaz et al. "Mutations in GALNT3, Encoding A Protein Involved in O-Linked Glycosylation, Cause Familial Tumoral Calcinosis", Nature Genetics, 36(6): 579-581, 2004.
Frishberg et al. "Identification of A Recurrent Mutation in GALNT3 Demonstrates That Hyperostosis-Hyperphosphatemia Syndrome and Familial Tumoral Calcinosis Are Allelic Disorders", Journal of Molecular Medicine, 83(3): 240, 2005. Erratum.
Dosaka-Akita et al. "N-Acetylgalactosaminyl Transferase-3 Is A Potential New Marker for Non-Small Cell Lung Cancers", British Journal of Cancer, 87: 751-755, 2002. Materials and Methods.
Nomoto et al. "Structural Basis for the Regulation pf UDP-N-Acetyl-α-D-Galactosamine: Polypeptide N-Acetylgalactosaminyl Transferase-3 Gene Expression in Adenocarcinoma Cells", Cancer Research, 59(24): 6214-6222, 1999. Abstract.
Kristiansen et al. "IDDM7 Links to Insulin-Dependent Diabetes Mellitus in Danish Multiplex Families But Linkage Is Not Explained by Novel Polymorphisms in the Candidate Gene GALNT3. The Danish Study Group of Diabetes in Childhood and the Danish IDDM Epidemiology and Genetics Group", Human Mutation, 15(3): 295-296, 2000. Abstract.
Bowe et al. "FGF-23 Inhibits Renal Tubular Phosphate Transport and Is A PHEX Substrate", Biochemical and Biophysical Research Communicatons, 284: 977-981, 2001.
Chertow "Slowing the Progress of Vascular Calcification in Hemodialysis", Journal of the American Society of Nephrology, 14: S310-S314, 2003.
Hutchison "Improving Phosphate-Binder Therapy as A Way Forward", Nephrology, Dialysis, Transplantation, 19(Suppl.1): i19-i24, 2004.
Jan De Beur et al. "Molecular Pathogenesis of Hypophosphatemic Rickets", The Journal of Clinical Endocrinology & Metabolism, 87(6): 2467-2473, 2002.
Joy et al. "Randomized, Double-Blind, Placebo-Controlled, Dose-Titration, Phase III Study Assessing the Efficacy and Tolerability of Lanthanum Carbonate: A New Phosphate Binder for the Treatment of Hyperphosphatemia", American Journal of Kidney Diseases, 42(1): 96-107, 2003.
Quarles "FGF23, PHEX, and MEPE Regulation of Phosphate Homeostasis and Skeletal Mineralization", American Journal of Physiology, Endocrinology & Metabolism, 285: E1-E9, 2003.
Schiavi et al. "The Phosphatonin Pathway: New Insights in Phosphate Homeostasis", Kidney International, 65: 1-14, 2004.
Shimada et al. "Cloning and Characterization of FGF23 as A Causative Factor of Tumor-Induced Osteomalacia", Proc. Natl. Acad. Sci. USA, 98(11):6500-6505, 2001.
Ten Hagen et al. "All in the Family: The UDP-GalNAc:Polypeptide N-Acetylgalactosaminyltransferases", Glycobiology, 13(1): 1R-16R, 2003.
Berndt et al. "Secreted Frizzled-Related Protein 4 Is A Potent Tumor-Derived Phosphaturic Agent", Journal of Clinical Investigation, 112(5): 785-794, Sep. 2003.
Quarles "Evidence for A Bone-Kidney Axis Regulating Phosphate Homeostasis", The Journal of Clinical Investigation, 112(5): 642-646, Sep. 2003.
Communication Pursuant to Article 94(3) EPC Dated Jun. 17, 2008 From the European Patent Office Re.: Application No. 05740635.7.
Communication Pursuant to Article 96(2) EPC Dated Jul. 24, 2007 From the European Patent Office Re.: Application No. 05740635.7.
International Preliminary Report on Patentability Dated Nov. 23, 2008 From the International Bureau of WIPO Re.: Application No. PCT/IL2005/000484.
International Search Report Dated Aug. 31, 2005 From the International Searching Authority Re.: Application No. PCT/IL2005/000484.
Written Opinion Dated Aug. 31, 2005 From the International Searching Authority Re.: Application No. PCT/IL2005/000484.
Communication Pursuant to Article 94(3) EPC Dated Jan. 9, 2009 From the European Patent Office Re.: Application No. 05740635.7.

* cited by examiner

*Primary Examiner*—Jehanne S Sitton

(57) ABSTRACT

The present invention uncovers that mutations in GALNT3 gene encoding UDP-N-acetyl-alpha-D-galactosamine: polypeptide N-acetylgalactosaminyltransferase (GalNAc-T3) cause familial tumoral calcinosis (FTC). Methods and pharmaceutical compositions useful for treating disorders associated with abnormal phosphate metabolism are provided. Specifically, inducers of GalNAc-T3 can be used to treat hyperphosphatemia related disorders such as FTC, and on the other hand, inhibitors of GalNAc-T3 can be used to treat disorders associated with hypophosphatemia, such as hypophosphatemic rickets.

6 Claims, 8 Drawing Sheets

(4 of 8 Drawing Sheet(s) Filed in Color)

COMPOSITIONS AND METHODS FOR TREATING DISORDERS ASSOCIATED WITH ABNORMAL PHOSPHATE METABOLISM

This application claims the benefit of priority from Israel Patent Application No. 161886, filed on May 9, 2004.

FIELD AND BACKGROUND OF THE INVENTION

The present invention relates to methods of treating disorders associated with abnormal phosphate metabolism, and more particularly to the use of regulators of GalNAc-T3 in the treatment of disorders associated with hyperphosphatemia such as Familial tumoral calcinosis (FTC), hyperphosphatemic calcinosis, hemodialysis, and chronic renal failure, as well as disorders associated with hypophosphatemia, e.g., X-linked vitamin D resistant hypophosphatemic rickets (HYP), hereditary hypercalciuria with hypophosphatemic rickets (HHRH), oncogenic hypophosphatemic osteomalacia (OHO), and X-linked hypophosphatemic rickets (PHEX).

Phosphate-related abnormalities (i.e., hypophosphatemia or hyperphosphatemia) characterize a class of metabolic disorders manifesting with hyper-and dys-lipidemia, rickets and/or serious metastatic calcification, which can eventually lead to death. These disorders result from disrupted phosphate metabolism. Inorganic phosphate is absorbed in the intestinal tract in a process regulated by 1α, 25-dihydroxyvitamin D3 (vitamin D3). On the other hand, phosphate excretion, which is regulated by the parathyroid hormone, takes place in both kidney and intestinal tract (i.e., fecal excretion). Moreover, the liver, skin and kidney are involved in the conversion of vitamin D3 to its active metabolite, calcitriol, which plays an active role in maintaining phosphate balance and bone mineralization.

Under normal conditions, a decrease in plasma phosphate level stimulates the production of vitamin D3 in the renal proximal tubule, resulting in increased absorption of calcium and phosphate. The increase in calcium level leads to a secondary suppression of the parathyroid hormone (PTH), which results in upregulation of the sodium-dependent phosphate transport in the renal proximal tubule.

Hyperparathyroidism, a condition characterized by overproduction of PTH in the parathyroid glands, results in hypophosphatemia and increased phosphate excretion due to inhibition of sodium-dependent phosphate transport in the kidney.

Other conditions which involve hypophosphatemia include vitamin D deficiency, which causes rickets in children and osteomalacia in adults, X-linked vitamin D resistant hypophosphatemic rickets (HYP), hereditary hypercalciuria with hypophosphatemic rickets (HHRH), Dent's disease including certain types of renal Fanconi syndrome, renal I alpha-hydroxylase deficiency (VDDR 1), defects in 1,25-dihydroxy vitamin D3 receptor (end organ resistance, VDDR II), oncogenic hypophosphatemic osteomalacia (OHO), and X-linked hypophosphatemic rickets (PHEX) [Francis, Nat. Genet. (1995), 11: 130-136; Rowe, Hum. Genet. (1996), 97: 345-352; Rowe, Hum. Mol. Genet. (1997), 6: 539-549).

On the other hand, hyperphosphatemia, i.e., increased plasma level of $PO_4$, is often a result of renal insufficiency. End-stage renal insufficiency, a condition affecting approximately 250,000 individuals in the USA, can lead to metastatic calcification, i.e., the deposition of calcium phosphate in previously healthy connective tissues and solid organs. Thus, advanced renal failure, i.e., a glomerular filtration rate of less than 20 mL/min, causes a decrease in $PO_4$ excretion and an increase of plasma $PO_4$. However, other conditions may also decrease $PO_4$ excretion. These include pseudohypoparathyroidism or hypoparathyroidism. Hyperphosphatemia can also result from excess administration of oral $PO_4$, or from overuse of enema containing phosphate salts. Furthermore, hyperphosphatemia may result from migration of intracellular $PO_4$ to the cell exterior. Such migration frequently occurs in diabetic ketoacidosis (regardless of systemic $PO_4$ loss), bruise, non-traumatic rhabdomyolysis, systemic infection and tumor lysis syndrome. Moreover, hyperphosphatemia plays a critical role in the onset of secondary hyperparathyroidism, and the onset of renal osteodystrophy in patients under dialysis treatment for a long period.

Familial tumoral calcinosis (FTC; MIM211900) is a severe autosomal recessive metabolic disorder manifesting with hyperphosphatemia and massive calcium deposits in the skin and subcutaneous tissues, especially of the hips and knees. Hyperphosphatemia, secondary to increased renal phosphate retention, is the major metabolic abnormality associated with familial tumoral calcinosis (FTC) and is accompanied by inappropriately normal or elevated levels of PTH and 1,25-dihydroxyvitamin D3, two essential regulators of phosphate metabolism [Steinherz, 1985 (Supra)]. While hyperphosphatemia appears in FTC patients as early as 21 months of age, the calcium deposits are noted later in childhood. Thus, all FTC patients have elevated serum phosphorus levels, and in some patients, elevated levels of 1,25-vitamin D are also detected. FTC represents the metabolic mirror image of hypophosphatemic rickets caused by mutations in PHEX (MIM307800) and in FGF23 (MIM193100) genes [Schiavi, S. C. and Kumar, R. Kidney Int. 65, 1-14 (2004); Quarles, L. D. Am. J. Physiol. Endocrinol. Metab. 285, 1-9 (2003)] and which is characterized by decreased phosphate levels, decreased renal tubular phosphate reabsorption and inappropriately normal or decreased levels of 1,25-dihydroxyvitamin D3 [Prince M. J. et al. Ann Intern Med. 96, 586-591 (1982)].

Current treatment regimens of hypophosphatemia related disorders [e.g., hypophosphatemic rickets (PHEX)] include active vitamin D analogues (e.g., calcitriol) and oral phosphate supplementation. However, both of these nutrition supplements often fail to normalize serum phosphate level and in many cases, the patients fail to reach normal adult height. The recent use of recombinant human growth hormone (rhGH) was reported to benefit children with PHEX, however, is often associated with disproportional growth of the trunk (Reviewed in Reusz G, 2001, Orv Hetil. 142: 2659-65; Wilson D M 2000, J. Pediatr. Endocrinol. Metab. Suppl 2: 993-8).

Treatment of hyperphosphatemia involves the use of aluminum- or calcium-based phosphate-binding agents, which effectively lower serum phosphorus levels. However, while the use of aluminum-based agents can be associated with bone toxicity, renal osteodystrophy and encephalopathy, the use of calcium-based agents is often associated with hypercalcaemia and cardiovascular calcification. To overcome these limitations, non-calcium-, non-aluminium-based alternative agents were developed. These include the sevelamer hydrochloride and lanthanum carbonate (Hutchison A J, 2004, Nephrol Dial Transplant. 19 Suppl 1:i19-24; Chertow G M., 2003, J Am Soc Nephrol. 14: S310-4). However, while lanthanum was found to be effective and well-tolerated (Joy M S et al., 2003, Am. J. Kidney Dis. 42: 96-107), sevelamer was found to be less effective than aluminum (Cizman B. 2003, Nephrol. Dial. Transplant. 18 Suppl 5:v47-9) and the use of both of these agents is limited by their high cost. Moreover, both of these agents treat only the symptoms by suppressing phosphate re-absorption in the intestinal track and not the causes which lead to hyperphosphatemia.

Thus, there is a need to develop pharmaceutical compositions and methods of treating disorders associated with phosphate metabolism devoid of the above limitations.

Phosphatonin is a novel circulating phosphaturic factor, postulated to be primarily responsible for modulating urinary phosphate excretion in a variety of hypophosphatemic disorders.

Quarles, 2003 (J Clin Invest. 112: 642-646), suggested that phosphatonin is a circulating protein that inhibits sodium-dependent phosphate reabsorption in the renal proximal tubule via mechanisms which are distinct from PTH, and vitamin D3. The fibroblast growth factor 23 (FGF23), secreted frizzled-related protein 4 (SFRP4) and matrix extracellular phosphoglycoprotein (MEPE) [Schiavi, S. C. and Kumar, R. Kidney Int. 65, 1-14 (2004); Quarles, L. D. Am. J. Physiol. Endocrinol. Metab. 285, 1-9 (2003)] were suggested as the putative phosphatonin proteins since they modulate circulating phosphate levels [Shimada, T. et al. Proc Natl Acad. Sci. 98, 6500-6505 (2001); Bowe A. E. et al. Bioch Biophys Res Comm. 284, 977-981 (2001); Rowe P. S. N. et al. Bone. 34, 303-319 (2003); Berndt, T. et al. J. Clin. Invest. 112, 785-794 (2003)].

Thus, FGF23 and other phosphatonin genes have been considered as prime candidates for the FTC gene [Jan De Beur, S. M., and Levine, M. A. (2002), J. Clin. Endocrinol. Metab. 87: 2467-2473].

While reducing the present invention to practice, the present inventors have uncovered that mutations in GALNT3 gene encoding UDP-N-acetyl-alpha-D-galactosamine: polypeptide N-acetylgalactosaminyltransferase (GalNAc-T3) cause FTC. Thus, inducers of GalNAc-T3 can be used to treat hyperphosphatemia related disorders such as FTC, and on the other hand, inhibitors of GalNAc-T3 can be used to treat disorders associated with hypophosphatemia, such as hypophosphatemic rickets.

SUMMARY OF THE INVENTION

According to one aspect of the present invention there is provided a method of treating a disorder associated with abnormal phosphate metabolism comprising providing to an individual in need thereof an agent capable of regulating an expression level and/or activity of GalNAc-T3 thereby treating the disorder associated with abnormal phosphate metabolism in the individual.

According to another aspect of the present invention there is provided a method of diagnosing familial tumoral calcinosis in an individual, the method comprising identifying in a polynucleotide sequence derived from the individual at least one nucleic acid substitution resulting in downregulation of an expression level and/or activity of GalNAc-T3, thereby diagnosing familial tumoral calcinosis in the individual.

According to yet another aspect of the present invention there is provided a method of identifying an agent suitable for treating a disorder associated with abnormal phosphate metabolism, comprising exposing GalNAc-T3 or cells expressing GalNAc-T3 to a plurality of molecules and selecting from the plurality of molecules at least one molecule capable of regulating the expression level and/or the activity of the GalNAc-T3, the at least one molecule being the agent suitable for treating the disorder associated with abnormal phosphate metabolism.

According to further features in preferred embodiments of the invention described below, the disorder is associated with hyperphosphatemia.

According to still further features in the described preferred embodiments the disorder associated with the hyperphosphatemia is selected from the group consisting of Familial tumoral calcinosis (FTC), hyperphosphatemic calcinosis, hemodialysis, and chronic renal failure.

According to still further features in the described preferred embodiments regulating is upregulating the expression level and/or activity of the GalNAc-T3.

According to still further features in the described preferred embodiments upregulating is effected by at least one approach selected from the group consisting of:

(a) expressing in cells of the individual an exogenous polynucleotide encoding at least a functional portion of GALNT3;

(b) increasing expression of endogenous GalNAc-T3 in the individual;

(c) increasing endogenous GalNAc-T3 activity in the individual;

(d) introducing an exogenous polypeptide including at least a functional portion of GalNAc-T3 to the individual;

(e) introducing at least one GalNAc-T3 substrate to the individual; and (f) administering GalNAc-T3-expressing cells into the individual.

According to still further features in the described preferred embodiments the exogenous polynucleotide encoding at least a functional portion of GALNT3 is set forth in SEQ ID NO:29.

According to still further features in the described preferred embodiments the GalNAc-T3 is set forth in SEQ ID NO:28.

According to still further features in the described preferred embodiments the disorder is associated with hypophosphatemia.

According to still further features in the described preferred embodiments the disorder associated with the hypophosphatemia is selected from the group consisting of X-linked vitamin D resistant hypophosphatemic rickets (HYP), hereditary hypercalciuria with hypophosphatemic rickets (HHRH), oncogenic hypophosphatemic osteomalacia (OHO), and X-linked hypophosphatemic rickets (PHEX).

According to still further features in the described preferred embodiments regulating is downregulating the expression level and/or the activity of the GalNAc-T3.

According to still further features in the described preferred embodiments downregulating is effected by introducing into the individual an agent selected from the group consisting of:

(a) a molecule which binds the GalNAc-T3;

(b) an enzyme which cleaves the GalNAc-T3;

(c) an antisense polynucleotide capable of specifically hybridizing with at least part of an mRNA transcript encoding GALNT3;

(d) a ribozyme which specifically cleaves at least part of an mRNA transcript encoding GALNT3;

(e) a small interfering RNA (siRNA) molecule which specifically cleaves at least part of a transcript encoding GALNT3;

(f) a non-functional analogue of at least a catalytic or binding portion of the GalNAc-T3;

(g) a molecule which prevents GalNAc-T3 activation or substrate binding.

According to still further features in the described preferred embodiments the mRNA transcript encoding GALNT3 is set forth in SEQ ID NO:29.

According to still further features in the described preferred embodiments introducing is effected via systemic administration of the agent.

According to still further features in the described preferred embodiments the polynucleotide sequence is an mRNA sequence encoding GALNT3 or a genomic sequence region including the GALNT3 gene.

According to still further features in the described preferred embodiments the polynucleotide sequence is set forth by SEQ ID NO:29 or 33.

According to still further features in the described preferred embodiments identifying at least one nucleic acid substitution in the GALNT3 gene is effected using a method selected from the group consisting of DNA sequencing, restriction fragment length polymorphism (RFLP analysis), allele specific oligonucleotide (ASO) analysis, Denaturing/Temperature Gradient Gel Electrophoresis (DGGE/TGGE), Single-Strand Conformation Polymorphism (SSCP) analysis, Dideoxy fingerprinting (ddF), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, MassEXTEND, MassArray, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Rolling circle amplification, and Invader assay.

According to still further features in the described preferred embodiments identifying the at least one nucleic acid substitution in the mRNA sequence encoding the GALNT3 is effected using DNA sequencing of a GLANT3 RT-PCR product.

According to still further features in the described preferred embodiments identifying the at least one amino acid substitution is effected using an antibody capable of differentially binding to at least one polymorph of the GalNAc-T3, the at least one polymorph includes the amino acid substitution capable of downregulating the expression level and/or the activity of GalNAc-T3.

According to still further features in the described preferred embodiments the GalNAc-T3 includes at least a catalytic or binding portion of the GalNAc-T3.

According to still further features in the described preferred embodiments the cells expressing GalNAc-T3 are selected from the group consisting of kidney cells, fibroblasts, epithelial cells, lymphocytes, bone marrow cells, lung cells, liver cells and brain cells.

According to still further features in the described preferred embodiments the expression level is detected using an immunological detection method and/or an RNA detection method.

According to still further features in the described preferred embodiments the immunological detection method is selected from the group consisting of a radio-immunoassay (RIA), an enzyme linked immunosorbent assay (ELISA), a western blot, an immunohistochemical analysis, and a fluorescence activated cell sorting (FACS).

According to still further features in the described preferred embodiments the RNA detection method is selected from the group consisting of Northern Blot, RT-PCR, RNA in situ hybridization, and in situ RT-PCR.

According to still further features in the described preferred embodiments the activity is determined using an activity assay selected from the group consisting of in situ activity assay and in vitro activity assays.

According to still further features in the described preferred embodiments the activity assay is effected using a substrate selected from the group consisting of $HIV_{H1B}gp120$, Fibronectin, Prion-a, CD59, Muc1a, Muc2, EA2, Muc7.

The present invention successfully addresses the shortcomings of the presently known configurations by providing methods of treating disorders associate with abnormal phosphate metabolism.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1B:
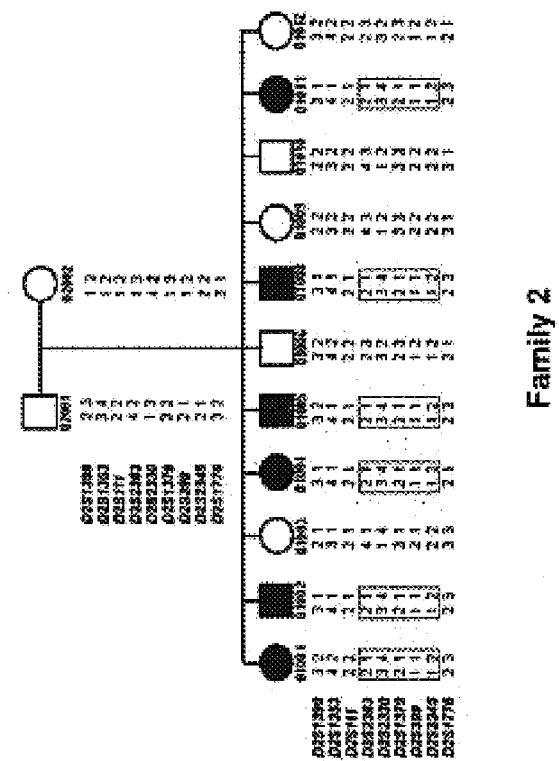
Figure 1A:
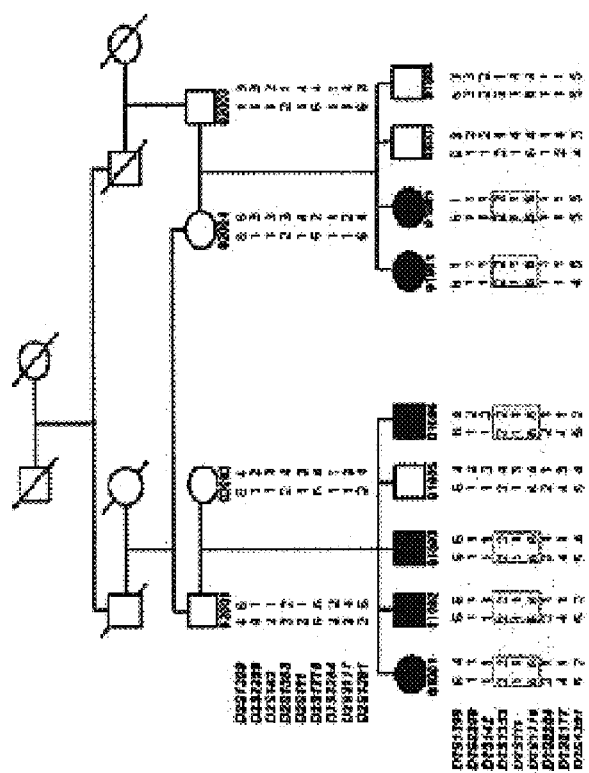

FIGS. 1a-b are diagrams illustrating mapping of the familial tumoral calcinosis (FTC) critical region. Shown are haplotype analyses of a consanguinity FTC family (Family 1, FIG. 1a) and a non-consanguinity FTC family (Family 2, FIG. 1b) using polymorphic microsatellite markers on chromosome 2q24-q31.1. The shared disease-associated haplotypes of all participating individuals are indicated by boxes. The noted DNA markers correspond to the following GenBank Accession numbers: G08198 (D2S1399), G07884 (D2S1353); Z16431 (D2S111), Z54008 (D2S2330), G08153 (D2S1379), Z24635 (D2S399), Z50933 (D2S2345), G08180 (D2S1776), Z53666 (D2S2299), Z16821 (D2S142), Z53511 (D2S2284), Z52323 (D2S2177), and G08168 (D2S1391).

Figure 2B:
Figure 2A:
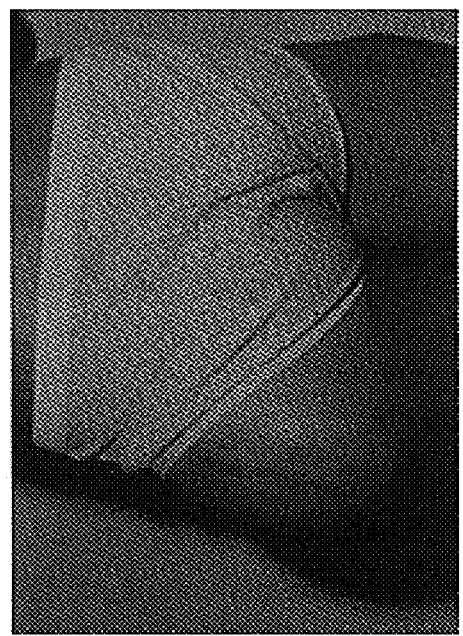

FIGS. 2a-b are photographs illustrating the clinical features of FTC. FIG. 2a—a large subcutaneous tumor over the left outer thigh of patient No. 01001 of family 1. FIG. 2b—a periarticular calcified mass over the left acetabulum of patient No. 01006 of family 1.

Figure 3B:
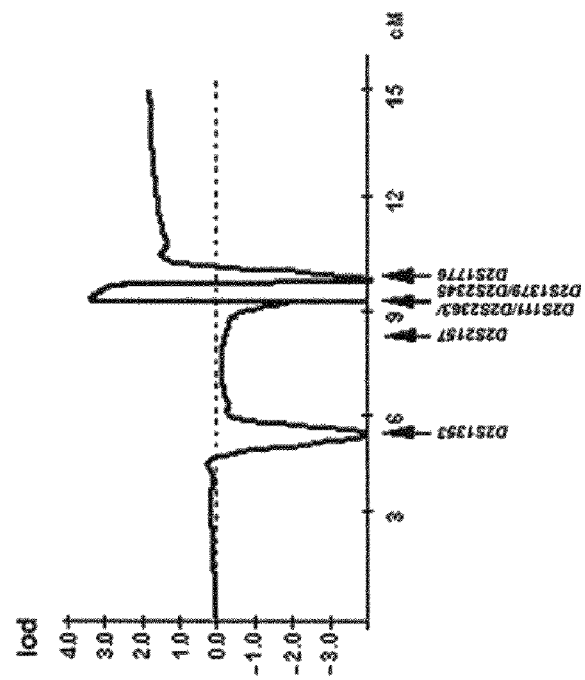
Figure 3A:
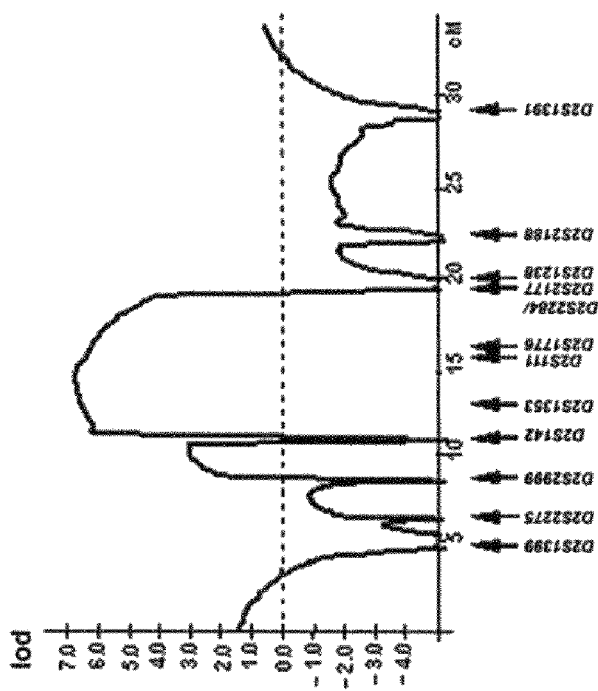

FIGS. 3a-b are multipoint LOD score analyses of a consanguinity FTC family (Family 1, FIG. 3a) and a non-consanguinity FTC family (Family 2, FIG. 3b). FIG. 3a—homozygosity mapping for 12 informative markers spanning 18.1 cM. Note the maximum multipoint LOD score of 6.7 at D2S111 (HOMOZ). FIG. 3b—multipoint linkage map using 7 microsatellite markers. Note the peak LOD of 3.4 for markers D2S2363 and D2S1379 (GeneHunter).

Figure 4:
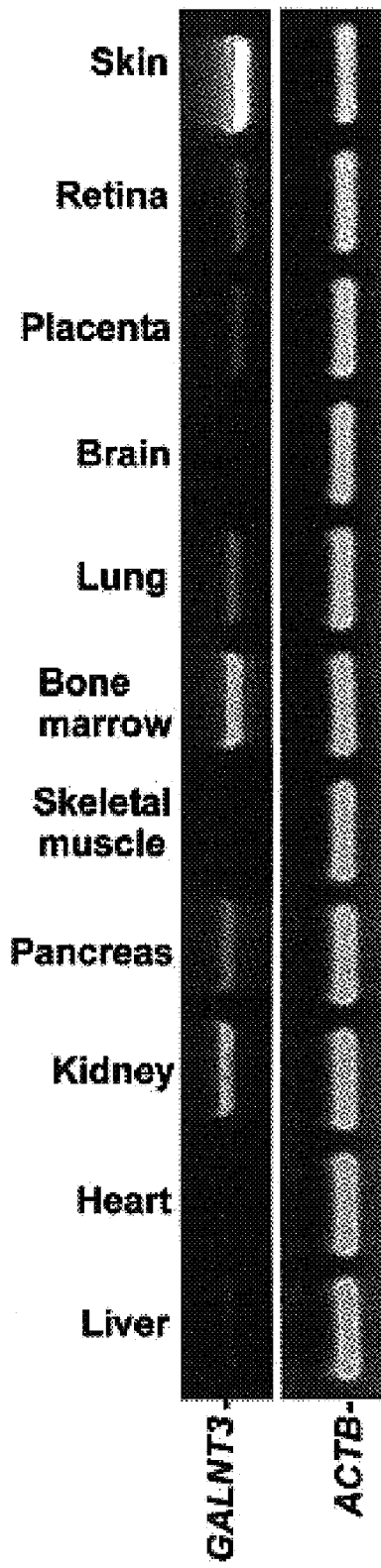

FIG. 4 illustrates RT-PCR determination of GALNT3 gene expression. RNA samples were extracted from various human tissues and the RT-PCR reaction was performed using the GALex6F (SEQ ID NO:23 and GALex9R (SEQ ID NO:25) primers followed by nested PCR using the GALex6F and GALex8R (SEQ ID NO:24) primers which are specific for GALNT3 transcript. Note the high-intensity bands obtained in RNA samples obtained from the skin, bone marrow and kidney. The RT-PCR product of the β-actin transcript (obtained using the Actin 5' and Actin 3' primers, SEQ ID NOs:26 and 27) was used as a measure of the level of RNA in each sample.

Figure 5A:
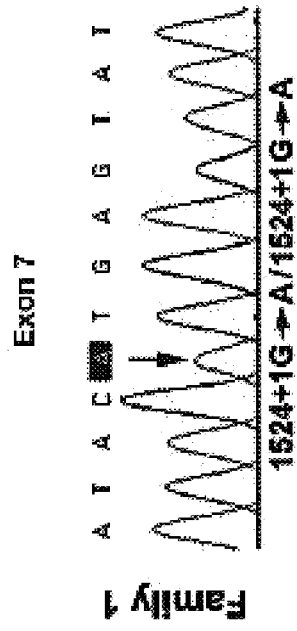
Figure 5C:
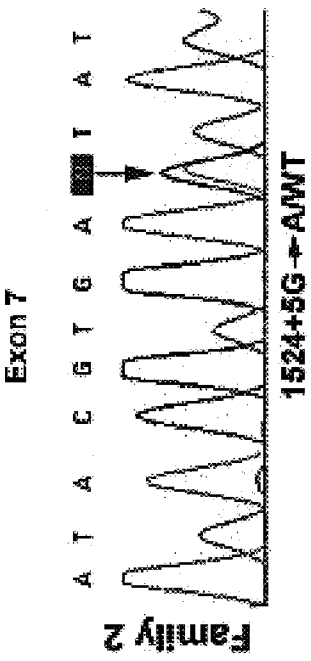
Figure 5B:
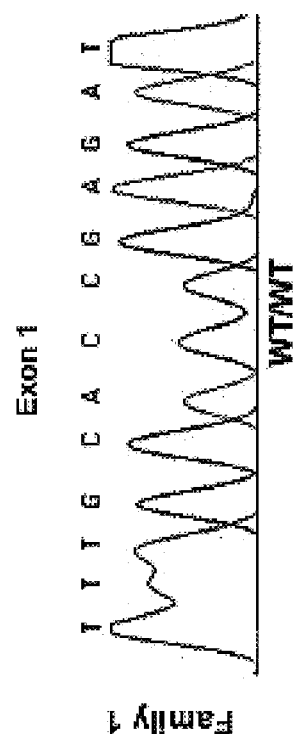

FIGS. 5a-d illustrate GALNT3 mutation analysis in FTC families. Shown are DNA sequencing chromatograms depicting the genomic sequence of exon 1 (FIGS. 5a-b) and exon 7 (FIG. 5c-d) of the GALNT3 gene in two FTC families. FIG. 5a—the wildtype sequence of exon 1 in family 1; FIG. 5b—the presence of a heterozygous C→T transition at position 484 of the GALNT3 mRNA sequence (GenBank Accession No. NM_004482, SEQ ID NO:29) creating a TGA termination codon (R162x) in exon 1 of affected individuals of family 2; FIG. 5c—the presence of a homozygous G→A transition at position 1524+1 (GALNT3 genomic contig GenBank Accession No. NT_005403) in affected individuals of family 1, FIG. 5d—the presence of a heterozygous G→A transition at position 1524+5 (GenBank Accession No. NT_005403) in all affected individuals of family 2.

Figure 6A:
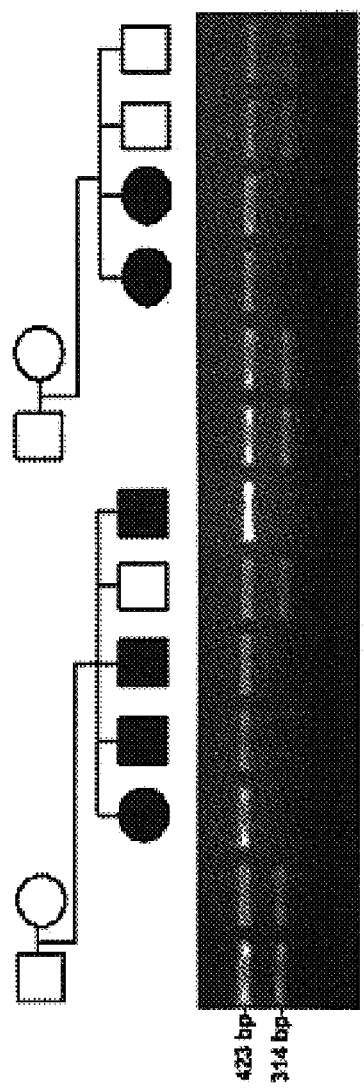
Figure 6B:
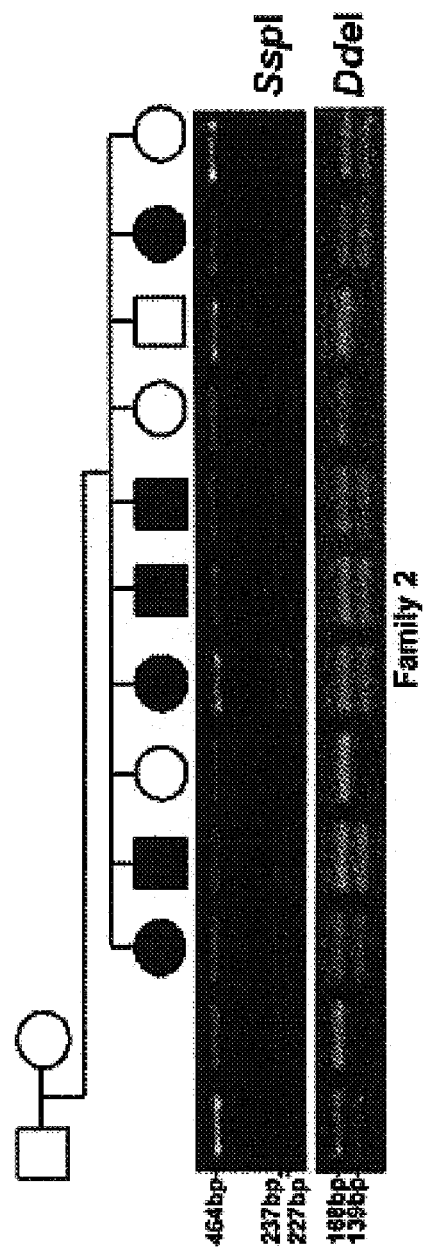

FIGS. 6a-b are RFLP analyses depicting the segregation of the pathogenic mutations in families 1 and 2. FIG. 6a-segregation of the 1524+1G→A mutation in family 1. The 1524+1G→A nucleic acid change abolishes a recognition site for BsaAI; consequently, digestion of a PCR amplicon encompassing exon 7 generates an homozygous (uncut) 423 bp product in affected individuals, while heterozygous carriers of the mutation display an additional fragment of 314 bp. FIG. 6b-segregation of the 1524+5G→A and R162X mutations in family 2. The 1524+5G→A and R162X nucleic acid changes create novel recognition sites for endonucleases SspI (upper gel) and DdeI (lower gel) respectively; hence, affected individuals in family 2 display an additional fragment upon digestion of the relevant PCR amplicons (exons 7 and 1, respectively) with the corresponding restriction enzymes.

Figure 7:
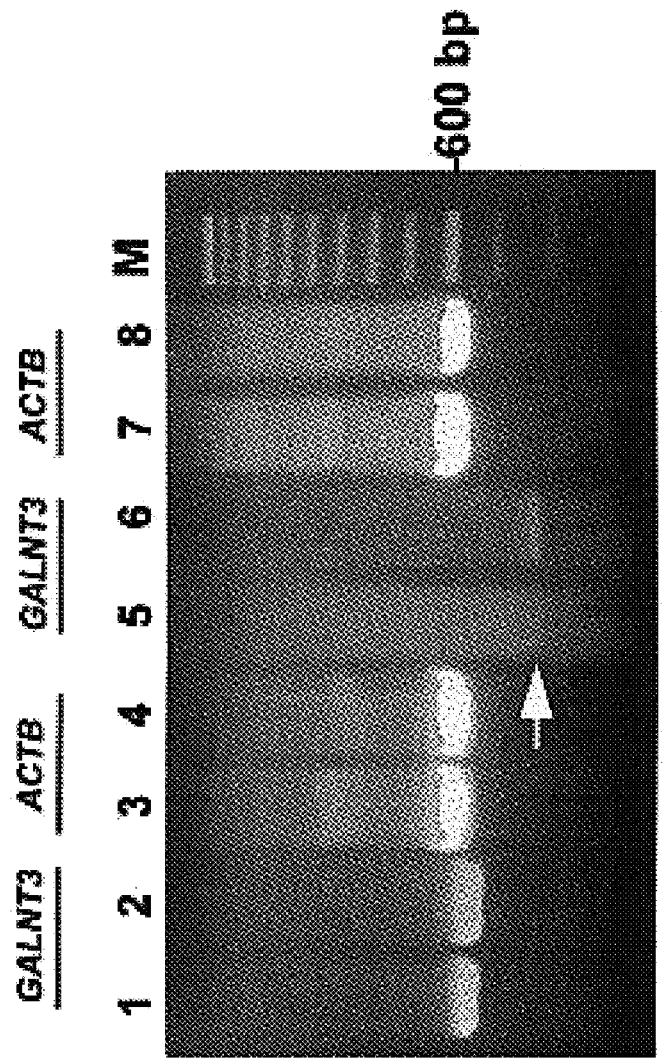

FIG. 7 is an RT-PCR analysis depicting the expression of GALNT3. RNA samples extracted from skin (lanes 1, 3, 5, 7) or blood lymphocytes (lanes 2, 4, 6, 8) of a healthy individual (lanes 1-4) and an FTC affected individual (patient No. 01001 of family 1, lanes 5-8) were subjected to RT-PCR analysis using the GALNT3 (lanes 1-2,5-6) or β-actin (ACTB, lanes 3-4,7-8) PCR primers as described in FIG. 4 hereinabove. Note the aberrant low-intensity, low-molecular weight GALNT3 RT-PCR products obtained using RNA from skin (lane 5, arrow) and blood lymphocytes (lane 6) of the FTC affected individual as compared with the high-intensity GALNT3 RT-PCR products obtained using RNA from skin (lane 1) and blood lymphocytes (lane 2) of the healthy individual. Also note the similar intensity bands of β-actin RT-PCR products in both affected and healthy individuals (compare lanes 3-4 to lanes 7-8).

Figure 8:
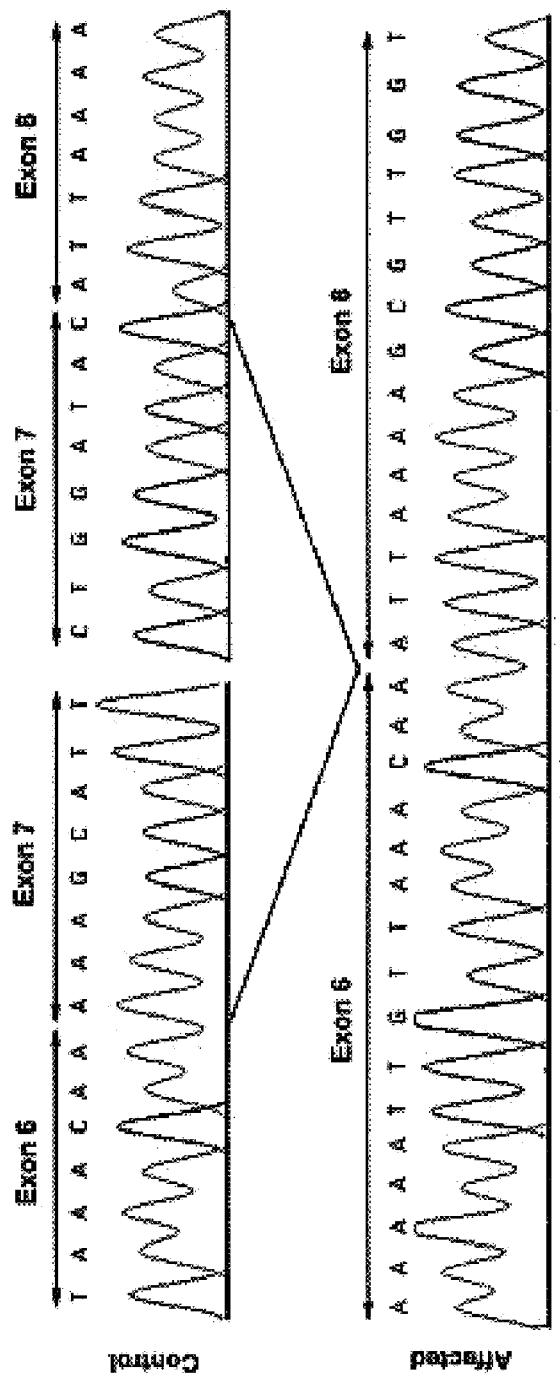

FIG. 8 is a DNA sequencing chromatogram depicting the absence of exon 7 in a blood RNA sample of an FTC affected individual. Sequence analysis was performed on the aberrant low-molecular weight RT-PCR product observed in FIG. 7 lane 6 using the GALex6F (SEQ ID NO:23) and GALex8R (SEQ ID NO:24) nested PCR primers. Note the absence of exon 7 sequence in the aberrant low-molecular weight splice product from the blood sample of the affected individual.

DESCRIPTION OF THE PREFERRED EMBODIMENTS

The present invention is of upregulators and downregulators of GalNAc-T3 which can be used in treating disorders associated with abnormal phosphate levels. Specifically, the present invention can be used to treat familial tumoral calcinosis and other disorders associated with hyperphosphatemia, as well as disorders associated with hypophosphatemia.

The principles and operation of the methods of treating disorders associated with abnormal phosphate metabolism according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Familial tumoral calcinosis (FTC; MIM211900) is a severe autosomal recessive metabolic disorder manifesting with hyperphosphatemia and massive calcium deposits in the skin and subcutaneous tissues. Current methods of treating patients affected with this disease and other hyperphosphatemia—related disorders (e.g., end-stage renal failure, pseudohypoparathyroidism, hypoparathyroidism) include the use of aluminum- or calcium-based phosphate-binding agents. However, these phosphate-binders can cause bone toxicity, renal osteodystrophy, encephalopathy, hypercalcaemia and cardiovascular calcification. To overcome these limitations, aluminum and calcium free agents such as sevelamer hydrochloride and lanthanum carbonate were suggested for treatment of hyperphosphatemia (FOSRENOL®, AnorMED Inc.; Hutchison A J, 2004, Nephrol Dial Transplant. 19 Suppl 1:i19-24; Chertow G M., 2003, J Am Soc Nephrol. 14: S310-4). These agents suppress phosphate re-absorption in the intestinal track. Although safer than aluminum, sevelamer was found to be less effective than the aluminum-based phosphate binder (Cizman B. 2003, Nephrol. Dial. Transplant. 18 Suppl 5:v47-9). On the other hand, lanthanum was found to be effective and well-tolerated (Joy M S et al., 2003, Am. J. Kidney Dis. 42: 96-107). However, both of these expensive agents are used for treating the symptoms and not the cause of hyperphosphatemia.

While reducing the present invention to practice, the present inventors have uncovered deleterious mutations in the GALNT3 gene encoding GalNAc-T3 in individuals affected with familial tumoral calcinosis (FTC). Moreover, the present inventors have uncovered that inducers of GalNAc-T3 can be used in treating FTC and other hyperphosphatemia-related disorders, and that inhibitors of GalNAc-T3 can be used to treat hypophosphatemia-related disorders.

Thus, according to one aspect of the present invention there is provided a method of treating a disorder associated with abnormal phosphate metabolism in an individual.

As used herein, the term "individual" refers to a human being suffering from a disease associated with abnormal phosphate level, i.e., hyperphosphatemia or hypophosphatemia due to a genetic disease (e.g., an individual having familial tumoral calcinosis), hormonal imbalance (e.g., hyperparathyroidism), renal disease (as a result of e.g., hemodialysis) and the like.

The phrase "treating" refers to inhibiting or arresting the development of a disease, disorder or condition and/or causing the reduction, remission, or regression of a disease, disorder or condition in an individual suffering from, or diagnosed with, the disease, disorder or condition. Those of skill in the art will be aware of various methodologies and assays which can be used to assess the development of a disease, disorder or condition, and similarly, various methodologies and assays which can be used to assess the reduction, remission or regression of a disease, disorder or condition.

As used herein "abnormal phosphate metabolism" refers to abnormal levels of serum phosphate, which may reflect abnormal absorption of phosphate in the intestinal tract or abnormal phosphate excretion in both the kidney and intestinal tract (i.e., via fecal excretion). Thus, any deviation from the normal range of phosphate in the plasma (i.e., 2.5-4.5 mg/dl), can be referred to as being abnormal.

The phrase "disorder associated with abnormal phosphate metabolism" refers to hyper—or hypophosphatemia—related disorders, i.e., the presence of excess of phosphate in the serum (i.e., above 4.5 mg/dl) or insufficient levels of phosphate (i.e., under 2.5 mg/dl), respectively.

The method according to this aspect of the present invention is effected by providing to an individual in need thereof an agent capable of regulating an expression level and/or activity of GalNAc-T3.

The term "GalNAc-T3" as used herein refers to the UDP-N-acetyl-alpha-D-galactosamine:polypeptide N-acetylgalactosaminyltransferase 3, which a member of the GalNAc-transferases family. Protein members of this family (e.g., GalNAc-T2, -T4, -T6, -T8) transfer N-acetyl galactosamine to the hydroxyl group of a serine or threonine residue in the first step of O-linked oligosaccharide biosynthesis. Individual GalNAc-transferase proteins have distinct activities and initiation of O-glycosylation is regulated by a repertoire of GalNAc-transferases. It will be appreciated that although these proteins share high sequence homology, each of the GalNAc-transferase proteins exhibits different substrate specificities. For example, the GalNAc-T3 exhibits substrate specificity towards $HIV_{H1B}gp120$, Fibronectin, Prion-a, CD59, Muc1a, Muc2, EA2, and Muc7.

The term "regulating" as used herein refers to upregulating (i.e., increasing) or downregulating (i.e., inhibiting or decreasing) of the expression and/or activity of GalNAc-T3.

According to preferred embodiments of the present invention the disorder associated with abnormal phosphate metabolism is hyperphosphatemia and thus the method of the present invention is effected by upregulating expression or activity of GalNAc-T3. Non-limiting examples of hyperphosphatemia-related disorders which can be treated according to this aspect of the present invention include familial tumoral calcinosis (FTC), hyperphosphatemic calcinosis, hemodialysis, chronic renal failure and end-stage renal failure.

Upregulation of GalNAc-T3 can be effected at the genomic level (i.e., activation of transcription via promoters, enhancers, regulatory elements), at the transcript level (i.e., correct splicing, polyadenylation, activation of translation) or at the protein level (i.e., post-translational modifications, interaction with substrates and the like).

Following is a list of agents capable of upregulating the expression level and/or activity of GalNAc-T3.

An agent capable of upregulating expression level of a GalNAc-T3 may be an exogenous polynucleotide sequence designed and constructed to express at least a functional portion of the GalNAc-T3 protein. Accordingly, the exogenous polynucleotide sequence may be a DNA or RNA sequence encoding a GalNAc-T3 molecule, capable of modulating phosphate metabolism.

The phrase "functional portion" as used herein refers to part of the GalNAc-T3 protein (i.e., a polypeptide) which exhibits functional properties of the enzyme such as binding to a substrate. According to preferred embodiments of the present invention the functional portion of GalNAc-T3 is a polypeptide sequence including amino acids 188-374 (region of glycosyl transferase) and/or 507-629 (region of ricin-type beta trefoil) as set forth in SEQ ID NO:28. Preferably, the functional portion of GalNAc-T3 is a polypeptide sequence including amino acids 13-633, more preferably, amino acids 1-633 as set forth in SEQ ID NO:28.

GalNAc-T3 has been cloned from human and mouse sources. Thus, coding sequences information for GalNAc-T3 is available from several databases including the GenBank database available through ncbidotnlmdotnihdotgov/.

To express exogenous GalNAc-T3 in mammalian cells, a polynucleotide sequence encoding a GalNAc-T3 (GenBank Accession number NM_004482, SEQ ID NO:29) is preferably ligated into a nucleic acid construct suitable for mammalian cell expression. Such a nucleic acid construct includes a promoter sequence for directing transcription of the polynucleotide sequence in the cell in a constitutive or inducible manner.

It will be appreciated that the nucleic acid construct of the present invention can also utilize GalNAc-T3 homologues which exhibit the desired activity (i.e., transferring N-acetyl galactosamine to the hydroxyl group of a serine or threonine residue in the first step of O-linked oligosaccharide biosynthesis). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to SEQ ID NO:29, as determined using the BestFit software of the Wisconsin sequence analysis package, utilizing the Smith and Waterman algorithm, where gap weight equals 50, length weight equals 3, average match equals 10 and average mismatch equals −9.

Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the inducible promoter of the alkaline phosphates gene (Dollard M A and Billard P J. 2003. Whole-cell bacterial sensors for the monitoring of phosphate bioavailability. Microbiol. Methods, 55: 221-9) and the tetracycline-inducible promoter (Zabala M, et al., Cancer Res. 2004, 64 (8): 2799-804).

The nucleic acid construct (also referred to herein as an "expression vector") of the present invention includes additional sequences which render this vector suitable for replication and integration in prokaryotes, eukaryotes, or preferably both (e.g., shuttle vectors). In addition, a typical cloning vectors may also contain a transcription and translation initiation sequence, transcription and translation terminator and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase the efficiency of GalNAC-T3 mRNA translation. Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

The expression vector of the present invention can further include additional polynucleotide sequences that allow, for example, the translation of several proteins from a single mRNA such as an internal ribosome entry site (IRES) and sequences for genomic integration of the promoter-chimeric polypeptide.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRepS, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., 2004 (Arch Virol. 149: 51-60).

Recombinant viral vectors are useful for in vivo expression of GalNAC-T3 since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of the present invention into stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

It will be appreciated that upregulation of GalNAc-T3 can be also effected by administration of GalNAc-T3-expressing cells into the individual.

GalNAc-T3-expressing cells can be any suitable cells, such as kidney, bone marrow, keratinocyte and lymphocyte cells which are derived from the individuals and are transfected ex vivo with an expression vector containing the polynucleotide designed to express GalNAc-T3 as described hereinabove.

Administration of the GalNAc-T3-expressing cells of the present invention can be effected using any suitable route such as intravenous, intra peritoneal, intra kidney, intra gastrointestinal track, subcutaneous, transcutaneous, intramuscular, intracutaneous, intrathecal, epidural and rectal. According to presently preferred embodiments, the GalNAc-T3-expressing cells of the present invention are introduced to the individual using intravenous, intra kidney, intra gastrointestinal track and/or intra peritoneal administrations.

GalNAc-T3-expressing cells of the present invention can be derived from either autologous sources such as self bone marrow cells or from allogeneic sources such as bone marrow or other cells derived from non-autologous sources. Since non-autologous cells are likely to induce an immune reaction when administered to the body several approaches have been developed to reduce the likelihood of rejection of non-autologous cells. These include either suppressing the recipient immune system or encapsulating the non-autologous cells or tissues in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylidene-acetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 µm. Such microcapsules can be further encapsulated with additional 2-5 µm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Thechnol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine)hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 µm (Canaple L. et al., Improving cell encapsulation through size control. J Biomater Sci Polym Ed. 2002;13: 783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

An agent capable of upregulating a GalNAc-T3 may also be any compound which is capable of increasing the transcription and/or translation of an endogenous DNA or mRNA encoding the GalNAc-T3 and thus increasing endogenous GalNAc-T3 activity.

An agent capable of upregulating a GalNAc-T3 may also be an exogenous polypeptide including at least a functional portion (as described hereinabove) of the GalNAc-T3.

Upregulation of GalNAc-T3 can be also achieved by introducing at least one GalNAc-T3 substrate. Non-limiting examples of such agents include $HIV_{H1B}gp120$, Fibronectin, Prion-a, CD59, Muc1a, Muc2, EA2, Muc7.

It will be appreciated that since GalNAc-T3 participates in phosphate metabolism downregulation thereof can be utilized to treat disorders which involve in hypophosphatemia, i.e., reduced levels of plasma phosphate.

Thus, according to another preferred embodiments of the present invention the disorder associated with abnormal phosphate metabolism is hypophosphatemia and the method of the present invention is effected by downregulating GalNAc-T3 expression or activity. Non-limiting examples of hypophosphatemia—related disorders which can be treated according to the method of the present invention include X-linked vitamin D resistant hypophosphatemic rickets (HYP), hereditary hypercalciuria with hypophosphatemic rickets (HHRH), oncogenic hypophosphatemic osteomalacia (OHO), X-linked hypophosphatemic rickets (PHEX) and hyperparathyroidism.

Downregulation of GalNAc-T3 can be effected on the genomic and/or the transcript level using a variety of molecules which interfere with transcription and/or translation (e.g., antisense, siRNA, Ribozyme, DNAzyme), or on the protein level using e.g., antagonists, enzymes that cleave the polypeptide and the like.

Following is a list of agents capable of downregulating expression level and/or activity of GalNAc-T3.

One example, of an agent capable of downregulating a GalNAc-T3 is an antibody or antibody fragment capable of specifically binding GalNAc-T3. Preferably, the antibody specifically binds at least one epitope of a GalNAc-T3. As used herein, the term "epitope" refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to the present invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab') .sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (19.85) and Boerner et al., J. Immunol., 147 (1):86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10,: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

Another agent capable of downregulating a GalNAc-T3 is a small interfering RNA (siRNA) molecule. RNA interference is a two step process. The first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs [Hutvagner and Zamore Curr. Opin. Genetics and Development 12:225-232 (2002); and Bernstein Nature 409:363-366 (2001)].

In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al. (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the GalNAc-T3 mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl, T. 2001, ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (ambiondotcom/techlib/tn/91/912dothtml).

Second, potential target sites are compared to an appropriate genomic database (e.g., human, mouse, rat etc.) using any sequence alignment software, such as the BLAST software available from the NCBI server (ncbidotnlmdotnihdotgov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

For example, a suitable GalNAc-T3 siRNA can be the siRNA ID 14834 (Ambion Inc., Austin, Tex.).

Another agent capable of downregulating a GalNAc-T3 is a DNAzyme molecule capable of specifically cleaving an mRNA transcript or DNA sequence of the GalNAc-T3. DNAzymes are single-stranded polynucleotides which are capable of cleaving both single and double stranded target sequences (Breaker, R. R. and Joyce, G. Chemistry and Biology 1995;2:655; Santoro, S. W. & Joyce, G. F. Proc. Natl, Acad. Sci. USA 1997;943:4262). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine: pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in Joyce et al. U.S. Pat. No. 6,326,174 to Joyce et al, DNAzymes of similar design directed against the human Urokinase receptor were recently observed to inhibit Urokinase receptor expression, and successfully inhibit colon cancer cell metastasis in vivo (Itoh et al, 20002, Abstract 409, Ann Meeting Am Soc Gen Ther. asgtdotorg). In another application, DNAzymes complementary to bcr-ab1 oncogenes were successful in inhibiting the oncogenes expression in leukemia cells, and lessening relapse rates in autologous bone marrow transplant in cases of CML and ALL.

Downregulation of a GalNAc-T3 can also be effected by using an antisense polynucleotide capable of specifically hybridizing with an mRNA transcript encoding the GalNAc-T3.

Design of antisense molecules which can be used to efficiently downregulate a GalNAc-T3 must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 93540 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

For example, a suitable antisense oligonucleotides targeted against the GALNT3 mRNA (which is coding for the GalNAc-T3 protein) would be of the following sequences: CTGGCACATACACCTCTGG (SEQ ID NO:30).

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bcl-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

Another agent capable of downregulating a GalNAc-T3 is a ribozyme molecule capable of specifically cleaving an mRNA transcript encoding a GalNAc-T3. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

Another agent capable of downregulating GalNAc-T3 would be any molecule which binds to and/or cleaves GalNAc-T3. Such molecules can be GalNAc-T3 antagonists, or GalNAc-T3 inhibitory peptide.

It will be appreciated that a non-functional analogue of at least a catalytic or binding portion of GalNAc-T3 can be also used as an agent which downregulates GalNAc-T3.

Another agent which can be used along with the present invention to downregulate GalNAc-T3 is a molecule which prevents GalNAc-T3 activation or substrate binding.

Each of the upregulating or downregulating agents described hereinabove or the expression vector encoding GalNAc-T3 can be administered to the individual per se or as part of a pharmaceutical composition which also includes a physiologically acceptable carrier. The purpose of a pharmaceutical composition is to facilitate administration of the active ingredient to an organism.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the upregulating or downregulating agent or the expression vector encoding GalNAc-T3 which are accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichlorotetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (the upregulating or downregulating agent or the expression vector encoding GalNAc-T3) effective to prevent, alleviate or ameliorate symptoms of a disorder (e.g., hyperphosphatemia or hypophosphatemia) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition (See e.g., Fingl, et al., 1975, in "The Pharmacological Basis of Therapeutics", Ch. 1 p. 1).

Dosage amount and interval may be adjusted individually to provide plasma levels of the active ingredient are sufficient to prevent hyperphosphatemia or hypophosphatemia (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Thus, the teachings of the present invention can be used to treat individuals suffering from familial tumoral calcinosis (ie., an hyperphosphatemia disorder). For example, an expression vector (e.g., a viral vector) including a polynucleotide sequence encoding the GALNT3 mRNA (SEQ ID NO:29) and the suitable promoter sequences to enable expression in kidney and skin cells is introduced into the individual via intravenous administration. Expression of such a vector in kidney and/or skin is expected to upregulate the expression level and/or activity of GalNAc-T3 in those tissues and thus to correct the hyperphosphatemia. Dosage of such an expression vector should be calibrated using cell culture experiments and animal models. Success of treatment is preferably evaluated by determining plasma phosphate levels and the individual general health status.

It will be appreciated, that if such a treatment is employed early in childhood, i.e., prior to the appearance of calcium deposits, or even prior to the detection of hyperphosphatemia (generally at 21 months of age), it may prevent the complications associated with such a disease (i.e., massive calcium deposits in the skin and subcutaneous tissues). In addition, since the expression vector is targeted to somatic cells which exhibit limited half-life (depending upon the cell line transduced), such a treatment is expected to be repeated periodically in order to prevent hyperphosphatemia.

As is shown in FIG. 5c and Example 2 of the Examples section which follows, the present inventors have uncovered that a 1524+1G→A mutation in the GALNT3 gene, in a homozygous form, causes FTC in a consanguinity family (family 1). In addition, as is shown in FIGS. 5b and d and Example 2 of the Examples section which follows, FTC affected members of the non-consanguinity family (family 2) are double heterozygous for the R162X and 1524+5G→A mutations in the GALNT3 gene. Thus, the presence of deleterious mutations in the GALNT3 sequence encoding GalNAc-T3 can be used in diagnosing FTC in an individual.

Thus, according to another aspect of the present invention there is provided a method of diagnosing familial tumoral calcinosis in an individual.

The method is effected by identifying in a polynucleotide sequence derived from the individual at least one nucleic acid substitution resulting in downregulation of an expression level and/or activity of GalNAc-T3.

As used herein the "polynucleotide sequence" refers to any DNA or RNA sequence which is derived from cells of the individual. DNA and RNA samples can be obtained from any source of cells. Preferably, the DNA is derived from peripheral blood cells (obtained using a syringe), skin cells (obtained from a skin biopsy) or mouth epithelial cells (obtained from a mouth wash), and the RNA is derived from blood or skin cells. Methods of extracting such DNA and RNA samples are well known in the art.

As is mentioned before, deleterious mutations in the GALNT3 gene cause FTC. Thus, according to preferred embodiments of the present invention the polynucleotide sequence is an mRNA sequence encoding GALNT3 (e.g., GenBank Accession No. NM_004482, SEQ ID NO:29) or a genomic sequence region including the GALNT3 gene (e.g., SEQ ID NO:33).

As used herein, the phrase "nucleic acid substitution" refers to any mutation in the DNA sequence of an individual which can result in downregulation of the expression level and/or activity of GalNAc-T3. Non-limiting examples of such nucleic acid changes include a missense mutation (i.e., a mutation which changes an amino acid residue in the protein with another amino acid residue), a nonsense mutation (i.e., a mutation which introduces a stop codon in a protein), a frameshift mutation (i.e., a mutation, usually, deletion or insertion of nucleic acids which changes the reading frame of the protein, and may result in an early termination or in a longer amino acid sequence), a readthrough mutation (i.e., a mutation which results in an elongated protein due to a change in a coding frame or a modified stop codon), a promoter mutation (i.e., a mutation in a promoter sequence, usually 5' to the transcription start site of a gene, which result in up-regulation or down-regulation of a specific gene product), a regulatory mutation (i.e., a mutation in a region upstream or downstream, or within a gene, which affects the expression of the gene product), a deletion (i.e., a mutation which deletes coding or non-coding nucleic acids in a gene sequence), an insertion (i.e., a mutation which inserts coding or non-coding nucleic acids into a gene sequence), an inversion (i.e., a mutation which results in an inverted coding or non-coding sequence), a splice mutation (i.e., a mutation which results in abnormal splicing or poor splicing) and a duplication (i.e., a mutation which results in a duplicated coding or non-coding sequence).

It will be appreciated that certain nucleic acid substitutions can be present in non-affected individuals [e.g., single nucleotide polymorphism (SNP)]. Such an SNP can cause, for example, a missense mutation in the GalNAc-T3, which, when present in the heterozygous form can be harmless, however, when present together with another, deleterious mutation such as a nonsense mutation, can lead to FTC at various degrees. Thus, according to preferred embodiments of the present invention the nucleic acid substitution is an SNP.

The nucleic acid substitution of the present invention can be identified using a variety of approaches suitable for identifying sequence alterations. One option is to determine the entire gene sequence of a PCR reaction product. Alternatively, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

Following is a non-limiting list of methods which can be used to identify the nucleic acid substitution and/or SNPs in the GALNT3 gene.

Direct sequencing of a PCR product: This method is based on the amplification of a genomic sequence using specific PCR primers in a PCR reaction following by a sequencing reaction utilizing the sequence of one of the PCR primers as a sequencing primer. Sequencing reaction can be performed using, for example, the Applied Biosystems (Foster City, Calif.) ABI PRISM® BigDye™ Primer or BigDye™ Terminator Cycle Sequencing Kits.

Restriction fragment length polymorphism (RFLP): This method uses a change in a single nucleotide (the SNP nucleotide) which modifies a recognition site for a restriction enzyme resulting in the creation or destruction of an RFLP.

For example, RFLP can be used to detect the R162X mutation (C→T substitution at nucleotide 484 as set forth in SEQ ID NO:29) in a genomic DNA of an individual. Briefly, genomic DNA is amplified using the GALe1bR (SEQ ID NO:1) and GALe1bF (SEQ ID NO:2) PCR primers, and the resultant PCR product is subjected to digestion using a restriction enzyme such as BstDEI, DdeI (see e.g., FIG. 6b) or TspRI which are capable of differentially digesting a PCR product containing the T allele (and not the C allele) at position 484 of SEQ ID NO:29.

Single nucleotide mismatches in DNA heteroduplexes are also recognized and cleaved by some chemicals, providing an alternative strategy to detect single base substitutions, generically named the "Mismatch Chemical Cleavage" (MCC) (Gogos et al., Nucl. Acids Res., 18:6807-6817, 1990). However, this method requires the use of osmium tetroxide and piperidine, two highly noxious chemicals which are not suited for use in a clinical laboratory.

Allele specific oligonucleotide (ASO): In this method, an allele-specific oligonucleotide (ASO) is designed to hybridize in proximity to the polymorphic nucleotide, such that a primer extension or ligation event can be used as the indicator of a match or a mis-match. Hybridization with radioactively labeled allelic specific oligonucleotides (ASO) also has been applied to the detection of specific SNPs (Conner et al., Proc. Natl. Acad. Sci., 80:278-282, 1983). The method is based on the differences in the melting temperature of short DNA fragments differing by a single nucleotide. Stringent hybridization and washing conditions can differentiate between mutant and wild-type alleles.

It will be appreciated that ASO can be applied on a PCR product generated from genomic DNA. For example, to detect the R162X mutation, genomic DNA is amplified using the GALe1bR (SEQ ID NO:1) and the GALe1bF (SEQ ID NO:2) PCR primers, and the resultant PCR product is subjected to an ASO hybridization using the following oligonucleotide probe: 5'-CTTTGCACtGAGATCTTGG (SEQ ID NO:31) which is capable of hybridizing to the thymidine nucleotide at position 484 of SEQ ID NO:29. As a control for the hybridization, the CTTTGCACCGAGATCTTGG (SEQ ID NO:32) oligonucleotide probe is applied to detect the presence of the wildtype allele.

Denaturing/Temperature Gradient. Gel Electrophoresis (DGGE/TGGE): Two other methods rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this manner, variants can be distinguished, as differences in melting properties of homoduplexes versus heteroduplexes differing in a single nucleotide can detect the presence of SNPs in the target sequences because of the corresponding changes in their electrophoretic mobilities. The fragments to be analyzed, usually PCR products, are "clamped" at one end by a long stretch of G-C base pairs (30-80) to allow complete denaturation of the sequence of interest without complete dissociation of the strands. The attachment of a GC "clamp" to the DNA fragments increases the fraction of mutations that can be recognized by DGGE (Abrams et al., Genomics 7:463-475, 1990). Attaching a GC clamp to one primer is critical to ensure that the amplified sequence has a low dissociation temperature (Sheffield et al., Proc. Natl. Acad. Sci., 86:232-236, 1989; and Lerman and Silverstein, Meth. Enzymol., 155:482-501, 1987). Modifications of the technique have been developed, using temperature gradients (Wartell et al., Nucl. Acids Res., 18:2699-2701, 1990), and the method can be also applied to RNA:RNA duplexes (Smith et al., Genomics 3:217-223, 1988).

Limitations on the utility of DGGE include the requirement that the denaturing conditions must be optimized for each type of DNA to be tested. Furthermore, the method requires specialized equipment to prepare the gels and maintain the needed high temperatures during electrophoresis. The expense associated with the synthesis of the clamping tail on one oligonucleotide for each sequence to be tested is also a major consideration. In addition, long running times are required for DGGE. The long running time of DGGE was shortened in a modification of DGGE called constant denaturant gel electrophoresis (CDGE) (Borrensen et al, Proc. Natl. Acad. Sci. USA 88:8405, 1991). CDGE requires that gels be performed under different denaturant conditions in order to reach high efficiency for the detection of SNPs.

A technique analogous to DGGE, termed temperature gradient gel electrophoresis (TGGE), uses a thermal gradient rather than a chemical denaturant gradient (Scholz, et al., Hum. Mol. Genet. 2:2155, 1993). TGGE requires the use of specialized equipment which can generate a temperature gradient perpendicularly oriented relative to the electrical field. TGGE can detect mutations in relatively small fragments of DNA therefore scanning of large gene segments requires the use of multiple PCR products prior to running the gel.

Single-Strand Conformation Polymorphism (SSCP): Another common method, called "Single-Strand Conformation Polymorphism" (SSCP) was developed by Hayashi, Sekya and colleagues (reviewed by Hayashi, PCR Meth. Appl., 1:34-38, 1991) and is based on the observation that single strands of nucleic acid can take on characteristic conformations in non-denaturing conditions, and these conformations influence electrophoretic mobility. The complementary strands assume sufficiently different structures that one strand may be resolved from the other. Changes in sequences within the fragment will also change the conformation, consequently altering the mobility and allowing this to be used as an assay for sequence variations (Orita, et al., Genomics 5:874-879, 1989).

The SSCP process involves denaturing a DNA segment (e.g., a PCR product) that is labeled on both strands, followed by slow electrophoretic separation on a non-denaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

Dideoxy fingerprinting (ddF): The dideoxy fingerprinting (ddF) is another technique developed to scan genes for the presence of mutations (Liu and Sommer, PCR Methods Appli., 4:97, 1994). The ddF technique combines components of Sanger dideoxy sequencing with SSCP. A dideoxy sequencing reaction is performed using one dideoxy terminator and then the reaction products are electrophoresed on nondenaturing polyacrylamide gels to detect alterations in mobility of the termination segments as in SSCP analysis. While ddF is an improvement over SSCP in terms of increased sensitivity, ddF requires the use of expensive dideoxynucleotides and this technique is still limited to the analysis of fragments of the size suitable for SSCP (i.e., fragments of 200-300 bases for optimal detection of mutations).

In addition to the above limitations, all of these methods are limited as to the size of the nucleic acid fragment that can be analyzed. For the direct sequencing approach, sequences of greater than 600 base pairs require cloning, with the consequent delays and expense of either deletion sub-cloning or primer walking, in order to cover the entire fragment. SSCP and DGGE have even more severe size limitations. Because of reduced sensitivity to sequence changes, these methods are not considered suitable for larger fragments. Although SSCP is reportedly able to detect 90% of single-base substitutions within a 200 base-pair fragment, the detection drops to less than 50% for 400 base pair fragments. Similarly, the sensitivity of DGGE decreases as the length of the fragment reaches 500 base-pairs. The ddF technique, as a combination of direct sequencing and SSCP, is also limited by the relatively small size of the DNA that can be screened.

Genotyping technology (PYROSEQUENCING™, Inc. Westborough, Mass., USA): This technique is based on the hybridization of a sequencing primer to a single stranded, PCR-amplified, DNA template in the presence of DNA polymerase, ATP sulfurylase, luciferase and apyrase enzymes and the adenosine 5' phosphosulfate (APS) and luciferin substrates. In the second step the first of four deoxynucleotide triphosphates (dNTP) is added to the reaction and the DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. In the last step the ATP sulfurylase quantitatively converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a pyrogram™. Each light signal is proportional to the number of nucleotides incorporated.

ACYCLOPRIME™ (genotyping technology)(Perkin Elmer, Boston, Mass., USA): This technique is based on fluorescent polarization (FP) detection. Following PCR amplification of the sequence containing the SNP of interest, excess primer and dNTPs are removed through incubation with shrimp alkaline phosphatase (SAP) and exonuclease I. Once the enzymes are heat inactivated, the ACYCLOPRIME™-FP process uses a thermostable polymerase to add one of two fluorescent terminators to a primer that ends immediately upstream of the SNP site. The terminator(s) added are identified by their increased FP and represent the allele(s) present in the original DNA sample. The ACYCLOPRIME™ process uses ACYCLOPOL™, a novel mutant thermostable polymerase from the Archeon family, and a pair of ACYCLOTERMINATORS™ labeled with R110 and TAMRA, representing the possible alleles for the SNP of interest. ACYCLOTERMINATOR™ non-nucleotide analogs are biologically active with a variety of DNA polymerases. Similarly to 2',3'-dideoxynucleotide-5'- triphosphates, the acyclic analogs function as chain terminators. The analog is incorporated by the DNA polymerase in a base-specific manner onto the 3'-end of the DNA chain, and since there is no 3'-hydroxyl, is unable to function in further chain elongation. It has been found that AcycloPol has a higher affinity and specificity for derivatized ACYCLOTERMINATORS™ than various Taq mutant have for derivatized 2',3'-dideoxynucleotide terminators.

Reverse dot blot: This technique uses labeled sequence specific oligonucleotide probes and unlabeled nucleic acid samples. Activated primary amine-conjugated oligonucleotides are covalently attached to carboxylated nylon membranes. After hybridization and washing, the labeled probe, or a labeled fragment of the probe, can be released using oligomer restriction, i.e., the digestion of the duplex hybrid with a restriction enzyme. Circular spots or lines are visualized colorimetrically after hybridization through the use of streptavidin horseradish peroxidase incubation followed by development using tetramethylbenzidine and hydrogen peroxide, or via chemiluminescence after incubation with avidin alkaline phosphatase conjugate and a luminous substrate susceptible to enzyme activation, such as CSPD, followed by exposure to x-ray film.

It will be appreciated that advances in the field of SNP detection have provided additional accurate, easy, and inexpensive large-scale SNP genotyping techniques, such as dynamic allele-specific hybridization (DASH, Howell, W. M. et al., 1999. Dynamic allele-specific hybridization (DASH). Nat. Biotechnol. 17: 87-8), microplate array diagonal gel electrophoresis [MADGE, Day, I. N. et al., 1995. High-throughput genotyping using horizontal polyacrylamide gels with wells arranged for microplate array diagonal gel electrophoresis (MADGE). Biotechniques. 19: 830-5], the Taq-Man system (Holland, P. M. et al., 1991. Detection of specific polymerase chain reaction product by utilizing the 5'→3' exonuclease activity of *Thermus aquaticus* DNA polymerase. Proc Natl Acad Sci USA. 88: 7276-80), as well as various DNA "chip" technologies such as the GeneChip microarrays (e.g., Affymetrix SNP chips) which are disclosed in U.S. Pat. Appl. No. 6,300,063 to Lipshutz, et al. 2001, which is fully incorporated herein by reference, Genetic Bit Analysis (GBA™) which is described by Goelet, P. et al. (PCT Appl. No. 92/15712), peptide nucleic acid (PNA, Ren B, et al., 2004. Nucleic Acids Res. 32: e42) and locked nucleic acids (LNA, Latorra D, et al., 2003. Hum. Mutat. 22: 79-85) probes, Molecular Beacons (Abravaya K, et al., 2003. Clin Chem Lab Med. 41: 468-74), intercalating dye [Germer, S. and Higuchi, R. Single-tube genotyping without oligonucleotide probes. Genome Res. 9:72-78 (1999)], FRET primers (Solinas A et al., 2001. Nucleic Acids Res. 29: E96), AlphaScreen (Beaudet L, et al., Genome Res. 2001, 11 (4): 600-8), SNPstream (Bell P A, et al., 2002. Biotechniques. Suppl.: 70-2, 74, 76-7), Multiplex minisequencing (Curcio M, et al., 2002. Electrophoresis. 23: 1467-72), SnaPshot (Turner D, et al., 2002. Hum Immunol. 63: 508-13), MassEXTEND (Cashman J R, et al., 2001. Drug Metab Dispos. 29: 1629-37), GOOD assay (Sauer S, and Gut I G. 2003. Rapid Commun. Mass. Spectrom. 17: 1265-72), Microarray minisequencing (Liljedahl U, et al., 2003. Pharmacogenetics. 13: 7-17), arrayed primer extension (APEX) (Tonisson N, et al., 2000. Clin. Chem. Lab.

Med. 38: 165-70), Microarray primer extension (O'Meara D, et al., 2002. Nucleic Acids Res. 30: e75), Tag arrays (Fan J B, et al., 2000. Genome Res. 10: 853-60), Template-directed incorporation (TDI) (Akula N, et al., 2002. Biotechniques. 32: 1072-8), fluorescence polarization (Hsu T M, et al., 2001. Biotechniques. 31: 560, 562, 564-8), Colorimetric oligonucleotide ligation assay (OLA, Nickerson D A, et al., 1990. Proc. Natl. Acad. Sci. USA. 87: 8923-7), Sequence-coded OLA (Gasparini P, et al., 1999. J. Med. Screen. 6: 67-9), Microarray ligation, Ligase chain reaction, Padlock probes, Rolling circle amplification, Invader assay (reviewed in Shi M M. 2001. Enabling large-scale pharmacogenetic studies by high-throughput mutation detection and genotyping technologies. Clin Chem. 47: 164-72), coded microspheres (Rao K V et al., 2003. Nucleic Acids Res. 31: e66) and MassArray (Leushner J, Chiu N H, 2000. Mol Diagn. 5: 341-80).

It will be appreciated that nucleic acid substitutions can be also identified in mRNA molecules derived from the individual. Such mRNA molecules are first subjected to an RT-PCR reaction following which they are either directly sequenced or be subjected to any of the SNP detection methods described hereinabove.

As is shown in FIG. 8 and Example 2 of the Examples section which follows, sequencing of the RT-PCR product generated using the GALex6F (SEQ ID NO:23) and the GALex8R (SEQ ID NO:24) primers revealed the absence of exon 7 from the mature GALNT3 mRNA.

Thus, according to preferred embodiments of the present invention, identifying at least one nucleic acid substitution in the mRNA sequence encoding GALNT3 is effected using DNA sequencing of a GLANT3 RT-PCR product.

Downregulation or upregulation of the expression level and/or activity of GalNAc-T3 can be determined using molecular and immunological methods known in the art.

Following is a list of methods useful for detecting GALNT3 RNA level in cells of the individual.

Northern Blot analysis: This method involves the detection of a particular RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radio-isotopes or enzyme linked nucleotides. Detection may be using autoradiography, colorimetric reaction or chemiluminescence. This method allows both quantitation of an amount of particular RNA molecules and determination of its identity by a relative position on the membrane which is indicative of a migration distance in the gel during electrophoresis.

RT-PCR analysis: This method uses PCR amplification of relatively rare RNAs molecules. First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls.

RNA in situ hybridization stain: In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the slide is subjected to either a photographic emulsion which reveals signals generated using radio-labeled probes or to a colorimetric reaction which reveals signals generated using enzyme-linked labeled probes.

In situ RT-PCR stain: This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

Following is a list of immunological detection methods which can be used to detect the level of GalNAc-T3 protein in cells of the individual.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, calorimetric reaction or chemiluminescence. This method allows both quantitation of an amount of substrate and determination of its identity by a relative position on the membrane which is indicative of a migration distance in the acrylamide gel during electrophoresis.

Radio-immunoassay (RI4): In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical analysis: This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a calorimetric reaction may be required. It will be appreciated that immunohistochemistry is often followed by counterstaining of the cell nuclei using for example Hematoxyline or Giemsa stain.

Following is a list of enzymatic activity assays which can be used to determine GalNAc-T3 activity in cells of the individual.

In situ activity assay: According to this method, a chromogenic substrate is applied on the cells containing an active enzyme and the enzyme catalyzes a reaction in which the substrate is decomposed to produce a chromogenic product visible by a light or a fluorescent microscope.

In vitro activity assays: In these methods the activity of a particular enzyme is measured in a protein mixture extracted from the cells. The activity can be measured in a spectrophotometer well using colorimetric methods or can be measured in a non-denaturing acrylamide gel (i.e., activity gel). Following electrophoresis the gel is soaked in a solution containing a substrate and colorimetric reagents. The resulting stained band corresponds to the enzymatic activity of the protein of interest. If well calibrated and within the linear range of response, the amount of enzyme present in the sample is proportional to the amount of color produced. An enzyme standard is generally employed to improve quantitative accuracy.

The activity assays described hereinabove can use any of the GalNAc-T3 specific substrates, including, but not limited to, $HIV_{H1B}$gp120, Fibronectin, Prion-a, CD59, Muc1a, Muc2, EA2, Muc7.

It will be appreciated that mutations which downregulate the expression level and/or activity level of GalNAc-T3 can be also identified in a polypeptide sequence derived from the individual.

Thus, according to another aspect of the present invention there is provided a method of diagnosing familial tumoral calcinosis in an individual.

The method is effected by identifying in a polypeptide sequence derived from the individual at least one amino acid substitution capable of downregulating the expression level and/or activity of GalNAc-T3.

As used herein, the phrase "one amino acid substitution" refers to any change in a polypeptide sequence (e.g., substitution, deletion, duplication, methylation, acetylation, glycosylation, phosphorylation of an amino acid) which can cause downregulation of the expression level and/or activity of the GalNAc-T3.

According to preferred embodiments of the present invention the amino acid substitution is identified in the GalNAc-T3 protein as set forth in SEQ ID NO:28.

Amino acid substitutions can be identified using any method known in the art, preferably, using an antibody which is capable of identifying between two polymorphs of the same protein.

The term "polymorph" as used herein refers to one form of a protein which is different in at least one amino acid or a modification on at least one amino acid from another form of the same protein. For example, the substitution of a methionine residue with a valine residue of a certain protein. In this case one protein polymorph contains the methionine and the other protein polymorph contains the valine. Other protein polymorphs can be identified by the presence or absence of specific post-translational modifications such as the phosphorylation of a serine, threonine or tyrosine residue in a protein.

Determination of at least one amino acid substitution between two polymorphs of the GalNAc-T3 can be accomplished directly, by analyzing the GalNAc-T3 protein, or portions thereof. Such a direct analysis is often accomplished using an immunological detection method as described hereinabove.

As is mentioned before, agents which upregulate or downregulate GalNAc-T3 expression level and/or activity can be used to treat hyperphosphatemia or hypophosphatemia, respectively. Additional examples of such agents can be identified via in vitro and/or ex vivo assays.

Thus, according to another aspect of the present invention there is provided a method of identifying an agent suitable for treating a disorder associated with abnormal phosphate metabolism.

The method is effected by exposing GalNAc-T3 or cells expressing GalNAc-T3 to a plurality of molecules and selecting from them at least one molecule capable of regulating the expression level and/or the activity of the GalNAc-T3, such a molecule being the agent suitable for treating the disorder associated with abnormal phosphate metabolism.

As used herein, "exposing GalNAc-T3" refers to subjecting a GalNAc-T3 protein preparation to various test molecules. A GalNAc-T3 protein preparation can be obtained by extracting proteins from cells or tissues exhibiting high expression level of GalNAc-T3 (e.g., skin, kidney, blood) or by purifying a protein extract of eukaryotic cells which overexpress the GalNAc-T3 protein. Preferably, the GalNAc-T3 protein includes at least a catalytic (i.e., the region in the protein which is responsible for the catalytic activity of the protein) or binding (i.e., the region in the protein which is responsible for binding a substrate, receptor and the like) portion of the GalNAc-T3. For example, the catalytic domain of the GalNAc-T3, which includes the amino acids at positions 566-1122 of the GalNAc-T3 protein (GenBank Accession No. NP_004473, SEQ ID NO:28) can be used along with the present invention.

According to preferred embodiments of the present invention the GalNAc-T3 protein is set forth in SEQ ID NO:28.

The phrase "cells expressing GalNAc-T3" refers to eukaryotic cells, preferably mammalian cells, more preferably, human cells, which were transfected with an expression vector containing the GALNT3 polynucleotide (e.g., GenBank Accession No. NM_004482, SEQ ID NO:29) and are cultured in a tissue culture flask. Non-limiting examples of such cells include bone marrow cell, kidney cells, fibroblasts, epithelial cells and lymphoblastoid cells.

Once the GalNAc-T3 or cells expressing GalNAc-T3 are obtained, the test molecules (e.g., drugs, minerals, vitamins, and the like) are applied on the GalNAc-T3 or cells expressing GalNAc-T3 and the expression level and/or activity of GalNAc-T3 is detected using the molecular, immunological and biochemical methods which are fully described hereinabove. Molecules which exert significant modulations of GalNAc-T3 activity and/or expression level (i.e., upregulation or downregulation) become candidates for additional evaluations as suitable for treating disorders associated with abnormal phosphate metabolism.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., Ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (Eds.) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., Ed. (1994); "Culture of Animal Cells—A Manual of Basic Technique" by Freshney, Wiley-Liss, N.Y. (1994), Third Edition; "Current Protocols in Immunology" Volumes I-III Coligan J. E., Ed. (1994); Stites et al. (Eds.), "Basic and Clinical Immunology" (8th Edition), Appleton & Lange, Norwalk, Conn. (1994); Mishell and Shiigi (Eds.), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., Ed. (1984); "Nucleic Acid Hybridization" Hames, B. D., and Higgins S. J., Eds. (1985); "Transcription and Translation" Hames, B. D., and Higgins S. J., Eds. (1984); "Animal Cell Culture" Freshney, R. I., Ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Characterization of a Familial Tumoral Calcinosis (FTC) Critical Region

Familial tumoral calcinosis (FTC; MIM211900) is a severe autosomal recessive metabolic disorder manifesting with hyperphosphatemia and massive calcium deposits in the skin and subcutaneous tissues. To identify the genetic basis of FTC, linkage analysis was performed using DNA from informative FTC families, as follows.

Materials and Experimental Methods

FTC affected individuals—A total of 12 FTC affected individuals belonging to two large kindred of Druze and African American origin (FIGS. 1a-b), which have been extensively described in the literature (Steinherz, R. et al. 1985, Am. J. Dis. Child. 139: 816-819; Slavin, R. E., et al., 1993, Am. J. Surg. Path. 17: 788-802) were included in the study.

Linkage analysis—A genome wide scan using 362 microsatellite markers (InVitrogen, Cat. No. 20508, Huntsville, Ala., USA) was employed in a consanguinity FTC family (family 1, FIG. 1a).

RT-PCR analysis—RNA was extracted using the QIAGEN RNeasy kit (QIAGEN Inc., CA USA) from the following human cells or tissues: liver, heart, kidney, pancreas, skeletal muscle, bone marrow, lung, brain, placenta, retina, and skin. RT-PCR reactions were performed using the TITAN One Tube RT-PCR kit (Roche Molecular Biochemicals, Mannheim, Germany) and the GALek6F (SEQ ID NO:23) and GALex9R primers, following by a nested PCR reaction using the GALex6F and GALex8R (SEQ ID NO:24) primers (see Table 1, hereinbelow).

TABLE 1

RT-PCR primers and conditions

| Primer (SEQ ID NO:) | Sequence 5'→3' | Anneal. Temp. (° C.) |
|---|---|---|
| GALcx6F (SEQ ID NO:23) | GGCAGTTGGAGATTATGCCTTG | 60° C. |
| GALex8R (SEQ ID NO:24) | CAACATCCAGACATAGAGGCTG | 60° C. |
| GALex9R (SEQ ID NO:25) | CTGCTCTCCAGTGACAACTGTC | 60° C. |
| Beta Actin 5' (SEQ ID NO:26) | CGACGAGGCCCAGAGCAAGAGA | 60° C. |
| Beta Actin 3' (SEQ ID NO:27) | TCCAGGGCGACGTAGCACACGCTT | 60° C. |

Experimental Results

Clinical characteristics of FTC affected individuals—All twelve FTC affected individuals reported recurrent painful, calcified subcutaneous masses of up to 1 kg (FIG. 2a), often resulting in secondary infection and incapacitating mutilation. Three patients developed deep periarticular tumors (FIG. 2b) and one patient succumbed to the disease. All patients displayed hyperphosphatemia [range (mg/dl): family 1: 6.2-8.5; family 2: 5.2-6.6] but normal levels of calcium, parathyroid hormone (PTH) and 1,25-dihydroxyvitamin D3 (Vitamin D3).

Mapping of the FTC gene to chromosome 2q24-q31—Consanguinity in family 1 enabled the application of homozygosity mapping to identify a 15 Mb segment identical by descent in all affected individuals. This region is flanked by D2S142 and D2S2284/D2S2177 markers on 2q24-q31 (FIG. 1a). As is shown in FIG. 3a, a maximum multipoint LOD score of 6.7 was observed for the 15 Mb region using the MAPMAKER/HOMOZ (Kruglyak L, et al., 1995. Rapid multipoint linkage analysis of recessive traits in nuclear families, including homozygosity mapping. Am. J. Hum. Genet. 56: 519-27). Multipoint linkage analysis in family 2 using 7 markers in this critical region further reduced the interval to 3 Mb, flanked by D2S111 and D2S1776 (FIG. 1b) and yielded a maximum multipoint LOD score of 3.4 (FIG. 3b) using the GeneHunter (Kruglyak, L., et al., 1996, Am. J. Hum. Genet. 58: 1347-1363).

Analysis of FTC putative genes in the FTC critical region—Using the Mapviewer tool available via the NCBI web site (ncbidotnlmdotnihdotgov/), 11 genes were identified within the FTC region, among which B3GALT1, SCN7A, SCN9A, SCN1A, STK39 are thought to play a role in neural or neuroendocrine tissues, while the function of TAIP-2, CMYA3, FLJ11457, LOC90643, LOC253782 is mostly unknown. The last positional candidate gene, GALNT3, encodes the UDP-N-acetyl-alpha-D-galactosamine:polypeptide N-acetylgalactosaminyltransferase 3 (GalNAc-T3) (Bennett, E. P., et al., 1996, Biol. Chem. 271: 17006-17012). The GalNAc-T3 protein belongs to a large family of Golgi-associated biosynthetic enzymes that transfer GalNac from the sugar donor UDP-GalNac to serine and threonine residues, and thereby are responsible for initiating O-glycan synthesis, a prevalent form of post-translational modification (Ten Hagen, K. G., et al., 2003. Glycobiology 13: 1R-16R).

Tissue specific expression of the GALNT3 gene in skin and kidney—To determine if the GALNT3 gene is a putative FTC candidate gene, the expression pattern of the gene was determined using RT-PCR analysis. As is shown in FIG. 4, high level of expression was detected in RNA from both kidney and skin, two tissues of functional relevance to the pathogenesis of FTC [Steinherz, 1985 (Supra); Slavin, 1993 (Supra)].

These results demonstrate the identification of a 3 MB FTC critical region on chromosome 2q24-q31. Furthermore, the high expression level of GALNT3 in both kidney and skin suggest its involvement in the pathogenesis of FTC.

Example 2

Biallelic Deleterious Mutations in GALNT3, Encoding a Protein Involved in O-Linked Glycosylation, Cause Familial Tumoral Calcinosis To test whether mutations in the GALNT3 gene underlie the molecular basis of FTC, genomic DNA from FTC cases was subjected to sequence analysis of the GALNT3 coding sequence.

Materials and Experimental Methods

Sequencing analysis—Genomic DNA was amplified using PCR primers designed specific for the amplification of the GALNT3 coding exons. PCR primers and conditions are listed in Table 2, hereinbelow.

TABLE 2

PCR primers and conditions

| Primer (SEQ ID NO:) | Sequence 5'→3' | Anneal. Temp. (° C.) |
|---|---|---|
| GALe1bR (SEQ ID NO:1) | GCTCACCCCTCTCTCCCCTG | 60° C. |
| GALe1bF (SEQ ID NO:2) | CATTGATGCTGGTGAGAG | |
| GALe1aR (SEQ ID NO:3) | CTGAGGTGGACGGTCAAGGACAG | 60° C. |
| GALe1Af (SEQ ID NO:4) | GTAGGACTGAATAGCTACTAATAC | |
| GALe2R (SEQ ID NO:5) | CTGAGATGGCATACAGAGAGTAC | 60° C. |
| GALe2F (SEQ ID NO:6) | CTCTGGGTGAGTGATTTGCTTG | |
| GALe3R (SEQ ID NO:7) | CACAGAGCTGTTACCTGCTTGG | 60° C. |
| GALe3F (SEQ ID NO:8) | GCTCTGTGGTTTCATTAGCTTTC | |
| GALe4R (SEQ ID NO:9) | GCTATAAAGCAAACAGTGTGTAC | 60° C. |
| GALe4F (SEQ ID NO:10) | CAATAAATCTGAGGAAGAAAGAAATC | |
| GALe5R (SEQ ID NO:11) | GTGCACACATCTGTAATCATATG | 60° C. |
| GALe5F (SEQ ID NO:12) | CAATGGGAGAGGACACGAAGTAC | |
| GALe6R (SEQ ID NO:13) | GAATCGACGCAAAAGGACGTG | 60° C. |
| GALe6F (SEQ ID NO:14) | GAAATGGCAGGGGACAGAGAC | |
| GALe7R (SEQ ID NO:15) | GTAAAATCTCAAAAGCAATAAAGAAAG | 60° C. |
| GALe7F (SEQ ID NO:16) | CAGAAATGAACAGGCAGGCATG | |
| GALe8R (SEQ ID NO:17) | GCAACATCTCACTTGTGCTTG | 60° C. |
| GALe8F (SEQ ID NO:18) | GATACGTGAGTATTTTGCTGTTCC | |

TABLE 2-continued

PCR primers and conditions

| Primer (SEQ ID NO:) | Sequence 5'→3' | Anneal. Temp. (° C.) |
|---|---|---|
| GALe9R (SEQ ID NO:19) | GATATATTCTCTTATCACATGGG | 60° C. |
| GALe9F (SEQ ID NO:20) | GGCTATTGTATCGTCTATCAC | |
| GALe10R (SEQ ID NO:21) | CTACAGTGTATGCCTAGTCACAG | 60° C. |
| GALe10F (SEQ ID NO:22) | CTGTGTGCCTCTCTTCATTATG | |

Experimental Results

Figure 5D:
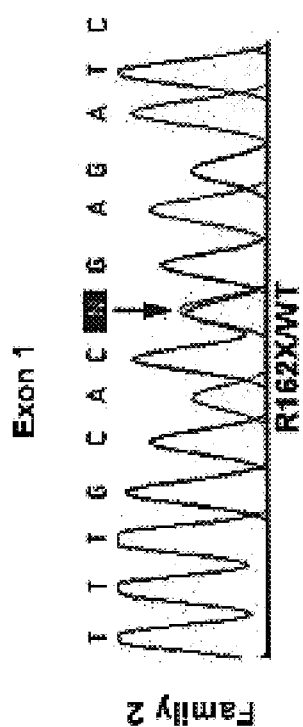

FTC patients of family 2 are compound heterozygous of a nonsense mutation in exon 1 and a splice mutation in intron 7 of GALNT3—As is shown in FIGS. 5a-b, affected individuals of family 2 were found to be carriers of a nonsense mutation in exon 1, in which a C→T substitution resulted in a change of the CGA codon of Arginine at position 162 of the GALNT3 protein (GenBank Accession No. NP_004473 SEQ ID NO:28) with a termination codon (i.e., TGA). Moreover, as is shown in FIG. 5c-d, the same affected individuals of family 2 were carriers of a splice mutation in intron 7 at position 1524+5G→A from the ATG translation start site (GLANT3 mRNA sequence—GenBank Accession No. NM_004482, SEQ ID NO:29; GLANT3 genomic contig—GenBank Accession No. NT_005403).

Homozygous splice mutation in intron 7 of the consanguinity Druze FTC family 1—Sequence analysis of all 10 coding exons of the GALNT3 gene from the Druze family revealed the presence of a homozygous G→A transition at position 1524+1 (from the ATG translation start site GenBank Accession No. NM_004482, SEQ ID NO: 29), resulting in the disruption of the intron 7 donor splice site consensus sequence (FIGS. 5c-d).

Noteworthy, all three mutations (i.e., 1524+1G→A; 1524+5G→A, R162X) were excluded from a panel of at least 290 chromosomes derived from healthy unrelated individuals.

Furthermore, as can be seen in FIGS. 6a-b, a complete co-segregation of the mutations with the disease phenotype was confirmed by PCR-RFLP in both FTC families.

Analysis and Discussion—The nonsense R162X mutation is expected to result in a non-functional null allele due to premature termination of protein translation. Mutations 1524+1G→A and 1524+5G→A alter the same splice donor site in intron 7. In contrast to the normal splicing score of 0.93 obtained for the intron 7 splice donor site predicted by the Splice Site Prediction by Neural Network software (fruitfly-dotorg/seq_tools/splicedothtml), the calculated score of this sequence carrying a G→A mutation at position 1524+1 or 1524+5 was 0.00.

The 1524+1G→A splice mutation results in an absence of exon 7 from the GALNT3 mRNA transcript—To further assess the consequences of the 1524+1G→A splice site mutation, the expression pattern of GALNT3 was assessed using RT-PCR. As shown in FIG. 7, while a normal band of approximately 600 bp was detected in skin and blood samples of a healthy individual, no wildtype GALNT3 transcript was detected in RNA from affected individuals. In addition, low amounts of an aberrant splice variant were detected in RNA derived from both skin and blood samples. Sequence analysis of the aberrant shorter transcript revealed the presence of a shorter GALNT3 transcript lacking exon 7 nucleotide sequence (FIG. 8). This shorter mRNA transcripts results in an in-frame deletion of 44 amino acid residues in the mature polypeptide, destroying most of the linker region located between the catalytic domain and the ricin-like domain of the glycosyltransferase.

Altogether, these results demonstrate that deleterious mutations in the GALNT3 sequence underlie the molecular basis of FTC.

Analysis and Discussion—Since the original description of FTC more than a century ago by Giard, J. M, 1898 (Sur la calcification hibernate. Compes. Rend. Seanes. Soc. Biol. So. 1013-1015), the pathogenesis of this disease has stirred up a large number of investigations but has remained mostly elusive.

The results presented here suggest a role for GalNAc-T3-mediated glycosylation in the control of phosphatonin activity. Although the NetOGlyc 3.0 software (cbsdotdtudotdk/services/NetOGlyc) identified potential O-glycosylation sites in FGF23 (setting O-glycosylation score significance at >0.5), this molecule is unlikely to mediate the deleterious effects of GALNT3 mutations in FTC. Indeed, impaired FGF23 activity in a murine model was recently shown to lead to prominent bone tissue abnormalities [Shimada, T et al. J Clin Invest. 113, 561-568 (2004)], which are absent in FTC patients. Of note, FGF23 circulating levels measured by ELISA (Immutopics, Calif.) were significantly elevated in 6 FTC patients (1710+864 RU/ml) as compared with 6 healthy controls (56+38 RU/ml), possibly reflecting a compensatory response to hyperphosphatemia. Thus GalNAc-T3 may affect phosphate homeostasis by modulating the activity of another phosphatonin or PHEX [Jan De Beur, 2002 (Supra)]. Alternatively, it may directly regulate non-circulating elements within tissues where GALNT3 is expressed such as the skin, where calcium deposition occurs [Steinherz, 1985 (Supra); Slavin, 1993 (Supra)], the bone, where candidate phosphatonins are expressed [Schiavi, 2004 (Supra); Quarles, 2003. (Supra)], and/or the kidneys and gastrointestinal tract, where phosphate transport occurs [Jan De Beur, 2002, (Supra)].Given the existence of more than 20 ppGaNTase isoforms [Ten Hagen, 2003 (Supra)] substrate specificity and/or functional redundancy may account for the restricted nature of the FTC phenotype despite GALNT3 widespread tissue expression.

GalNAc-T3 may not be the sole regulator of phosphate homeostasis in peripheral tissues. Prince et al [Prince M. J. et al. Ann Intern Med. 96, 586-591 (1982)] established 2 decades ago that FTC can also present with normal phosphate levels. Using haplotype analysis in four families with normophosphatemic FTC, this FTC variant was excluded from linkage to 2q24-q31 (not shown), suggesting that normophosphatemic and hyperphosphatemic FTC are non-allelic disorders.

In summary, these results establish autosomal recessive mutations in GALNT3 as the molecular cause of hyperphosphatemic FTC and demonstrate the pathological consequences of a genetic defect in a mucin-type O-glycosylation pathway. The identification of the FTC gene should not only benefit the affected families, to which molecular testing can now be offered, but may also shed new light on the mechanisms regulating phosphate metabolism in health and disease, with obvious implications for the treatment of acquired disorders manifesting with hyperphosphatemic calcinosis, such as chronic renal failure.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of diagnosing familial tumoral calcinosis (FTC) in a human individual, the method comprising identifying in a polynucleotide sequence consisting of SEQ ID NO:29 or 33 of the individual, a C→T transition at position 484 of SEQ ID NO:29 and a G→A transition at position 1524+5 (intron 7 of SEQ ID NO:33) in compound heterozygous form, thereby diagnosing familial tumoral calcinosis in the individual.

2. A method of identifying a molecular basis of familial tumoral calcinosis (FTC) in a human individual diagnosed with the FTC, the method comprising identifying in a polynucleotide sequence consisting of SEQ ID NO:29 or 33 of the individual at least one nucleic acid substitution selected from the group consisting of a C→T transition at position 484 of SEQ ID NO:29, a G→A transition at position 1524+1 (intron 7 of SEQ ID NO:33) and a G→A transition at position 1524+5 (intron 7 of SEQ ID NO:33), wherein said nucleic acid substitution is present in the individual in a homozygous form or a compound heterozygous form, thereby identifying the molecular basis familial tumoral calcinosis in the individual.

3. The method of claim 1, wherein said identifying is effected using a method selected from the group consisting of DNA sequencing, restriction fragment length polymorphism (RFLP) analysis), allele specific oligonucleotide (ASO) analysis, Denaturing/Temperature Gradient Gel Electrophoresis (DGGE/TGGE), Single-Strand Conformation Polymorphism (SSCP) analysis, Dideoxy fingerprinting (ddF), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, MassEXTEND, MassArray, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Rolling circle amplification, and Invader assay.

4. The method of claim 1, wherein said identifying is effected using DNA sequencing of a GALNT3 RT-PCR product.

5. The method of claim 2, wherein said identifying at least one nucleic acid substitution in said polynucleotide sequence consisting of SEQ ID NO:33 is effected using a method selected from the group consisting of DNA sequencing, restriction fragment length polymorphism (RFLP analysis), allele specific oligonucleotide (ASO) analysis, Denaturing/Temperature Gradient Gel Electrophoresis (DGGE/TGGE), Single-Strand Conformation Polymorphism (SSCP) analysis, Dideoxy fingerprinting (ddF), pyrosequencing analysis, acycloprime analysis, Reverse dot blot, GeneChip microarrays, Dynamic allele-specific hybridization (DASH), Peptide nucleic acid (PNA) and locked nucleic acids (LNA) probes, TaqMan, Molecular Beacons, Intercalating dye, FRET primers, AlphaScreen, SNPstream, genetic bit analysis (GBA), Multiplex minisequencing, SNaPshot, MassEXTEND, MassArray, GOOD assay, Microarray miniseq, arrayed primer extension (APEX), Microarray primer extension, Tag arrays, Coded microspheres, Template-directed incorporation (TDI), fluorescence polarization, Colorimetric oligonucleotide ligation assay (OLA), Sequence-coded OLA, Microarray ligation, Ligase chain reaction, Padlock probes, Rolling circle amplification, and Invader assay.

6. The method of claim 2, wherein said identifying said at least one nucleic acid substitution in said polynucleotide sequence consisting of SEQ ID NO:29 is effected using DNA sequencing of a GALNT3 RT-PCR product.

* * * * *

```
                          SEQUENCE LISTING

<160> NUMBER OF SEQ ID NOS: 33

<210> SEQ ID NO 1
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 1
gctcacccct ctctcccctg                                                    20

<210> SEQ ID NO 2
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 2
cattgatgct ggtgagag                                                      18

<210> SEQ ID NO 3
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 3
ctgaggtgga cggtcaagga cag                                                23

<210> SEQ ID NO 4
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 4
gtaggactga atagctacta atac                                               24

<210> SEQ ID NO 5
<211> LENGTH: 23
<212> TYPE: DNA
<213> ORGANISM: Artificial sequence
<220> FEATURE:
<223> OTHER INFORMATION: Single strand DNA oligonucleotide
```

```
<400> SEQUENCE: 5
ctgagatggc atacagagag tac                                              23

<210> SEQ ID NO 6
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 6
ctctgggtga gtgatttgct tg                                               22

<210> SEQ ID NO 7
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 7
cacagagctg ttacctgctt gg                                               22

<210> SEQ ID NO 8
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 8
gctctgtggt ttcattagct ttc                                              23

<210> SEQ ID NO 9
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 9
gctataaagc aaacagtgtg tac                                              23

<210> SEQ ID NO 10
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 10
caataaatct gaggaagaaa gaaatc                                           26

<210> SEQ ID NO 11
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 11
gtgcacacat ctgtaatcat atg                                              23
```

```
<210> SEQ ID NO 12
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 12
caatgggaga ggacacgaag tac                                          23

<210> SEQ ID NO 13
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 13
gaatcgacgc aaaaggacgt g                                            21

<210> SEQ ID NO 14
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 14
gaaatggcag gggacagaga c                                            21

<210> SEQ ID NO 15
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 15
gtaaaatctc aaaagcaata aagaaag                                      27

<210> SEQ ID NO 16
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 16
cagaaatgaa caggcaggca tg                                           22

<210> SEQ ID NO 17
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 17
gcaacatctc acttgtgctt g                                            21

<210> SEQ ID NO 18
<211> LENGTH: 24
<212> TYPE: DNA
<213> ORGANISM: Artificial sequence
<220> FEATURE:
<223> OTHER INFORMATION: Single strand DNA oligonucleotide
```

```
<400> SEQUENCE: 18
gatacgtgag tattttcctg ttcc                                          24

<210> SEQ ID NO 19
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 19
gatatattct cttatcacat ggg                                           23

<210> SEQ ID NO 20
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 20
ggctattgta tcgtctatca c                                             21

<210> SEQ ID NO 21
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 21
ctacagtgta tgcctagtca cag                                           23

<210> SEQ ID NO 22
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 22
ctgtctgcct ctcttcatta tg                                            22

<210> SEQ ID NO 23
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 23
ggcagttgga gattatgcct tg                                            22

<210> SEQ ID NO 24
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 24
caacatccag acatagaggc tg                                            22
```

<210> SEQ ID NO 25
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 25
ctgctctcca gtgacaactg tc                                            22

<210> SEQ ID NO 26
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 26
cgacgaggcc cagagcaaga ga                                            22

<210> SEQ ID NO 27
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 27
tccagggcga cgtagcacag ctt                                           23

<210> SEQ ID NO 28
<211> LENGTH: 633
<212> TYPE: PRT
<213> ORGANISM: Artificial sequence
<220> FEATURE:
<223> OTHER INFORMATION: Single strand DNA oligonucleotide

<400> SEQUENCE: 28

Met Ala His Leu Lys Arg Leu Val Lys Leu His Ile Lys Arg His Tyr
1               5                   10                  15

His Lys Lys Phe Trp Lys Leu Gly Ala Val Ile Phe Phe Ile Ile
            20                  25                  30

Val Leu Val Leu Met Gln Arg Glu Val Ser Val Gln Tyr Ser Lys Glu
        35                  40                  45

Glu Ser Arg Met Glu Arg Asn Met Lys Asn Lys Asn Lys Met Leu Asp
    50                  55                  60

Leu Met Leu Glu Ala Val Asn Asn Ile Lys Asp Ala Met Pro Lys Met
65                  70                  75                  80

Gln Ile Gly Ala Pro Val Arg Gln Asn Ile Asp Ala Gly Glu Arg Pro
                85                  90                  95

Cys Leu Gln Gly Tyr Tyr Thr Ala Ala Glu Leu Lys Pro Val Leu Asp
            100                 105                 110

Arg Pro Pro Gln Asp Ser Asn Ala Pro Gly Ala Ser Gly Lys Ala Phe
        115                 120                 125

Lys Thr Thr Asn Leu Ser Val Glu Glu Gln Lys Glu Lys Glu Arg Gly
    130                 135                 140

Glu Ala Lys His Cys Phe Asn Ala Phe Ala Ser Asp Arg Ile Ser Leu
145                 150                 155                 160

His Arg Asp Leu Gly Pro Asp Thr Arg Pro Pro Glu Cys Ile Glu Gln
                165                 170                 175

```
Lys Phe Lys Arg Cys Pro Pro Leu Pro Thr Thr Ser Val Ile Ile Val
            180                 185                 190

Phe His Asn Glu Ala Trp Ser Thr Leu Leu Arg Thr Val His Ser Val
        195                 200                 205

Leu Tyr Ser Ser Pro Ala Ile Leu Leu Lys Glu Ile Ile Leu Val Asp
    210                 215                 220

Asp Ala Ser Val Asp Glu Tyr Leu His Asp Lys Leu Asp Glu Tyr Val
225                 230                 235                 240

Lys Gln Phe Ser Ile Val Lys Ile Val Arg Gln Arg Glu Arg Lys Gly
                245                 250                 255

Leu Ile Thr Ala Arg Leu Leu Gly Ala Thr Val Ala Thr Ala Glu Thr
            260                 265                 270

Leu Thr Phe Leu Asp Ala His Cys Glu Cys Phe Tyr Gly Trp Leu Glu
        275                 280                 285

Pro Leu Leu Ala Arg Ile Ala Glu Asn Tyr Thr Ala Val Val Ser Pro
    290                 295                 300

Asp Ile Ala Ser Ile Asp Leu Asn Thr Phe Glu Phe Asn Lys Pro Ser
305                 310                 315                 320

Pro Tyr Gly Ser Asn His Asn Arg Gly Asn Phe Asp Trp Ser Leu Ser
                325                 330                 335

Phe Gly Trp Glu Ser Leu Pro Asp His Glu Lys Gln Arg Arg Lys Asp
            340                 345                 350

Glu Thr Tyr Pro Ile Lys Thr Pro Thr Phe Ala Gly Gly Leu Phe Ser
        355                 360                 365

Ile Ser Lys Glu Tyr Phe Glu Tyr Ile Gly Ser Tyr Asp Glu Glu Met
    370                 375                 380

Glu Ile Trp Gly Gly Glu Asn Ile Glu Met Ser Phe Arg Val Trp Gln
385                 390                 395                 400

Cys Gly Gly Gln Leu Glu Ile Met Pro Cys Ser Val Val Gly His Val
                405                 410                 415

Phe Arg Ser Lys Ser Pro His Ser Phe Pro Lys Gly Thr Gln Val Ile
            420                 425                 430

Ala Arg Asn Gln Val Arg Leu Ala Glu Val Trp Met Asp Glu Tyr Lys
        435                 440                 445

Glu Ile Phe Tyr Arg Arg Asn Thr Asp Ala Ala Lys Ile Val Lys Gln
    450                 455                 460

Lys Ala Phe Gly Asp Leu Ser Lys Arg Phe Glu Ile Lys His Arg Leu
465                 470                 475                 480

Arg Cys Lys Asn Phe Thr Trp Tyr Leu Asn Asn Ile Tyr Pro Glu Val
                485                 490                 495

Tyr Val Pro Asp Leu Asn Pro Val Ile Ser Gly Tyr Ile Lys Ser Val
            500                 505                 510

Gly Gln Pro Leu Cys Leu Asp Val Gly Glu Asn Asn Gln Gly Gly Lys
        515                 520                 525

Pro Leu Ile Met Tyr Thr Cys His Gly Leu Gly Gly Asn Gln Tyr Phe
    530                 535                 540

Glu Tyr Ser Ala Gln His Glu Ile Arg His Asn Ile Gln Lys Glu Leu
545                 550                 555                 560

Cys Leu His Ala Ala Gln Gly Leu Val Gln Leu Lys Ala Cys Thr Tyr
                565                 570                 575

Lys Gly His Lys Thr Val Val Thr Gly Glu Gln Ile Trp Glu Ile Gln
            580                 585                 590
```

-continued

| | | | | | | | | | | | |
|---|---|---|---|---|---|---|---|---|---|---|---|
|Lys|Asp|Gln|Leu|Leu|Tyr|Asn|Pro|Phe|Leu|Lys|Met|Cys|Leu|Ser|Ala|
| |595| | | |600| | | |605| | |

| | | | | | | | | | | | |
|---|---|---|---|---|---|---|---|---|---|---|---|
|Asn|Gly|Glu|His|Pro|Ser|Leu|Val|Ser|Cys|Asn|Pro|Ser|Asp|Pro|Leu|
| |610| | | |615| | | |620| | |

| | | | | | | |
|---|---|---|---|---|---|---|
|Gln|Lys|Trp|Ile|Leu|Ser|Gln|Asn|Asp|
|625| | | |630|

<210> SEQ ID NO 29
<211> LENGTH: 3874
<212> TYPE: DNA
<213> ORGANISM: Artificial sequence
<220> FEATURE:
<223> OTHER INFORMATION: Single strand DNA oligonucleotide

<400> SEQUENCE: 29

```
atggctcacc taaagcgact agtaaaatta cacattaaaa gacattacca taaaaagttc      60
tggaagcttg gtgcagtaat ttttttcttt ataatagttt tggttttaat gcaaagagaa     120
gtaagtgttc aatattccaa agaggaatca aggatggaaa ggaacatgaa aaacaaaaac     180
aagatgttgg atttaatgct agaagctgta acaatatta aggatgccat gccaaaaatg      240
caaataggag cacctgtcag gcaaaacatt gatgctggtg agagaccttg tttgcaagga     300
tattatacag cagcagaatt gaagcctgtc cttgaccgtc caccccagga ttcaaatgca     360
cctggtgctt ctggtaaagc attcaagaca accaatttaa gtgttgaaga gcaaaaggaa     420
aaggaacgtg gggaagctaa acactgcttt aatgctttcg caagtgacag gatttctttg     480
caccgagatc ttggaccaga cactcgacct cctgaatgta tgaacaaaa atttaagcgc      540 tgccctcccc tgcccaccac cagtgtcata atagttttc ataatgaagc gtggtccacg      600
ttgcttagaa ctgtccacag tgtgctctat tcttcacctg caatactgct gaaggaaatc     660
attttggtgg atgatgctag tgtagatgag tacttacatg ataaactaga tgaatatgta     720
aaacaatttt ctatagtaaa aatagtcaga caaagagaaa gaaaaggtct gatcactgct     780
cggttgctag gagcaacagt cgcaacagct gaaacgctca catttttaga tgctcactgt     840
gagtgtttct atggttggct agaaccctct gttggccagaa tagctgagaa ctacacggct     900
gtcgtaagtc cagatattgc atccatagat ctgaacacgt ttgaattcaa caaacccttct    960 ccttatggaa gtaaccataa ccgtggaaat tttgactgga gtctttcatt tggctgggag    1020
tcgcttcctg atcatgagaa gcaaagaagg aaagatgaaa cctacccaat taaaacacccc   1080 acttttgcag gaggactttt ttccatatca aaagaatatt ttgagtatat tggaagctat    1140
gatgaagaaa tggaaatctg gggaggtgaa aatatagaaa tgtctttcag agtatggcaa    1200
tgtggtgggc agttggagat tatgccttgc tctgttgttg acatgttttt tcgcagcaaa    1260
agccctcata gctttccaaa aggcactcag gtgattgcta gaaccaagt tcgccttgca     1320 gaagtctgga tggatgaata caaggaaata tttatagga gaaatacaga tgcagcaaaa    1380
attgttaaac aaaaagcatt tggtgatctt tcaaaaagat ttgaaataaa acaccgtctt    1440
cggtgtaaaa attttacatg gtatctgaac aacatttatc cagaggtgta tgtgccagac    1500
cttaatcctg ttatatctgg atacattaaa agcgttggtc agcctctatg tctggatgtt    1560
ggagaaaaca atcaaggagg caaaccatta attatgtata catgtcatgg acttggggga    1620
aaccagtact tgaatactc tgctcaacat gaaattcggc acaacatcca gaaggaatta    1680
tgtcttcatg ctgctcaagg tctcgttcag ctgaggcat gtacctacaa aggtcacaag    1740
acagttgtca ctggagagca gatatgggag atccagaagg atcaacttct atacaatcca    1800
```

```
ttcttaaaaa tgtgcctttc agcaaatgga gagcatccaa gtttagtgtc atgcaaccca    1860
tcagatccac tccaaaaatg gatacttagc caaaatgatt aagtgttcct taaaattaag    1920
ttgaaaaagg aaatattctt tctcataaaa ctgtgactag␣gcatacactg tagttttttga   1980
```
*(line 1980 as read)*
```
aaattatgca aaagcagcta aatgtaactt attccaagtg cattttttctt atttatatct   2040 ttatgtagca ctactacaga aattctgcaa gtttctgttt caaagcacaa taactagtaa    2100
taccaaagac tatttcaaaa tgtccagatg taggggaaga gatgtttaca gtatgatgaa    2160
aataattttc caagtaaagt gatgtttgtg tgttttgtac acttagggat atatatatat    2220
agctacattc acacactcac aatttaaaat atttcccta gttttttggg gggataggaa     2280
gaaagatttg ttactgtatt tttttaacta cataaaaata gatcaataaa tgtcagcatt    2340
ggcctctgtg tacaaaccaa gagcttttac agatccagaa tttattagtt taaaatgcag    2400
gtgaactttt ttttgcgttt ggtttacttg tctgtcaaat gtttccttaa acatgaaact    2460
gaataaggag aagagtattt ttaacactta aatttcttgg caaattttaa aacatttttt    2520
agtctgtaat acactccact tgaagcactt aagtcttcct taaatgactt tccttaagta    2580
atgatactgt gtgttttccc aaagcacttt taaaaaaatt tttataaatt actatctgtt    2640
gaaaaggtgt cctttttcctt tcttctagta ttttttttttct taccaaaatt cactaatctt 2700
gaatgtttgt gatattaaat ttcaaatgca gaatacttga ctcatttaaa gctaaatttt    2760
gttactgatt caattataat tgtaatggat ttttgactttt gtaatggatt cttttcatca   2820
aaaagcctta ttatttttta tctatgtgga aaacacaata aaaatcctc aacactattg     2880 taatcatttg gttaagtgct tattcctctt ttgggtaaaa tctgtaattg ataataggtg    2940
ggggaaaatg aattttgtat gctgaatttc taagcgccta ttgtttgtaa aaccatcaga   3000
tatttcttat ggcacaaaaa atgaggaata gcaaaattcc tgtgttcaat atttagaaaa    3060
ttttgtatta atttctgata aagttcctta agcatctgat agaatgatgt tttaaaaaaa    3120
tttgacgctt gcttaggaga tttaccactt ttttttttttg ttttttcgtca ttttatattt  3180 agatctcctg tattcttgtt cccgaagtaa aatacgatcg gtttcatatt ttaaatctgg    3240
cagagcctca gctgtacgaa aaagagcata tactggttat tgaccctatc ttctcattgt    3300
ttgtttgtaa gtttgaattt gtattaaaaa gcctgcattc tgagctggac atggtggctc    3360
agcttctaat cccagcactt tggtaggcaa aggtgggagg atcatttgag ctcaggagtt    3420
ccagaccagc ctgggcaaca tagcaaaatc tcatctctac aaaaagtaaa aattaaaaaa    3480
tgaaattaaa aataaaatta cctaggtgtg gtggcacgca tctgtagttc cagctataca    3540
ggaaggtgag gcagaagcat tgcttgagct tgggagatcg aggctacagt gagctatgat    3600
tacaccactg cacttcagtc tgtgtgactg agcaagactc tttcaaaaaa aaaaaaaagc    3660
ctacattctc cagttgatta tttccaacta atgtgtatta tgtgcctaat tttctatcag    3720
aagttgtatt aagcccgttt tcacactgct gttaaagaca tacctgagac tgggtaattt    3780
ataaagaaaa ataggttcaa tggacccaca ggtccgcgtg gctggggaag cttcacaatc    3840
atggcggaag gtgaaagcat gtcttacgtg gaag                                3874
```

<210> SEQ ID NO 30
<211> LENGTH: 19
<212> TYPE: DNA
<213> ORGANISM: Artificial sequence
<220> FEATURE:
<223> OTHER INFORMATION: Antisense oligonucleotide targeted against the GALNT3 mRNA

```
<400> SEQUENCE: 30
ctggcacata cacctctgg                                                    19

<210> SEQ ID NO 31
<211> LENGTH: 19
<212> TYPE: DNA
<213> ORGANISM: Artificial sequence
<220> FEATURE:
<223> OTHER INFORMATION: Allele specific probe

<400> SEQUENCE: 31
ctttgcactg agatcttgg                                                    19

<210> SEQ ID NO 32
<211> LENGTH: 19
<212> TYPE: DNA
<213> ORGANISM: Artificial sequence
<220> FEATURE:
<223> OTHER INFORMATION: Allele specific probe

<400> SEQUENCE: 32
ctttgcaccg agatcttgg                                                    19

<210> SEQ ID NO 33
<211> LENGTH: 157775
<212> TYPE: DNA
<213> ORGANISM: Homo sapiens

<400> SEQUENCE: 33
ttaaaaagat ctttaactat tataaggttc atataattaa tatagaggaa tcatccaatg         60
atacttatga agggaaaatg acctattttc cttcaccact ctgaggacct aactcagtaa        120
atgcagagga ggctgaggaa acatggaaga gacacgacct cagcaaccag ccttttctcc        180
agcgtgatca atccatctct acaaaatcag tgtataatga gatttccact tagtgactag        240
ctgattgaag gggggcctct acccaaatac tcaactaggc cttttctttttc tgaagcattt      300 tgatttgtct tgcctgggac aactagcaga acagtccaga atgcattgca tactttctaa       360
ttacctcaca ttctcttatt aaagagaaca gatagaaata aaacatgcac tccccacctt       420
tagattacct gcacttggtt cgtcggagga cttctaggat cccgtttccc tgtaaattaa       480
tttaggtaac taaatagtgt aattctgcct ttttttttcc aatgcaatat gactatgcta       540
aacctgtttc atattttga ccttctattg ttatatcact tcacatgttt tataactatt       600
tgaaatgcgg acatgacttg ctattcagtg actgcatcgc tacttatttt ttatgtcttt       660
tagacttggg tgtttagaat tatgatata aatatattgt agatctcaat ttctaaaaaa        720 aatatttat ttaattgaac ttaaaaatgc ttgatctaga gaaagtcctc cagtggaaaa         780
gtttctacta aactttgttt tggggaaaaa atgtttactt ggcagctctt ccactgtgca       840
gttggtttct gccccttctc ttcccccccta cattgggcca aatttataac tcttaatatt      900
aacattaaaa gagctttggg tttgtcttta tgtaggttgc agtaatgaga gcagggttgt       960 tcctttttgaa tgattggccc tttgggctaa tcagaatgag gatttgttga aatctcaaat    1020
atacatatat atatatatat atatatatat atatatatac acacacacac acacatacac    1080
atatatatac acatatatgt atgtgtgtgt gtgtgtgtgt gtgtgtgtat atatatatat    1140
cccatgttgt ctgcaaagtg acagttttta gtgcttaatc tccaaaattt tcccctact     1200 gatacaatct aaagagcaca ggcccaaaga gaaaatgaca agaggctatt gttccttcat    1260
tcaagcacat gaaaggatca tgtgtactgt atttgctgga ccattacaag ctcttgaagg    1320
```

```
atctgcttgt gaagtactct gaggttattc ttggaacaca gagtgtggga gagtggggaa    1380
gagccagctc cagcctgagc aaagctgaag ggtagaatga cagtccagtt tctgaaaaga    1440
gatattttaa ttttagttca gctttatttt cctaagacga tatgaagcct actttttat    1500 ttttggctag gtctttgttt tctagctttg tttccaaaag gatgcttaag aaaacagagt    1560 tttttttcccc tatccatttta tctagggtag aaagtcactg ccctgtgaga agaattaccc    1620
ttccaatcat gacagcttct attccaactt ttcatatacc tgactaacct gtaaacatat    1680
cccacaaacc acatacacag gctacctatt aaaactctcc catataccta acacatacac    1740
atgcacacac atacaaaata tatacatatc acacacttag agaatgacag atttcaggca    1800
atggccaata gtcagtattg agttttctaa accccagaat ctggttgggc tttatgatct    1860
aaaaaaatgt ggtttagaaa agaggataat tggtagagct gtagtttgaa aatatcaggt    1920
caaagttgca aacatactta tgatggaatc atttcatttt tagttccttt cccagaaaag    1980
ctgagagagc acactgttcc agctgacttt tttttccatt aatagccgtt ctattcaaca    2040
aagagctgcc cacatgccag gaaagtgcta cagtccttct aagcttttaa aaatggggat    2100
caagctacat gcagccagtt ggaatactta agatctttat gccaagacac aataacctga    2160
cctgcagctg ttgtattgcc tccatagtat atctagccaa actgtagtct tgacacaca    2220 acttttagt cattcactat caattgcaaa gcttcatgct ccagccctgg ctattctagt    2280
accagtccta tacctttaaa tgggacttaa ttcccagtta taatcctggc cgaattgatt    2340
tgaaagtcaa gtggctgaag cagcttgcat ctccttttgtc attcccaatt tcctttggga    2400
gaagtcaatg aaagagattt acttaagttt ttcctcctta tctcttgatc attaattatt    2460
aagacatggg taaaattcat ttgtctcatg tcttttggtt gattgaataa tatagttact    2520
ttttgaaagc ccatcatttc tttgtgataa aaccatttc tcaatgtgac agccacatgt    2580
aaaatgtgaa actaatgttt cttagtatgt ttaaaatctt cacaatcata tatggccctg    2640
caatactccc tgaattcctt ccctccaaaa aaaaactatg agttgcaaaa acactagtta    2700
cgaattaatc aagaagcaaa gagagtatgt taagtggcta tgttctttaa aattttacat    2760
tctaatagat gacttctagg caaaattttg gtatgattac cattaaacag gaaaacatac    2820
catgatttac tttctataac ttgctaatca ctgtttcttt tatttcaatt tttgatattg    2880
ttgcacaagt ttatgactct ttggtcttta tattcaaaat ttattaagta tcaattcttt    2940
ctttcaacaa atatgtactg aacacatgct gtgttagaac aactgtcttg ggtagtaaaa    3000 agagggaac actacaaatt ataatggata atattaatga agggtggcat gaaataatca    3060
agctttctca aatcctctta atatgtgatt ttatcaagtg acattagaaa aactgacatc    3120
agttcttgtc taattatatg tgagctgcaa ctaaaagatg cttcctttac ctaaattata    3180
gaactcactg gatcgccctt catctctctc cctccatctg aaatgtatga attaaatcag    3240
gactcagcta ggactgaatc aaatgaaaaa gaaattttcg attaattgct tcttcaatgt    3300
tagacctata taagtgatgc taaatttaca ccagcaaact cctatcagac agtttcaagg    3360
aggatttgac tcatgcataa cccaggaaac atttcaggaa acttttaaga caacagtgtg    3420
gaacacaatc actcttactt ctatttataa aaagcctatc aaaacagcaa atcctgttg    3480 caaattccaa agacatcact ttgcagcagg tggaaaacag agaggttgtt agactccatc    3540
actttcagct ggagttacaa accatcaaat tagcaggtgg aaaatttata ttctcagaag    3600
ccaacaggag actgcctttt taaaaggtgt catgaagcct tctatttctc caaacaactc    3660
aatatttctc tttaaaatgg catctctgtt ccttattctc ttgatgacag tttgcagtgc    3720
```

-continued

```
cattatagcc agtgtattaa ataccaggct ttaatgggaa gcacctttgt gctttcaaag    3780
gcaagacttg tctgtaattt taaattagaa ctgttggttg tattcttacc acaaccaaaa    3840
cccaaagttt aaaggcttga ttactctata ttaggtctaa tatgaatttt caccttctga    3900
ttgcattact ttttctgaaa tctgctaact agtgctggaa taacaaaaat gcctaagcca    3960
aaatgctgta gctctgcacc aacagcacag ctcatcagat gttttctata gtagtaaaga    4020
atttgattga cttaattgaa tatcagcaat tttaataccc actagaatta tggaagtatc    4080
agagtggaag tgaggacgca ataaaagctt aataagtggt ggtgtcttct aggaattatg    4140
aaaaaaaaag ctcagcagag ctaagccaga tcttattaca tcataaagac tagagttaca    4200
aatggcagcc ccaaacctag aaggggcagt tacaatgtgg acacccttc agcccagttg    4260 gtgctcacat ctgctgacca acattcatat caattacatt tttacagtct gtaagtcatt    4320
tgatgcttta gaaaataaaa acacacacct acagcattct aaagaaacta ttttgttaaa    4380
aaatttaaac acattttata ttaaaataag tgatcaatga ctttcatgat tgtcaaaagt    4440
aaaaagtgca gacatttaaa aaagctcttc tttcacattt tacctaccaa atctagatat    4500
tcaacgtgag tccttaaaac agtcacttct aaatttatt ttgactcctt tcttggcttt    4560
ttcaaactgg accatgagac ccccttccta acaatgcag ttgttttgtt ttattcttt    4620 tttccagaaa ttcaagctga aacatttgat atgacctgtg ttttacctgg tgatcagttc    4680
tcaggctagt ctaagtctgt gctgtcttgg catgccttgg gtttcctatc ctgagagtgg    4740
taatgccagt agaatgatgg gaaccaggag agtgaatacg accagattca aagcctaaaa    4800
caatatgttt cagtttactt ttatatgtag attttttaaa tattcacatc tagcctggaa    4860
ttttagtaaa tacagatact tgttgtatcc atgggaaatg aggtcatttc aaagatgtaa    4920
gtcacgttgg tgactacttt cttttacttg tgataaatat atcactatac agggtaattg    4980
cttttataaa tttgatcctt tgcattggct tataattcaa gaaatgtcaa cttcactgtg    5040
tcactttatg tcatctctca taaaagtttc tggcaggact aaagtttcaa aggaatgtga    5100
tagaatttat tttggataac atttgtattc agcatgctaa tgatgtaact cctctcttta    5160
tcattaccac ggtgatagtt aagttcattc gttaactcat tttagtgaca tgtgaggcca    5220
tttaaatatt tttaagataa tgtatattga ttagaaaggg ttagaaggag acaaatttat    5280
ggtagaaatt agccttgcca ttgtctaagt taatttatgt gacctgattg aacagtttta    5340
gttgtaactt tagagtagct tctttgttag aggatctctt tcctttctct tttggttttc    5400
tcccaatatt tttatctgtc ttgggattat cttaaaaggt atttattaat gagtatttgg    5460
aagaaaattg acctagaaaa tgtctctttt aaatttatct aggtacttgt atcaccagag    5520
accttcatca agtcctactg ccacactgga taaggccact acccccgacc cttcttgtca    5580
gggacatggc ttcctaataa tggttttgct gttgtctcta catagggggac ctatggaaaa    5640 ggagtttgaa atttctacct ttgtagtaca ttgtatccaa ttttgtttg ctcctccttt    5700 tcatgtggtc accaagcttt tttccttagc cattaaaaaa gccacccctc tttaaaacaa    5760
atttaaagat ctatatacat ttttgcaact ttatttaata aaaagagaa gaaaaaataa    5820 aatctaaatc tcaattaccc taaagtggaa aaacctaagt atctaaccta ggaacttgtt    5880
gcctggtggt ggttgttgtt gttgttgttt ttaatttat ttagtgttga tccttgagtt    5940
atttaatggt atccaaatga tatctgaaag tgattgattt taagatgtaa tagttggcaa    6000
agtcatttca tttgtgtctc aaacaaataa agcccactgc catgggttac catctgaacc    6060
ctgattcatt aggcactagt catgccaaat ggggatctca gaatagttta atcttttcaa    6120
```

```
agatactcac aatggccaac tgtgtgtgaa tactggaaag tttgagattc ttctatattc   6180
ttcaaattta tggtcctgag actaggaggg atctccagag gtcatatggc tcatcgatct   6240
accaccaggg aagactgtca cttaggcatg cccaacagga gagatcgcca tctattctta   6300
acatctctag ggaaggcagt ttccttggca acacaattca gctctcttag gttttctcac   6360
aataagaaaa tatcttggcc agtctttgag ggttaggcac ctggcaacag ttgtggtgat   6420
ttgggccatt gtactagggg attcaaggga agttgggttt cccctacat ttggtgatta    6480 ttacattaat atatgatcat tccataagtc tcctaagaaa tcagattttt aaagaaagac   6540
acggattcag agacaatggt ctgtaacatg accaactttt gacaaatatg gctgtactag   6600
gttttcattt ttgctgttgt tgttgtttgt ttttgtgatt gctcttatgt cggtaggtaa   6660
tgtcaggaaa agtgactgtt tcagatcccc agtacaaaca tcagaactag gatcaaatga   6720
cttgactttt aagctgttcc attttctaag aagttacaat tacaaaaagt aagcattttc   6780
tacattctta cttctaagta atgaccttct cattaatctt tccttggctt aaaatgacaa   6840
ataagaatcc aaagtttttc cactcctcct gtgggagata ggaatagttg tgaagagtct   6900
gatggaataa aatgactcca gagatttaca cagccaccat ttgatcccag cctttgtcct   6960
tgtgttattt aaacaatggc ttcctgcttt ctcagggtc aggaaaatga tttaaaaatt    7020
tgtcttcttg acaaggcctg aaaacgaagg gaggtgtcgt ggagaaatgg tgattttttct  7080 ggttacatca cttgattcaa gcactccctg gagctttcaa agcctttttt atctgctcag   7140
agttgacacc caactcagag tcagaactca ccagaagatg aggaacaccc ccgaaatcaa   7200
tgtttccttt ctccatggga tttttttcaa tcttggtaca gctgcatatc tcccaaactc   7260
ggatgctctt gtgaaatgac agccacatca gtgtggttac tccccacaaa taacactagg   7320
gggaaatgac ctttttatt taaaaaaaa aaaaggcta atgctataga atgatcatgt       7380
aaagaatgtt gaataaaatt tggcccatgt tttaattgac tctaggcacc tctattgaaa   7440
taagtctgag gcatagtttg tgaaacatgt ttcaaaagtg tttgatgtat aataaatgct   7500
agaaatttac agtacagaaa tagtaaaaaa ataaaataaa aataaacctg tagattacag   7560
ctctgttcct aagaacctca gcctttattg tgtcttagta aagttgatct gctttatttt   7620
tagtttattg aatttctggt gtactagcct cttaagatag aactttaat acatatgtac     7680 tggttaatgc ctgtttacgc agaaaatggc actttgttct ttcagtgtgt ttccctcagt   7740
gtcacagggt atatcaattt gatagatcat ttgacatttg tcaaaaatac gtttcccatt   7800
ttaaaaatat gtataattgg ttgcatagac atatgtcact ttttgcagtg tcttcatctt   7860
gatcatagtt ttagacatca actatgtctc actttccaac tgccatagaa atttggtaca   7920
tttgcaaatt ctggtggaat ctagtgagct gaatgtattg gtagatcaaa tgatccaaag   7980
gacttgggtg ttatccttca gtctgtgttg aaccattcag atattgggaa tggtccttac   8040
acaagggaag tcttttgaga atatttgttc tcttattttt tgtttgtttg ttgctggcaa   8100 aaaaaaagt aacttaaaa actcagaaaa gccactgaac tgtattttgt gaccttatga     8160 ttagtttat ctttcaactg attttattg ttacttttac tcaatatcaa cagtacttca     8220
atagatattt attagttatg ttcaatctaa tgacttaaaa cagttgaaaa ggaggaaaat   8280
caactccagt ccacacatac agtcatgtta cattaagatg tcatgttgta tgtcacacag   8340
tttctagatt gatttctctt gtgtataagt tataacatca aaaatgccaa agggtatata   8400
aaataagcta caataatatt caacagaact taacctggac cttatgttgt aataatttat   8460
tcatattagc tgtagtcttc tgtatttata ttttcagtat ttattatgaa tgacatggaa   8520
```

```
attcgtgtat ttattgtggc tttttattgc agtgtgtata tatatataac aaataagcat    8580
ttttaagtct tatccttaag tttcttttat tagtggcact tgtattatgc tgtacttttt    8640
attacatatt gtacaatatc ttgtccattt gtttgcagca gagtaaaacc ggtttctaag    8700
ttgtatctac tgttgcattt ctgttgcctg ttgtgtaaaa cctttgttct tacatcctga    8760
actgcaatcc gttacgctgt cccagcacac acaaggatac ctcccttcca ctgtgtaaca    8820
gataatattc ttgaaaagtt gtgtgtgaag tcagttcctg tgaaatggtt cattacattg    8880
tcatttcaaa tatgtgttaa ctttattggg atttatccct aagtgaagat gcttatagca    8940
cttttacttc tcagctattc aacccctca tcaagtgatg atgtgtaaac aaacacaagg    9000
gccagaggag aactctttat gtaaatgaaa tttggaggct attttacaa ggacaaattc     9060 aatctcttgt aagtagtatc ctttcactta actgcttagt agtatttttg ttttgctttg    9120
cttaaagcag aatctgtgtg atttgatgtt tagaatatat gcgtgtgcat ggtacgtata    9180
tgtgcccaac tgtttaaagc tactggctta aggtaactaa aacttaactt ttattggcag    9240
taggatgaag gaaaaaaaat tgcattttt taaatctcct atcatatcca agacactttc     9300
ttccaacaac ttgttttata tttagagact ggatctatat ttttaaaagc aaataataat    9360
atgtgatttt gtgatcatcc taaaactcaa atttgaacat gttattcact gaattaaaca    9420
tattttgtgg tgttccctcc tcactgccaa caaaacaaaa ttcagactcc ttggaatgcc    9480
tcacaaggtc gcctgagatc tgggtacaag ctctcccttt acttcccacg tcttctgctg    9540
cccacaagag cggttcctta gatttcacct gctagtccat tttccctgct tctgttcagc    9600
ttgtctcttc tgccaagaat atacacccca taaacctatc ccgacagcac aattctagtg    9660
accatctatt tatttatcaa gagaaaacac aaatattctt tcctttatgt tgcccttcca    9720
atactcctga aaatcgtttg cctgttgttt tatgcaaagc agacatgtat tagagcccct    9780
tcgagtctca ctgcactagc ttatttatgc atctactccg cctcagtact tcctgagaac    9840
agaaaacact tctcattact ctgtcttctc agcattcagt ttagtgttta aaacatggta    9900
gagacttaaa atacatttac tgatgtatgc aaagtaaaaa attgagtgat gcaaagtcca    9960
ctcctgtata ggagttcaga tgagggaaag atgattggct gaaacagtgg aaaaggtgtc   10020
agattcagag agagggagaa tttcagctag cagggttacc cccatagtcc acattatgga   10080
acaatttgag gaaaggctga tcagaacaac atcactcttc tggtgggggg cagaaggacc   10140
tggttaagaa cagataattt actatcaaga acaaatgaca aatcaggtta ggagagtgca   10200
tttagacagt gcaaagcttt gaagaccaac ccaaggaatc tggctcatat ccttagggaa   10260
ataaggatat ttccttcagg aaatcctgaa gattttagaa aaggaaaatc aatcaaataa   10320
gagtgatttg cagtatggaa tatcagtgtg gctacagtgc acagacagtt tgggaggatg   10380
gaaatgccag aggaaaaatc tttgcagtag ctattgcagt cagtattcat tagaaaaaat   10440
aagagttaag aacctactct gatttaggat actgtgcaag aatgtgctac aatgaggagg   10500
gtgtggggga aaagacaggc agagtccctc tagacaagca agtagaaaga tgtgggtaat   10560
tacagcagag aaaaagtcag ctatttgaaa gcctattacg atgtgagaga ttaaaggtaa   10620
caaaataatt atgagcctaa aataccatag gtggaatatg gggaaggaca taagaagata   10680
aatatcatca acataaatta gaatgttata aggaggaaga gatgtgttca ttttggacag   10740
cttgaattga tgctgggata ctcagtgaaa ataacaaatg gacggaagga aatgtaagtc   10800
tagagcttag acaaagacgt aagatttgga gcgaatgaga attttaagaa gagaaatatac  10860 atatatatat atagaaggaa ctaaataaca gacaggactg aagctttaga aaggctagtg   10920
```

```
tttcaggttg tgtttgctgt aagcacacaa ttctgagatg gagtttagca tgcaggattt   10980
ccatgaggaa tcaattcttg tgggagctag cgggaggaag cagattagga aaagacagaa   11040
atcaggctgt gatgcggacc gaccccactg gagtgctcta gaggataagg gatcctctga   11100
gtcatcccct cgcgggctga aatggctggg cctttatagc cacgccacag tcagtctctg   11160
gatgtcttcc accccagaaa gggagtgctc tcagatgagt tggcaccctg cagtgaggag   11220
aaagcctgaa aagagctgag agctggagga tgtttttctg acagcgctct taggacctgg   11280
gacaagtcct tccttgaaag ggaattttttg aaggtaaaac agctctgtgt cttctacatc   11340
catccctcag gtcctcagat tcatgtcatc acttaaattt cagggaacag ctccttcagg   11400
attctggtgg gcctctctcc ctggggaaa acttaaagga gcaaggttag taaaataaat    11460
tacagttcct gccactctgg ctggtcctaa agccacaact aaaactgacc atctccctct   11520
ctcactatta attctacatt cttctcagct tcatcaaaca cagttgctag cctcaatggc   11580
ttacttggtg gtgtgaccca gagccaaaag gcacctaagt gaatattact tcctgctcct   11640
attatgaaac agtaggccca tctcttcctg aggatcaagg tcaaatacct ctaccaagat   11700
ggtgaggtat ttttttctcct tgcctaaaaa tcctaggatg tagcaatagc ttaagtccaa   11760
tgggactctt tagtcccctg ataaaaatgt gacctctttg gggactagga cctttaagac   11820
tgcaaagaca tttaacccta tagagttgtg gaataggaag cacagttttc tccagtgggt   11880
catgttaagt agagacattc ctgcttccac ccagtagagt ttgcacccat gtgttcttcc   11940
tatgggggac atattattat gtaaaggttt tttattcaat ctatatactg gatcctggag   12000
gatagtaacg aattcatgcg gaacatcatc tccaaacttg cacttcaact gcaccttcta   12060
caggccagtc aacgctctgt caggccggga gctttgaagt ctatgatatg atcagtgggt   12120
ctcatggtca tgtgcccatg ctctgatatg atgttatgtg ggatcccatg tgagcagatc   12180
aaatatactg ttagtccttg aataacggtg tttgccaagg ccctgcaggt aagaatggca   12240
aacttatact tggaatatat gtctattttt atttaaaaca aacaacaaat aaaaacacaa   12300
aaaatctctg gccctttttaa gatggaaggg gcccaatgta atcaatctgc caacaagtgt   12360
ctggttaggc tccagaagaa tagtgccata tggagggctc agcatcagtc tctgttgctg   12420
gcagactgta catttggcag cagcaggagc tttatcagtc ttggtaagtg caggccatg    12480 ctcatggacc caagaagagc cttcgtggct cccactgcca cccaatccat gtacctatca   12540
cagcagccct ggagtagcca ataactgagg ctggctgctt gctgccaacc ggccaagtta   12600
ttctgtctat atcaatacta tcaaaaaata tatataatgt gagctacaaa tgtgagctgc   12660
atatgtaatt ttaagtgttc tcatagccaa cttaaaaaga gttaacaaaa agataaaatt   12720
aatttaatga tatatttcac ttaacccaat atataaaaaa tttcaacatg taatcaatat   12780
aaaaattatt agtaatattt tacatacttt ttggaagact aagtctttga aatccagtgt   12840
gtattttgca attacagcac atttcaattt ggagtagcca cgtgtggcta gtgcatacaa   12900
tattggacaa cacaggtcca caccattgtt taatatgtct tctgcagtgg gtgctctcta   12960
gttgataggt gttaacatgt gacacaaaga tcttcacact ttgtgtccac tctcacatgt   13020
cattcacatg cttatactcc aagactccta ttccccaatc ttctgatatc tctgctttca   13080
gcatcctgag ccaggctatt cacttctacc caccagtcca tatatattct aacagagctc   13140
ctatttattc ttccacacaa agagaataac cgggtggacc ttaaagctct acctatttta   13200 aggattttttc tctagcccca tgagctactc ctgaacaagg ctgcagtgta gctgccatgc   13260 attttttggct tgtttggcat ccacctacta aaccagccca tctataaacc aaatctgaag   13320
```

```
gcttttttcct cctccagcag tgagccatgt ggcatcctcc atatggagtg agggatgagc   13380
tgtggaagag gttcagggac aacagtggca aatgacatgg aagatgggac tgtcttgtca   13440
tgcagctttt tttgtgtctt ccagtccaat ttatgctcaa cccaagtttt ctacttctag   13500
aatccatctc ttaaagttct gctagccctg ccttaagata cgtggttcta caggtgcagt   13560
gccttggtgt cccatagcag gcacataatc tccatgaggc ttcagtaata tatcaggagt   13620
tgtttctcaa aaggcataca aataactgct acagatggca aagctttaat cccatagcct   13680
atgttgggat tctaccactg gcacttgaca taacctccac acagcatctt ttcccaccac   13740
tgctaccact aatatcacgg tgtctgctgg cctacatgac ccaacaacag ggcttggtgg   13800 actgcaaacca atacctccta ctgagatttt tcctgctcta cgtctcactc aaagctggca   13860
gccttttaca ttgcacaaca tacgggtcag agcagtattc ctgaatgaga aatacgttat   13920
caaatctaga acctgaagaa gcttaccaag tgttgtgctt ctcttttcat ggtgggagtt   13980
gcagcatgta ataatgtatc tttactatgg aagagacaac ctgaactccc cacaccacag   14040
aatccctgaa gactatatta gtgtggcagc ctccgacctc ttcaaagggt ttatctccta   14100
tcctccattt tgtgtgtgtt tcaccaatgc caccggcatg ctgacaagtt attgctcatc   14160
tggcctaatt agcatagtat cataaaggag tggtattctg ttggaaatct agagagttga   14220
gatctctttg tgctatatta tgacagaata caaaactaaa tatatattgt tgcctattcc   14280
acgcacatgc aaacaatttc tgatcctctt tttctaattg gaatagaaag aaagacattt   14340
gccattcaca tgacctcatc catgttactg aggttggtta acccactcta gcaaagatac   14400
tacatctggc acagcaactg cagttgaggc taccaattaa ttgaatttgc aataatctac   14460
tctcatttcc caggatctct gtgttctgca agagcaagtc actgcattaa gacaacttaa   14520
gtggggatat gatagcaacc accaccctta tatcttttag gttcctaaag gtactaataa   14580
tttccactat tccccatgcg atacaacttg tattttattt actaccttga tttgggtggg   14640
ggatatgaac agtttcagaa acatccactt ggctctcccc acttctatag cctctgtccc   14700
actcactaaa ggttcagtgt tgggattgca tgtattccaa acatgagaac ttcaattacg   14760
tacttggaac cagggaaaat gaccactgtg tgggtcctca gacctagtgg acttactgca   14820
agccagatct ctgccaggag tctgtttttt tacctggttc ttatatgctc ccactttaga   14880
acaggagggc cccatggtaa ggcttcagtt ctccaggtat caatgtccac tcagacccag   14940
tgtcaaacag tcctaaaatg ttttgagtgt ttcccttttcc cttgtacaaa gtcacccaag   15000
taaacagttg taggtacttt taaagatgga ctggggggaat catcatcata atacttgcac   15060
tgtgtagctg ggtctttctt cctagggacc tggccatttc tttagtcagt gggtcctggg   15120
tctgaaaact aactcagatc tggaaagtgg gcaaaagact acaacatctt attggcatga   15180
ctgccttatt ggagtgagtt ccttcaataa ttagggcttc taattattta ccctaatttc   15240
tcgtgatggt ataaaccaaa gtatccttgt tggctgccca tctatttagt ccctagggtt   15300
atgagtttct attaaccatc tccatgactg tctgtgggtc aggccccatt ggctgccact   15360
ctggctctgc tgctcattat gataattgca tccacctgct tttcagcagt tatgtggcac   15420
ctcctgttct ctgttgtttc agggtctttt catttccatt ggattatttg tgcctcagta   15480
ccatcagtga tggagttcac attactagcc aagtgacaaa tgataaagct tcaaaattta   15540
tcttatcaac ttcattttttg gactattctg ataccaaatg tcagattggg ttttttaaaga   15600 ctctaaaatg gagttggact tgcaagatat ttatgaaggt tcaacagctg tggaagccaa   15660
gaggaggaag caatcaaaca gagagacaag atgaattatg aagcaggcgt gacagagcct   15720
```

```
cagcccaacc ctcagagaac tccagagcca tatgacccett tggagttgtc ccctagtgag   15780
ccaaaatttt cagatcttta tatgtcctcc atggtcagtc attggatatg gatagctaag   15840
gaaggttggg cttttgaaca aggcatcact ctgcaactga ggtcatctct gaaaaagaag   15900
taacaagtca gccctgaaag aaacctgagt ggtgcatctc catatccatc acagccagat   15960
ttgggattca aaagaagaaa ataaagacat gattttgtat ccaagagaat ccagagtagg   16020
agttaagaga gcaatggaaa gtcttgagct cgggttttaa aaaggaacat gtgtatttac   16080
cagatcagga attttccttc ctgaaaatca gatcacacat ggaataccaa gttcaattat   16140
ggctactgca gtttaaaagg aatatccact tactgaaatg tgttcagagg agaatgatca   16200
aaacagtaaa ggagctaaaa aacacaacaa agggctagtt aaaggaatga atgcttacac   16260
agaatacaag ttttctttag acagctaaag gggcttgaaa ttattccctg tggaatcaag   16320
agacaaaagt ctaggaaaac agaagttaga agtctaggaa gacagaatat agggaagata   16380
attttaatat taaaaccaaa agaaaaagta ctgtagatat aaattagcca gatgaagggg   16440
aaaagaggca ttttggatca aagcagccat cacaggcaac cgtgaaaagt tcagactggc   16500
caaatataag accaatagaa agtggccgga agggaaaatg actatgaagt caatgtcaga   16560
tcatcaagtt ccttgtatct catgcttagg actttggcta ttatgcagtg aagtagtgcc   16620
tggcttggca cttcaaaagg tgaatctgac agcaaggaag ataatggatt agggagaggc   16680
atgagataga aagcaggtaa accaattaag ggtagctatg atcaatagaa ttcatgtctg   16740
tctttctgct cattgtattt gcagtacctg gcattgaacc ttcatataaa agaccctcaa   16800
taaatatcaa atagatgaat gttcgaggaa agtaccaacg gttgtctgaa ctaagccaat   16860
ggctatggga atacagaggg gttaacattc aaaagatctg tagaaggtgg aatggaaatt   16920
aaaggagagg aagaagtcaa ggataataga tttgttgatt tgttcctagt ggcatacctg   16980
ctgtggacct gaaatactga aggaaaagtg gtcggtgggc aggtgaaggg aaggaaaaaa   17040
agattgctaa aggtctcatt tatcatctat gattaggctc tatctgttgc tgaaattcct   17100
caacaaagtc tctactaatg tgcttctcc tcgatgtttt ctatgcacaa gttccccgtg   17160
attaccagca ccctgtcagt atagaacagc ctgtttcttt gcttttctct ggtaaagcaa   17220
agcagcaagc caattactga gatcattcag atgaaaattt tacttttgcc tgaattagcc   17280
agagaattga agcataaatg gaccttttca cttgactgat tgagataatt gcctcacttt   17340
tctaggggag acctatagct gggaggctgt atttggtcac caaaacatgt ttgtaatata   17400
cattattgac tttcttgaaa caactctggt tggctaggtg ccacactcaa acacttgccc   17460 tcatctttt aggtatttga aacaatacag agaaatacca tgcctcggaa actcagtgtt   17520
gaattatttc attcttgggc agcctttaaa cacatcagct caggcctcca gaagaggtaa   17580
agtggcacct aggggagtct gggagaaggc ggcagggcag gagcttggtt cagtggataa   17640
aatgcaagaa gtgagaatta gctccaggtg catgggaaca aatggctttt cctgaaagaa   17700
ttgggtaggt agacttgaaa gaaacatgta atttacattt actattggga ggggtgagag   17760
gggttaataa agagagctga gtaggggcag acaattaaag cagcagcagg gctcagatca   17820
gagccttttg gcctggatct tgggtaatag aagcattttc taacagcatg agacatggga   17880
aaagaaggct tctaaagaaa cagcacagca tctgagcttt tctgcagctt ttgctatctg   17940
gtggcctgct atgacagcct gggtgtgtac agacaatgtg tggtcagtac tgacctacaa   18000
aattcactga aaagcaagat gtgtattaga aaaactcgta caaacttcaa gtctatgagg   18060
aaaggttgtc atgtaaatgt gtctgtaatt actttgtgat ggctcccctt actggccaac   18120
```

```
gggcagaacg tcctagatcc tgaagagaag taggaggagg taacgctgag gcaacctggt   18180
taatttctaa gtttcctgta ttaaaatata tatatatata tatatatatg tgtgtgtgtg   18240
tgtgtgtgtg tgtgtgtgtg tgtgtgtgtt gctaaaataa attttattat aaacttattt   18300
tattaaaata gttttatttt tctgagtatc aaataaaaac agaaatccca gccatgatat   18360
ttataaaatc caccagtatt attttttaaat tttttatatt tatttatctt cagtgggtgt   18420
ttagagtctg cgtatggttt tgtgactata aaaaatatgc ctgctttaat ttttcaattt   18480
ttaaactttt atattacata taatttcaaa agcaatttga ggtgatggat gagacatacc   18540
cacacatcag gattgatata tccaaacaag ctgcattttg gggagagatt atatgcttac   18600
aataaggagg ttttcattgt ttaaagcaac cttgattttt tttgcattgt ttcattgttt   18660
ggaatattgc tttaactgtg gcaaatagat atacattaaa agtatattca acatcttgta   18720
atatccatag atcattcaga atcaactatg ttgaactagt tgaactagaa aagttaaaat   18780
gttgtatcca aaataataaa aatgatgcac ctatcttcta aacttttccc caggattccc   18840
aaagaataat cttaaaaatg tcaataatg ttcccacagg ctatgtatgt tgctgtttat   18900
ttaaatataa gtactgggat atttttatttt aaagatgttt tgtttgttaa tatctcttta   18960
taggtgtcat aaatattttt atgtatataa aaattggtct aagaggacca attgaattgc   19020
tagtatcaga ccattttttt gctttaatat aaacccagac tgacatatct tgtttacaaa   19080
caaataatat tggcatgaaa aaagtcacac cattacacag attttttatt taagctgatc   19140
ctgcaataga taggatactc ttgaaattag cactttacat taaaataatt aattttcttc   19200
agattttaaa aattctttct gtactttttt tcatatatgc acagtattag aagattctaa   19260
atttgttgct gtagtaacaa aaaccccctcc aaacctcaat ggcttaaaac atggtttcac   19320
tccatgtctg tcttcagtgg gtgaggtacg ccatcatcct ttttcaggtg ctaagactga   19380
tggagcctcc accatctgca acattgcagg caggggagg aaatcagctt cttgtgccct   19440
gcttcttaaa ggtttctaac tggaaataac acatgtcact tccgctcaca ttgcactggc   19500
caaaataagt tacatggaca gaaatagaac tgcattttac ttccttttgt cttaattgat   19560
cccatcaaag atgctttaat cttttcagaga aaaaaaaaga aatttgggtc atgctgtcct   19620
acaatgtgtt tggaaggaga acagaaacat tgctgaacag caccaataac tcccacattc   19680
accctaactg aggaacttta tcttaatgcc gggaaagggg acagtgcttt cacagctgag   19740
aatccaaaat agtgacagga tgtagggaaa cttatatttt gatttctttt ttaacagaaa   19800
gaggcctaac attatatttg ctggttaggt ttaatgtctg aacttctttt caagtcttac   19860
tttttactac aataaattgt gcttaaattg agctctctgg ggattccaca gggattgatc   19920
gatttgcctg gttagggctt tcaggatgg atgtcaggag tggggcaatg gcatgagaac   19980
agctgttttc agggctctgg cctcaatctt gagcgttgcc atagtgacag ctgcccgcag   20040
gaacccaccg ggagcccagt aggagaactg gctgccagag ctttgtatca gtgtgccatc   20100
cccagccttt cagaaacaag cgtaatgaac tctttagcca gggtgtttct gcctactaac   20160
ctaagggaca gtttattctt gcttgaattg tcaactgcca gatgtcagtt caggcaaatc   20220
aactctattc cctctttcct cctgtaccct ttctctcagc ttattttcat atcaaattcc   20280
acttttcccc attttatagc tacataatta acagctatta atagagcaaa ttcaattcat   20340
aaatttagat ataacaaaaa aatccaaaga tacaaagtcc tctaacacag cactgcccaa   20400
tagaattttc tgtgatgata taaatgtttc atatctatgc tgttcaatac agtagccact   20460
ggtcaccaag tggcaactca gcatttgaaa tgtggccagt gcaactgagt aaccaaatta   20520
```

```
tttaactgat ttaatttgag ttcattttaa ttttaaatag ctacacgtgg ctaggactaa    20580
tgtattgagc aacacggttc tagaatcgta ttcaaatcca gggagtggta ccagctagag    20640
ctggccaggg aggagtcaca gttagcagca ttctctcatt caaagtagcg tgtttattat    20700
ctgctctaga gcatattatt attattgctg tataaggtgt gccctggcct gccctaactg    20760
gctgttgtaa atttaattat gtagctaaag aggaggaaac ggaggcatga ttatctgggc    20820
cgttacaggc aatatcctct agaagcaaga ttgaaaggga aaaggtgtta ctatttctga    20880
ataatatatc agccacatta cagtgattct acaaaagaac tggattctaa ctggaagtca    20940
tcaattctag tcccaaattt tatgctagta aattgtatta cttaggaagg acactcagtg    21000
ggaggcttgt gtgtgtgtgt gtgtgtgtgt gtgtgtgtgt gtgtggcttt atttatttat    21060
ttttgcctaa attcctcctc tgtataaaag ggagcgtaat aatattctct gtgtgcttat    21120
taatatgaca ggggctttat gtaagtctca tttattcctt ttaagaaatc cataaattag    21180
ggatttgtat gcagagtata tagatgagga aactgaagct tagcagagtt aagtgcctaa    21240
gatttcccag ctaataattg gaagaatcaa aattcattca aactcaagtc tgtctgtctc    21300
taaaacccaa tttctttcta ctaaatccca ttagaatgtt tctaaaatcc cttctaactc    21360
ttaatcatca ctaagtgagt gccatgtaat aaatatattg aatgagtttt gcgtacaacc    21420
caaaatagga ttcttaactg tatttcattt tttaaaacat agtaacaact gtaactacta    21480
gttatttcct aacctggaac cacttaggat ttcctaatca gtggctttct cccctggctt    21540
tgcattagaa ttatttggag agttttttaa aaataccgat acgaggtatt cttctcaaat    21600
aacttaaatc acaatctgca caatggggcc tagagacagt ttttttcttg gttgttttgg    21660
gtttgtttgt tttgaggag ttttttgttt tgttttgttt tgtttgagac agggtctcac    21720
tccatcaccc aggttggagt gcagtggcat gatcatagct cactgcagcc tcagcctgct    21780
gggctcaagc aatcctccca tgtcagcctc ccgagtagct aggactacag gcatgcacca    21840
ccatgctcag ctaattttaa aatttgctag cgatggcttc tcactctgct gctaaggctg    21900
gtctcaaact tctggcctcc agacatcctt ccaccttggc ttcccaaagt cctggaatta    21960
caaatgcgag ccaccatatc cagccaggat aatttgtttt taagtctctt atatgatctc    22020
aaagtgcagg ttgtgctgag aaccgttttcc ctaatgtaag gtgtagaaat ctacttttcc    22080
attgagccac ctgctaggac ttcaggacct ggcctccagg aggaagcccc ctgatagctt    22140
ggttgatttt atcttatcag tttatgttag gggaaactgc caaattgaaa taagaaagcc    22200
atctcccgca agcaagcctc tcctcctaaa gactaatcat aatgcaagag aaattttcca    22260
tttctctcag gaatcagaat cctttgctac atgcacaact ggaaggaaag tagtacaaat    22320
aggaggatcc ttacctgatg ggagaaggga gatcttgcca ttcaggagtt tgctttgaat    22380
ctctttccac gtgcatgggt gctgtcacag tacatgtgac aggctgcaac agggtttgag    22440
agggttcctt gctggaaggc aatgtcatag gaaaacaggt tttatgaagc agtgattccc    22500
ccaaggagca aaggagttga ataaatagga tagttcctag actagaagag caggcttgcc    22560
tacactctca cacccaaacc aactgccttc tgttgttctt ttttgaccc aaattctatg    22620
cagaatcttc tcttatcaaa ataaataaat aaataaataa tgactgcaaa caaaaaactc    22680
aatagctcct agtattactt aacttttgca tgattttaac gtgtcaatgc ttatcttaaa    22740
gcactgtttt actaatttca ttcctatact tatcctaaaa gatctttagt gacgtgcctt    22800
ttctcacagc aggacgcttc aaacttgggg gagtttattt aaaatgcctt tttctggact    22860
```

```
ccattcctgg aggtctagaa tgggatgcat tcataatata tatgttaagt gttccaggaa   22920
atcaataggt gattgggata ggctaaataa tggtcccca aaaatgtcct cattgctgtc    22980
cccagaacct gtgaacatgt taccttcaac gacaaaaggg actttgcaga tgtgatgaag   23040
gatcttgaga aggagggtta ttttggttat gcaggtggtc acaatgttat cataaggacc   23100
cttatgagag ggaagcaaga ggatcaaaat cagaaaaaga tgtgatgaca aagccagagg   23160
taagactgat gcactttgaa gatagaggag agagccatta gtcaaggat gcaggcaaca    23220 tctagaagat agaaaagcaa ggagacaaat tctcagatgg tttctaacac cctcaaaaag   23280
aatgctgctc tgcaacatct tgattttaga cttctgacca ccagaactat aaaataatac   23340
atttgtgttg ttttaagtca ctaagttggt ggtaatttgt tacagtaata attggaaact   23400
tgtatagtta ttcacgaaaa gagtattacc ccaaataaaa cactttctat agacatcaac   23460
ttcaatatct cttattattg taaaggatcc tggagcacta ggagcgaagt aaattgttca   23520
acttcactga gggacttagg gaaaatccag gacaacagtg gaattatctt agtttggctc   23580
tatctcttta tcctggcgtt caaggtatct tcccctagtc taggccaacc tttcccacat   23640
tatcccatta tttctatatc cttacttcta taagcaagca aaatagtgga tatattttcc   23700
ccctgaataa gccccattat ttctgtttca ctaccttgat acatagactt ccctcttcct   23760
gaagtccttc cattctcgaa tgttaggttt cactaaaggt cgggtcctgc ctcttcctta   23820
gctatccagc attaggtgag tactgacctt ggaactctta tggtgtcagc atggttgctc   23880
tttaaagatc atgatgaaga atccctagtc tatttcttcc tcagtgtgat gatctggttg   23940
gctctgaggc ttgtggatac ttcctaaagc aatattgaag aaagaatgaa tgactaaaga   24000
ccttaatcca agtcaagtgc ctagattttc aagttccctc tctttatgaa ctatatttca   24060
cttatttcca caaagtttta aaaataaata cccaatgaac ttaaaaaaat ttgtagagat   24120
gagtgtcttg ctttgttgcc caggctggtc ttgaactcat ggctgcaatc ctcccatctc   24180
agcctcccaa agtgctggga ttatagccat aagccaccac gccagctgca aaaaatttca   24240
attacatgtt ctgttagtat acatagatat cttcctagtt taacagtaaa aatcttctca   24300
gttacttgac tgatagatga caactcaata tttacatctc attggggtaa cacaacattt   24360
taaaacatat ttcttattgg catatacttc acataacata aaattcagtt ttaaagtgtg   24420
gtattcagtg gttttttagta tattcacaga gttgtctgac cattaccatt atctaattcc   24480
aaatatttta attaccccca taagaaaacc tgttaaccat tagtagacat tcaccattct   24540
ccctcctttc tctaagccac tggcaactac taagccactt tctcactcta tggattttcc   24600
ttttctgaac acttcatgtc aattaatcat acaataatca agtggtcttt tatggctggc   24660
ttctttcact tcacataatg ttttcaaggt tcattaatgt tgtagtatgt atcagaatct   24720
catttctttt tacggctgaa taacattaca ttgaatgaat ataccacatt tgtaatccct   24780
tcatcattga cagacatttg ggttgtttcc acctttagc taatatgaat aacgttattt    24840
gtgcaacaat ttttgctttc tgttggtatt tgtgaaaata tgttttcaat tctataaggc   24900
atatatatct ctaggagtag aattgttagg tcataaatca tttgtataac ttttttgaggt  24960 actgccagat tgcttgccac cttttcagtg gctgcatcat ttaacattcc cacaagtaat   25020
gtataaggat tgcaatttct ccacaacctt gccaacagtt gttattttcc atttttatta   25080
tagttatgct tgtaggcata agtaagata tctcattgtg gtttttcgtt ttctaatgga    25140
taatgatgct taccatcttt attggccatg tgcatatctt ttttggaaaa aatggctatt   25200
taaatctttt gcccattttt taatagtttt tttaaattg tagagaacat agcctttaaa    25260
```

```
attaaaataa gagtccagaa gttgggctat atttcctagg tgttagctag tatcttgtcc    25320
ccttttcata gatttatttg tgtatctcag gttatcagtg ccactataga tctcctccct    25380
cacagcaatc aaacttagga cttcatccag aaatgggtgg agagaccact ctcccagctc    25440
caaaaatgct taccgggatg gtcaatgact gcctccttct tgttgctcag ccctctgaga    25500
gtccttggct ggctgtgcag tttgctgcac ccagttactt tctttctttc tctctctctc    25560
tctctctttg tttttgagac agaatctgat tctgtcatcc aggctggagt acagtggcac    25620
aaacatggct cactgtacct tggacctccc aggctcaagc gaccctccca ccttagcccc    25680
ccaaatagct gggactacag gcgcatcacc acacgtggct aattttggta ttttggaaga    25740
gatggagttt caccatgttg cccaggctgg tcttgagctc ctgagctcaa gagatcctct    25800
ggcgtgggcc tcccaaagtt ctgggattac aggtgttggc catggcaccc ggcccactct    25860
gttactttct attgcattgc ctgttacctt attttatagc tttcataata ctcatcatct    25920
gatatttctc atttgtttgt ttgctgatta tctcttcctt ttggaagcgt gaattccatg    25980
aggccaagac attgcctgtt atgactgact gtgtgactga tgctgacaca gtgcctgtca    26040
catggtagac tggggctgag gttcagttcc caggggtctg gctcctcagg aagtagcatg    26100
tgtcaaggga agatgtgtga catggggaag aactttctag aggagttacc aggtcctcca    26160
gtattagact cctttatttt acttttttaaa aatgttttga agaaaatctg gcaaactaca    26220
agcatactca tcttaatagt aattatcaga agcaagtcca gattccggaa actaatttaa    26280
ctcaatgaat gtgttaaact agttcaagat taatcagaaa cgcttagatg tctttattct    26340
ttctgcaatc ctaaatgaaa cataataaac actttaggct aaattttgc atagttttaa     26400 gctcatcatt tgcatagtag tctcattgct accacagata gaaagataaa ggtctgaatc    26460
tgtattgctc cccaggaaac tacattttag cagcacttac cgagtagtca cacccatcta    26520
aattcaaatc ctagctctgc cacccacctt caggcaaaaac ttggccaaga tgtttgactt    26580
atctgagtct gtcccatgtc tcactgaggc tttcccaagt ggggaaaatg gagccagtaa    26640
tacaggccta cagagctgtt tgaagattat aaacaaaaca ttgcccacaa taagggatca    26700
ataaatgtta gctgattttt ctctctttaa atttctgttt cagctacaac tctgttatgg    26760
gtaggtgtga gggaagaaa ttaggtaaaa aaaaatctaa agaaaaaac attggggaaa      26820 ataaaataag aattctcatt tagtttgttt catgcgcgtc cgtgtgaaga gaccaccaaa    26880
caggctttgt gtgagcaata aagttttaa tcacctgggt gcaggcgggc tgagtccgaa      26940
aagagagtca gtgaagggag ataagcgtgg ggccatttta taggatttgg ggaaggtaaa    27000
ggaaaattac agtcaaagag ggtttgttct ctggcgggca ggagtggggg tctcaaggtg    27060
ctcagtgggc aggagtggga gtcacaaggt gctcagtggg ggtgcttttt gagccaggat    27120
gagccaggaa aaggactttc acaagataat gtcatcagtt aaggcaagga ccggccattt    27180
acacttcttt tgtggtggaa tgtcatcagt taaggtgggg cagggcatat tcacttcttt    27240
tgtgattctt tagttacttc aggccacctg gcatatacg tgcaggtcac aggggatgcg      27300
atggcttggc ttgggctcag aggcctgaca ttcctgcctt cttaataaga aaataaaac      27360 aaaatagtgt tgaagtgttg gggcggcaaa aattttggg gggtggtatg gagagagaat     27420
ggacgatgtt tctcagggct gtttcaagcg ggattagggg cggtgtggga acctagagcg    27480
ggagagatta agctgaaggg aggtcttgtg gtaagggtg atattgtggg gatgttagaa      27540
gaaacatttg tcgtatagaa tgattggtga tggcctggat acggttttgg atgaattgag    27600
aaactaaacg gaagatacaa ggtccaaata aaagaaggag aaaaatgggt attaaaggac    27660
```

```
taacaattgg gaggacccag gacatccaat tagagagtgc ccaagggggt tcagcgtaat   27720
tacttgcttg gttggcaagt ttttgggctc tatccttgag tttttttaatg ttgtcataca   27780 ccaggccaga ttgatttagg taaaaacaac actcctcatt taagaatatg cagagtcctc   27840 cttttttcagc agtgagtaag tcaaggcctc ggcggttttg gaggacaact gcagctaaag   27900
agtcaacttg ggcctggagg actgataaag tttgtgatat gtctgtgatg ctagcagaga   27960
agtcattaga caggctacgg aaggtcatga cagacgttga aatgcctgct attccagtac   28020
cgagagcaac agtggaggca gaaagtccta aaccgaccat caaggaatt agtggaataa    28080 ctctttttttg ttgtgtcggt gtcatgaggg gaacagggag ctcttcggtc ccatttgcaa   28140
attgaatttt gggggtaagg aagactagtg tacatgtgcc tgtccaattg gcaggtaggc   28200
acatgtaggt agaggatcca cagaggaaga agagaccttg tgcgaggcaa aactggagat   28260
gtaaagtaaa aaggtgagaa ggagtgctga aagggggtgtc ttgtacccag actcctaggg   28320
atccagctag ggcggcagct gtcagaggtt gtaatgggga ctgatgggt aactgcgtag    28380 aggggaaggt tcgattttca tggtgtatga gaaaacgtcg agtatctacg agcaatcttt   28440
cactgttatt ttcggggctg gtataagta aacaagaaga gggcctggga ggagagtctg    28500
atgagcaagg ggaagatagc caaggatgga gtgaaataca gggcaagtgt cttcctaagc   28560
aataattact gctaatgttt ttaagtttgt cagtattgat agagggcttg tctgtaatat   28620
ggagctggaa ggctccaatt gtttcattga tgtttgtagt tggacttcgg agatgaagag   28680
taaaggaaca tcgagaaggt gaaagattac ctagggggaat tccagtgggt ctttgccaag   28740
agatacacaa aggagcggcc acaggaatag tagtttgtgt tgtgagaggt ccaaatatgg   28800
ggggagtaga gttgatataa ggagaaaggt tttttaaata agtgcgaagg agggcggcag   28860
cttgctgatg tgaaatgtct ggggaagtct tgctggacct gtctagaaag taaatgagtt   28920
cttcaggagg gtaaaggtga gggctgttaa aggaagttcg gaggtgtagg gagatggggag   28980 atgttgccca gtctgtctgt aaggcgggga cagctgtgta ggcactggaa gaaagggaaa   29040
tgcaaagcca gcagttgttc actaaggagg gattagaagc ggctaggaga gaatgggtaa   29100
ggttgatagt gtggtggaga tagctgggga gaggtagagg atgacataag aatgggaatg   29160
agaataagag tgagtataaa agtaaagaat agaacttcat cagggtggaa gtattggagg   29220
gtgccttgcc agcaaagatc atctatccac tctaagacgg agttaagagt ggcagtttgg   29280
ggatagcacc aagagatatc agctgtgatg gcttgaagaa acagtgtaaa ccggcggtgt   29340
aaacaagagt agggcattta taagtagttg agaatggaga ataggagtat gaccggacag   29400
aagataatag ggatgactag ttttttgggg cttggcctaa gtggtggggt gacttcgtaa   29460
agccctgttg caaaaagtag ggtaaggatg aacagaccta atagaatgaa gggatgtatt   29520
aggctcataa gggttattac tgttcttcag aaatatgagt gagtttaagg gaagtggggg   29580
agagtacttg cgacttccag gaggaagagg aggggattagg ctggctgtcc gatggacaca   29640
gctttattct ggaatggtga acccagtggg gaggattctg caggcagacg gcagtcgggg   29700
tactatagat gactaagtag ggtccggtcc atcgaggttg tagagtttga ggggtcagat   29760
tcttaacaag aactgatcgt ccagctaggt tgtcttcata tggctgggga tctggagtag   29820
gcaagagaag attagcagcc tggcgaattt cctgtctagc ctgctggagt actggaagat   29880
agtcgcctag agggctggtg tctgggatga ggttggggcc aagcaagaaa gtgcgtccat   29940
ataaaagttc aaatggactg tatcctgtag catctcgagg acaggctctg attttgagaa   30000
```

```
gagcaagagg taaaagtgct gtccaatcct ttgtaagttg gaggctaaac ttggtgaggt   30060
gtgcctttaa aagaccatta gtccgttcca cctttcctga agattgagga cggtaagggg   30120
tatgaaggtt ccactgaata ccaagagcct gagaaactac ttgggtgatt tggctagtaa   30180
aggctggtcc gttatcagac tgtatagagg tgggaaggcc aaaccgagga attatgtctg   30240
acagaaggga agaaatgacc acagtggact tctcagaccc tgtggggaag gcctctaccc   30300
atccagtgaa agtgtctacc cagactaaga gatattttag ttttctgact cgaggcatgt   30360
gagtaaagtc aatttgccag tcctgggcag gggcaaatcc ccgagcttga tgtgtaggga   30420
agggaggagg cctgaacaat ccctgagggg tagtagaata gcagatggaa cactgagaag   30480
tgatctcctt gaggatagat ttccatgatg gaaggaaat gagaggttct aagagacggg    30540
ctagcggctt gtaacctaca tagaagaggt tatgaaatga tgacagaata gaatgggcct   30600
gtgaggctgg aagaagatat tttccttggt ctaagaacca tttgccttgt gtgggaagag   30660
attgataggt ggaagtttca gtgggggagt aggtgggagt gactgaagtg aaggagaaaa   30720
actggccgtg agggacagaa gttggagagc tagctgcttg tctagccact ttatcaacat   30780
aagcattgcc tagagcaatg ggatctgatg cctttttgatg ccccttgcag tgaatgaccc   30840
cagcttcttt tggaagtaaa gcggctttga gcagagttttt tattaaagag gcattaatga   30900
tggaggaccc ttgtgtagtg aggaaacctc tttcagccca tatgactgca tggtggtgca   30960
ggatatggaa ggcatattta gaatcagtat agatattgac gcatagtcct tttgcaagag   31020
tgagggcttg agttaaggca actagttcag cttgctgaga ggtagtggag ggaggcgag   31080 cagtagcctc aatgatagat gtggaagata ctatagcata gcctgccttc gctggtgagt   31140
ggcgattagg cctggtggaa ctgccatcaa taaaccaagt gtgatcaggg tgagaaacag   31200
ggaagaagga aatgtgggga aatgggggtga atgtcaggtg gatcagagag atgcagtcat   31260
gagggtcagg tgtggtatcc ggaataatgt gggaggccgg attgaagtcc gggccaggaa   31320
caatggtaat tgtgggagac tcaacaaagt gtaagtatag ctgaaggagt ccgggagcag   31380
aaagtatatg tgtcaggtgt gaggaagaaa atagattttg gaaattatga gagctgtaga   31440
gagtgagttg agcatagttt gtgattttga gggcctctaa aagtattagg gcagcagcag   31500
cggctgcacg gagacatgat ggccagccta aaacagtaag atcaagttgt ttggacaaaa   31560
aggctacagg acgcgatcct ggtccttgtg taagaattcc gactgcacag ccctgcactt   31620
cggctgtgtg taatgaagca ggttgggatg agtcagggag agctagagtg ggggcagttt   31680
ctaaagctgt cttcaaggaa cagaaagagg agtgggaaaa ggatttagga tctatggggt   31740
cagctaagtt tccttttgtg agtttatata atgttttgt taggatggca aaaccaggta   31800
tccaaaggcg aaagtatcca accatgccca ggaaggaaag gagttgttgt tttgtagaag   31860
gggttggggc ttgagagatt agtcagacac gatcggcagg gagagcacgt gtgttcttat   31920
gaagaattat gccgaggtag gtaacggatg gagaagaaat ttgagctttg gagggggata   31980
cccgatatcc tttggagaat aaatgctgaa ggagcagaag tgtgtcttat tgagaagatt   32040
caaaggaggg gctacaaaga agaagctcat caatatattg aataaggtga gaagcggagg   32100
ggtggaagga aagtagatca tgagaaagag cttggctgaa gtaacgaggg ctgtccctga   32160
aaccttgcgg cagcacagtc caggtaagct gctgggactg atgggtgtca gggtcagtcc   32220
aggtgaaagc aaagagaggc tgggacgagg agtgcaggag aatagtgaaa aaaccatctt   32280
taagatcaag cacggaatag tgagttgtgg aggaaggtat tgaggacaaa agagtgtaca   32340
ggttgggcac cacagggtgg ataggcaaaa caatttggtt gataagacgc agattctgaa   32400
```

```
ctagtctgta agacttatcc ggttttggga caggtaaaat gggggaattg aaaagagagt    32460
ttataggttc tagaagccca tgctgtagca ggcgagtgat aacaggcttt aatccttta    32520 aagcatgctg tgggatggga tattggcatt gagcaggga aggtgatta ggttttaatg    32580 ggatggtaat gggcatgtga tcagttgcca gggaaggagt agagatgtcc catacttgtg    32640
ggttaaggtg gggggatatg agagaaagac gcgaaggagg ctttggttg gggagaaggg    32700 cggcaatgag atgtggctgt agtccaggaa tagtcaggga agcagataat ttagttaaag    32760
tgtctcagcc taataaggga actgggcagg tggggataac taaaaaggag tgcttaaaag    32820
agtattgtct aagttggcac cagagttggg gagttttaag aggtttagaa gcctggccgt    32880
caatacccac aacagttatg gaggcaaggg aaacaggccc ttgaaaagaa ggtaatgtgg    32940
agtgagtagt ctccgtattg attaagaagg ggatgggctt accttccact gtgagagtta    33000
cctgaagctt gccgtccgtg atggtctagg gggcttccga ggcgatcggg cagtgtcagt    33060
cttcagccgc taagccaaga aggagtcagt cagagagcct tgggccagag ttccaggagc    33120
tctgggagtg gctgccaggt gagttgaaca gtctgatttt cagtggggtc ccgcacagat    33180
gggacgcagc ttaggaggaa tcctgggctg cgtgagttcc ttggcccagt ggccagattt    33240
ccggtatgtg tagcaagttc ctgggggagg aggttctgga ggaacgcctg gctgctacag    33300
ttcaggcgtt tggaagttct tgtgtgctgg agatgtggct ggggtttgtc tcacagtgga    33360
ggcaaggaat tgcaactttt ttctgttatt gcacaccttg aaggtgaggt taattaagtc    33420
ctgttgtgtg atttgagggc cagatttcag ttttttggagt tttatttaat gtcgggagca    33480
gattgggtaa taaatgtat attgagaata agatggcctt ttgaccttt agggtctagg    33540 gctgtaaagt gtctcagggt tgctgccaaa tgagccatga actgggctgg gttttttatat    33600 ttgatgaaaa agagcctaaa cgttatctga tttgggataa agaaaaagga gcattaacct    33660
tgactatgcc tttggctcca gccaccttt taagagtaaa ttgctgggca ggtgggggca    33720
ggctagtcat ggaatgaaac tgtaagccgg accaggtgtg aggaggggag gcgataaaaa    33780
gattataggg tggaggagcg gaggctgagg aagaattggg acctagctcg gcctggcgac    33840
gagcagcctg gggaggaggg gaaaggtcag atgggtctgt agaaaaggaa gaccggaaag    33900
actcggcgac gcttggggtt gggactgagg ggacaggcgg gagggaaaga aggaggatct    33960
gggaggcatc gcattgtgaa cagaggctag ggagggaacg aagtgtgaaa aatgcctgga    34020
cataaggcac ctcagaccat ttgcccattt ttcgacaaaa attatttagg tcttgtagga    34080
tggaaaaatc gaaagtgcca ttttctggcc atttagagcc attgtcaagt ttgtattggg    34140
gccaagcagt gttgcagaag aaaataaggc atttaggttt taggtcaggt gtgagttgaa    34200
gaggttttaa gttcttaagg acacaggcta aaggagaaga aggaggaatg gagggtgaa    34260 ggttacccat agtgaaggag gcaagcccag agaaagagt agagacacag agaagggtg    34320 gagggttctt gccctccaga aaagcagaga aggtgttggg gcacgaaat aagggattgg    34380 ggcacagaga taagaggtca gggtgcgtaa ataagggatt ggtgcacaga gataagaggt    34440
tggggtgtgg aaataagcaa ttgggggggtt cttgccccct aggaaagcgg gacttgccac    34500
taagggtgaa ggagaagggg ttgaggggta cttgcccctg ccccaggaaa gcgggacttg    34560
ccactaaggg tgaaggacca aggcaggcgt ccctgcgtgg tctgacaccc ttgaaacgtg    34620
agtgtagaat cagagaggcg tccctgcaat gatgaaacac caagggaagg ctgccttccc    34680
agtctgtgac cggagccgga gttttgggtt cacggataaa acatgtctct tttgtctta    34740 ccagaaaatg aaaggaattg aaattaagag aagggagaga ttgaagtgtg gcaccaagat    34800
```

```
tgaaaggaga aagaggttga gggatagtga gggaggttgg agaagagagt aaaaagaggc    34860
cgcttaccgg atttgaaatt ggtgagatgt ttcttgggct ggtcggtctg aggacctgag    34920
atcgtaggtg gatctttctc acggagcaaa gagcaggagg ataggggatt gatctcccaa    34980
gggaggtccc ctgatccgag tcatggcacc aaatttcatg cgtgtctgtg cgaagagacc    35040
accaaacagg gtttgtgtga gcaataaagc ttttaatcac ctgggtgcag gcgggctgag    35100
tccgaaaaga gagtcagtga agggagataa gcgtggggcc atttatagg atttgggaa     35160 ggtaaaggaa aattacagtc aaagagagtt tgttctctgg cgggcaggag tgggggttgc    35220
aaggtgctca gtgggcagga gtgggggtcg caaggtgctc agtggggtg ctttttgagc     35280 caggatgagc caggaaaagg actttcacaa ggtaatgtca tcagttaagg caaggaccgg    35340
ccatttacac ttcttttatg gtggaatgtc atcagttaag gtggggcagg gcatattcac    35400
tttttttgtg attctttggt tacttcaggc catctgagca tataagtgca ggtcacaggg    35460
gatgtgatgt cttggcttgg gctcagaggc ctgacagttg gataacagtt catgaaagtt    35520
tttcactgca ttattgactt aaggattcag caccatttgg gatttcctct tggctagaag    35580
ttggatttct atacaatttc cttttctgt gggcagtgtt ccccaaactt agctggataa     35640
agatgttatt tgagaataca gattctggaa tgcacttcag atctccaggt cagaaccttg    35700
gaaactcggt cttcaaggat cttttgtgatt gcccaaatat agaaaaacaa tgctgtattt   35760
tttttattct ttgccagaaa ttaggtaatt ttttattttct tttctacgaa gaccaaaaaa   35820
tgaacatgaa agatagttag aatatatttg gcttgactac agagatagaa atgatgctaa    35880
ataatttaac aggaaactta ggaccgtaag aataagctac taaagaacat tatgtcaagc    35940
acaaacaagg taaggacttg cttgagatac atttggtcaa atgctgtagg cgtatgagag    36000
atgaaactta agattctcaa tttcctcttg tgtcaagatc aactttcctc ttgtacggct    36060
gtacctaatt tagtatgtgc actactgaaa gatgtgttga ttcaaagtga catgtgcaca    36120
atgcatttct tagtttgcag tctttgttta taaaattatc tctaaagtag ttgcttagag    36180
ccatataaat atattctagg agatgtagta agtcgttgaa atggttaata tgcttttaga    36240
tttttatgat atgatttaaa aaatccattt gaaataacag caggacagtt caaatagtcc    36300
tatcttaaat tctggaagta gaggccaggc ttggtggctc acccctgtaa tcccagcacg    36360
atgggaggca gaggtgggcg gatcacgaag tcaagagatg gagaccatcc tggccaacat    36420
ggtgaaacct catctctact aaaaatacaa aaattagccg ggcatggtgg cgggcgcctg    36480
tagtcccagc tactcgggag gctgaggcag gagaatggca tgaacccggg aggtggaagt    36540
tgcagtgagc cgagattgag ccactgcact ccagctcagt gacagagcaa gactccatct    36600
taaaaaacaa aaaattctgg gaatagaaag tcatggggag aaggaaggaa gactgcgcca    36660
aaagaagaaa caaacgggtc ctacatttcc tgagcgtaga gcagtctaag aaaaatgctt    36720
ttgcacgttt cattgtcttt tttccaactc tcattgtttt ttccatcctt ctcctctgga    36780
ctatagcacc ctcacagata tagtacaagt aggccagcca cacccaacc aaaactctcc     36840 tccacttaac aaataaatct tttatttcct caaaacagtg caaaaatctc aactaagttt    36900
agaaaaaagg ttgtatctca ctcataactt tctatcatct caatgatatc tatcttattt    36960
tataatggaa gctataactc aagacacata taaaatttag ggaatgttag gcagtataaa    37020
aaaactaaag aacaaatcaa gctatagata ggaatgccag agactctaat attatcccac    37080
tttttaaaag aacttgaggg gcactacctc ttacagtatt catggttgtc tgaaacgtga    37140
aattgaatat caagtcctaa aaaattcaaa ttcccttttct tcatgcaatc ccaattcccc   37200
```

```
taaataggaa gcacttaaaa ataatttgta accaaaaaaa tctcagtaat gcccaggttt    37260
cagtaatatg ccaggtcaga gagaggtgga tccattcctt tatttaaatt aagttggtgt    37320
catgatatct tcattatact aagggaaaag taaggtttaa aaatagaaat tcatggttgt    37380
tttgtgttgt tttttagttgt agctgttgtt tgctctccat gttttatttt tacgtacttt    37440
caaatttaca gaaagttgt aagagtgctg ttatggatgg gatgtttgta tcccttccaa    37500
attcatatgt tgaaatccta atccccaatg taatgtattg gggagtaggg atttggggag    37560
gcattgaggt catcagggtg gagccctcat aagtaggatt agtgcagtta tatatgggac    37620
cccagagagc tctcttgacc tcttttgcca agtgaggata caatgagaag atggcagcct    37680
gcgccgtaga agaggatgct cgccacaacc caaccacgct ggcaccctga tcttaagctc    37740
ccagactccg taactgtaag aaatacattt ctattattca taagcccct aatctatggt    37800 gtgtgtatat gtattctttt aatatactag cccaaactga ctaagtagta cagaaaattt    37860 tcaaaaccc ttcactcaaa tcccccaaat attacatttt accttgtttg ctttatcttt    37920
caaacatctt tttccctgaa tcatttaagc ctatggtctg gaaatgatgc ccttcaccac    37980
taaatcctcc aaatcaccat ggatccaaaa cctgctagct gggtgagtct ccagaccctc    38040
tgaaggataa aggcccataa catctctccc ttggctttca gatcaacatt tggttccagt    38100
ttctaatagc tggaacatct ccttagaaat ttggagcagc ttctggactt ctctgaaagc    38160
aagaacagag taactattgt ccactctacc agagcctttg cttctaatg cttttcaaca    38220 tttaaagcca ctccagtatt ttaaaaaata cagctcttct tttaccttag ctgctgacct    38280
aatttagctg aacacatttc attaaatatt tattaaacat cagttcgtgg aagcactgta    38340
tcaaatgggt acacaagggc aatgcccact gggcaggttt ccagctcatc aaaaagcaca    38400
gctctgaatt aagagggtgg ctgaggctct gaaaggaata agggcaacag tgaacttgac    38460
tatttgaaaa aatgttctgt gataatagta ggaaataaaa aaagatgagt taaagaagcg    38520
gaaccaggaa catgataagc acagcataag atcagctata tttcatcttc ctgtgtaggt    38580
actggaatat gatcttttca tttaatttgc aattgctcat tttcttgaca acaaaaggca    38640
gatccaagtg ttgtggaggc tgaagattat ataatttggg agtttctcat taaaaaaaaa    38700
atgagaacac aaaataaagt gtaaaaataa atacttaaaa tgatcatttt atctcaacaa    38760
atacattttg aaatctgaaa aatgtcacaa aagttaataa aaataacaat ttgccagaca    38820
cagtggctca tgcttataat cccatcactt tggtaggcac aggcaggagg atcacttgag    38880
cccaggagtt caaaccagc ctggtcaaca tagtgagacc ccatctctac aaaaataaag    38940
caaaaattag ccaggcatag tgacatgtgc ctatagtccc agatacttgg gaggctgagg    39000
caggaggatt gctaaagccc aggaggccga ggctgctgtg agccatgatt gcaccactat    39060
acttcagctt ggccaacaca gcaagatcct gtctcaaaaa atgtaatagt aattttgtta    39120
attaactgac atgtctctat aatatttttt tctgcattgt ttagctggat gctctcttca    39180
tataacaagt actttccaca cagagaatat aaaaaataat tccatcttac ctctagcata    39240
attggataca atttttatca ataataaata aattgactcc atcattagag ccaatttaaa    39300
caattcttta aatttccccc tataattata tccttgatct tcttgacagt acaggcaaaa    39360
ttttcctgta attaacaatg agagggtcaa gtcccctctt ggaggaattt atcagagtct    39420
ttccaaacgt ggaaccttt gttagagtga gtgtaaaaaa aagaacaag aggacctcag    39480 gacatgggag agaagaagg acaatgaaaa taaacaatag ccttaaaaat agaagcgaa    39540 aacagagcta ggtgagaaga tgctgaaact atctttactg aacaccgact cttaaggctt    39600
```

```
ttggtaactt tttctcttct cccatcacaa aataaatatg aatgccaaag ggcaggcaca    39660
cttccactgt tgagagaaac agatctaaaa ataagtagga agcagacaag aacgagcaat    39720
gaacatgatg agaaccatgg tgtctacttt taggttaact atggaggcat gtaggcacag    39780
atggaggaag ttagtttatc tttgctgctg cacttaaaaa ataaaaacca aaaatataaa    39840
tgccatcaaa acattgactc ttctctaacc aaaattttg gttttatatt taaggccaag    39900
cccatttaga agaaaagcac attcatttgg gttttgtggt ttggagaaag gactgccaga    39960
gaggaggtga aagccacagt ggagcattcc tggacaatcc attgcaggct tgggagatca    40020
ccatgcaggc agctcctgct ccataatagc caaaatagca acatgaccac aaataattca    40080
aaggctgaaa cattttgttc ccaccagttc aaactctcct gcttctgtca aatggctggt    40140
aatcctatct cctctactaa gcctttccta aatgaaacag tggcaactcc ttttgaattc    40200
tactatttat tacataaaca cacaattccc gtggttccct tatcactcca ttaaatgcac    40260
ttgccctctg attgaaacac aatgcaaatc cttttatgct acatttgttc aatgcttgtt    40320
gccttgactg tatatagcct taatatccgg taggtgcttc taacttattg taagttccac    40380
atctaattca caaagtattt tgcttagcaa tgcctcttat gatgcaaata aactagtatt    40440
tatcacgagt gctttaggat acagacaaga agactatttt agagaaaata agaattaaat    40500
aatggtaagg aaagcaaacc accccctgcga tgtgcatgc ctccaccacc accccttttc    40560
cctccctgga tggtgtctca ctctccacct ccttttgtc acttgtcctt ggtcacacat    40620
caatctgccc tcagccctcc agagaagact tattcttcct gcctgaaatg ttatttctcc    40680
cttgttcatc taaccttgtt ccttttatt aagtgcttta tatatcgga agactacata    40740 aattatgtct tcacgttaaa taatagtaat acaatgaaca cctgtgcatc cacttttaaga    40800 aatagaatgt atctttgaag tctttgtgtg tactgtcatg ctcgtgtcct tccacattcc    40860
aaggtaacca tattcctagt ttagtgttaa tcactgtctt gtgggttagt ccaagtcttg    40920
ctattcttta gagttttact acctatttct ccctaacaat acatatattt agtttgaaaa    40980
aaaactcaga gcaatcgcaa gcctagtgga gtaagagaaa gatcaacatt gacactaaga    41040
gaggacatgt cccagaagat gagctaacag aggctctccg ttacagcatg gcttcagttt    41100
ccccaggagt ttacaaaagt catttgcagg gaagtcagaa ggagagagac tgggatgtc    41160 gggctctcta agacagggca ttggggtggt ctgtgaatgt gagtctggag ctggaggtct    41220
ccaaccataa ggacatgaga ggtggcagct ctgccttctc cacttctgag ttcaccacag    41280
cccacctcct gctcttcaga gtaggtggaa gatcacccte ttttgcccca tctgaagaag    41340
aaactccaga ttactaatgg gaagctgaag ggcagtcagc caggctgact ctaagttgtc    41400
cttcaaaatg tagctcaggg tttcctcttc agcagaaact tttctgacac ccacatgcaa    41460
tgaccagggt caacctttta accccctgtg cactctgtgc taaccctat caacagctct    41520 ccctcctact gctgtccctc ttccttatta aactggatgt tcttcgaggg aataaattat    41580
cttatcaatt ttactaataa taacagtatc atctgatatt tgctttattt tataaatgtg    41640
gacaaacctc attaacatta aataccaaga tttaaaaatt gtaaggcaga atatgtgttc    41700
ttgttactcc gaatttattg gaaataaaga attttgagtg tctcttctat taaagaagtt    41760
ctgtgagtgt tccttgcatt cttctttctt caggcatgcc tcatctcata acatttcagt    41820
tactgtgtca tttgcacagt tgagaccttt ccacatggat acacgtgaaa taaaggtgtt    41880
acaaaaagta gtattttca ctttactttg tgcctaaaaa caaatacacg tgtatggtac    41940
tacataaatt aaaaaatatg atttaattat cttctacttt ttataacacg cctggaaatt    42000
```

```
gtttttactt ttataattag gaggtgaaca gcaggtctac aaaatattaa cagaaaaagc   42060
taatacctt  taattaaact tttctaacta taactttcaa gataagtacc tacactgttt   42120
taaagtaagc tataaaatta aagttagtaa aagaaaaaa  aagatattaa tatatcagac   42180
attacctcac catccagaat taaccaggtt ataatgctgc atatcctccc tgatatcatg   42240
tattttaaa  taaatcatt  ctgaatattc tggtctttac ctgatttatt tcattcaaca   42300
tatcccggtt atctcccat  ttcaataaat gcacttctaa agccataatg tttaatgtct   42360
gtatatgaat ctctaagcat gtagtaaaat cataatgcaa aataataaa  aataaacaca   42420
aaattcagaa gactgggtgt tttttaatg  agagaattgg atttgttaag ggtttagcca   42480
tgattccaaa cacacacata ttttcatta  tttgtatacc gtacatgttt tatatctaaa   42540
aatttccata tgaatattat attatttcat aatatatgaa aaaagcactc attccaataa   42600
gtgtttgtat ttttcccat  ctttcactaa acaaacccct gacaaatatt cttctattaa   42660
aatgttgcaa atatcctctt tttaatccta ggataaattt ctagaaatag aattgctgag   42720
caaaatggtt tgtacaattt taaggccatt aatatatatt actaaactgc cacccagcaa   42780
agtaatgtca atttctattc ccatcagcaa tgaatgagag tcattttctc tcattctttg   42840
ccaacactga acataatgaa gaagaaaaaa atctctgcca atttgatcag tgaaaatttg   42900
tgtttcatat tttctctaac ttgcatttct ttaactacta gtgtgattaa accttttaa   42960
agttttacc  cattttttac tttttcttct attaattgct tattaatggt ttttattctg   43020
ttagggtatt attattctta tgtatttata aggttatata attaaagatt tcgaactttt   43080
gtctgtctaa tttgtggtag gcagaataag gcttcccca  aatgtccaca tcttagtcct   43140
cagaaagcct ccaaacatct tatgttacat gacaaaggg  aatggaggtt atagatggaa   43200
ctgaggttgc taatcaactg acctaaaata gggagattat cttggattat ccagcggact   43260
aaatggaatt acaaggttct tagaagtagg agagaggtgg aggagggatc agagtcagag   43320
agaggcttga aagcgctgta ctgctggctt aaagatggag gaatggagcc acaaaccaag   43380
aaatgctggg gggctctaga agctggaaat ggcaaagaaa tagatgcgct cttgaagctt   43440
gcagaagaac acagctctgc cagcatcttg atttttgtca aatgagactc atttcagact   43500
tctgatctcc agaactgtaa gataaataga tttgtgttgc tttaagccac ctattgtgtg   43560
ataatttgtt gtaatggaaa tgggaaactg attcacaagt tgcaaatgtt ttcccgattt   43620
ttatatacat aatctttaca aagcaatcaa aatgtcccctt atatttagta ccattttaaa   43680
atgtattcat tatacctctt ctatgttcaa ctacagtgaa gcagataaaa tttgaccaaa   43740
aatacaattt ttttttcttt aaaaaagga  gggggtttcc tcttcaccct ttcttctcc   43800
ttttctttc  cctttgcttg gaggtggctg ggagctgagg aagctagaag aacaaggaga   43860
aaatggctga ggagatagtc ctggggtcag gagccaaaaa aagctgatga catagtcagt   43920
agattggtta tatgcagggg gattaaggaa ataagcaaat attgaagata gtgagagcca   43980
ggttttcac  tgtcagagaa gggatttata aaaatgcaaa tgagccagtg ctttggctca   44040
tgcctataat cccagcactt cgggagggca aggcgggtgg atcacttgag gtcaggagtt   44100
cgagaccagc ctggccaaca tagtgaaatg ccgtctctac taaaaataca aaaattagcc   44160
tagtgtcatg gcacgtgcct gtaatcccag ctactcggga ggctgaggca ggaaaattgc   44220
ttaaaccctg gaggcagagg ctacagtgag ccgagatctc attactgcac tccagcctgg   44280
gtgacagagc aagactgtct cagaaaaaaa aaaaaaaaaa aaaaaaaaaa tatatatata   44340
tatatatata tatatgaaaa tggagaaggc taaggtatta cgttgtcatt gagaaaaaga   44400
```

```
aggagggagg gagagaggta cagatgaaac agatatatgt atatatatat acacacactt    44460
ttataattag atggatatat atagagagat agatgatata taaatacagc tctgtcggcc    44520
tggtagtaat gagtatacta agcacccaga tctggattta taaatgcctc taccaaaagg    44580
aaccagactg cagagaaaaa tagttgattc taaggttgag acatggaaag tacaaaatta    44640
gcccaaaagt atggaaatat tctaagaatg atggaaacat gcaaaataaa cccacggaac    44700
ttagcttgaa gaggctctca tggccaaatc tgagacacat gaagtatcag aataaatgtt    44760
gatagtaacc agattataac ccattgaata aagtaggaat ctatcagacc ataatgaatg    44820
aataaatgaa taaaaggaaa aaattcttgc agtataatgc caacaaacta atgtggaaag    44880
aatgatgaca catatcagag aggaagttga atcaggtagg agtcatcagt ggatgccaaa    44940
gccagtgggt agaaatttga tgaataatta tatatttgca tagtcttgag tatctcccca    45000
tgaaacactt ccactcacaa aggggaaaat ggtggaccta tggtccagga acctggcaga    45060
caccaacttg aacaggttgt caatgttaac atctccaggg ttcagatgaa ttaacattga    45120
aggattcctc atatactact ggaagtacaa tatcatttca gtgctattcc tgataagaat    45180
gtatggtgtg agtgtgaaca tgaggaaata ttagatggtt ccaggttgat tgatgtggtt    45240
tatactctaa aactgcaaat tacatgaatg tcaaggaaaa gactgtcaag ccgctccatg    45300
ttgaaggaca ctaaaataca tgacaaccaa atgcaatgca tgatcctgga ttgagttcta    45360
gaacaagaag gagaaagaaa cattatggga acaggaatat ttgaatgaga tctttggaat    45420
aattggctgc tagtattata tcaatgttta ttacttgatt ttagatagtg gtatctctat    45480
tacgtggtag agtgtttttt gtatgcaatg cactatgggg tgttaggaat cacgggacat    45540
gctgcctaca actcctatga tcccaaaatg attcaggaaa aaagaatga agtgtgcatg    45600 tgtgtgtatg tgtgtgtgtg tgtatgtgtg tgaactttca tgccacaaat atttattcaa    45660
gcctataaga gatgctaatc actgcaaact aaatattgat aatccaagaa tttaaaaaat    45720
gtaatagtta atactttatc ttagtgggca attaaaaata gaaacaatgg ctagaaaaat    45780
agttttacac aagaggtaat taaaatgggc ctagaagacc atagatttca aacattaagg    45840
aaagtaataa gcataggca aaatatggta gtgtaaaagt gaatggcatt tcagggaata    45900
atgaggtcag tacgttagat gtaagtgacg agaaggaata tagcgagggg aagaaatccc    45960
taaaaaaaaa gaagaaaaga aaaaaaccta gaggccaaat tatgacacta gagcctttgg    46020
acagtatctg cccgaagatt agaagccgct gtagctgggc atggtggctc gtgtctgtaa    46080
tcccagcacc ttgtgggcaa aggcaagagg attgcttgag accaggagtt tgagaccagc    46140
ctgggccaca tagcgagacc tcatctctaa aaaaaaaaaa aaaaaaaaaa aaaaaaaat    46200 taaaaattag ccagatgtga tggtgtgcac ctgtggtccc agctacttgg gaagctgagg    46260
tgggaggatg aggctgcagt gagccgtggt tgcatccatg cactccagca tggatgacag    46320
agaaaaactt tgtctcaaaa aagagaaagt cattgtaggc ttttagtggg caaatgaagt    46380
attcaagtct gtaagttatt aatcaaatgc agtttaaata taaagcccca tataaaaata    46440
tagtttaaga aataagcacc agaacaaaca atttctgaaa cattttcagt ggattatttc    46500
caatggaaat agataaaaat gtgtccaatt aaagaatcca ttataaaaat aggttataag    46560
ataaaaatgt aaacattctt catactcagc atctccaagt actcaaagat cccagagtca    46620
tagcacttta aaactaatgt gattttatta aaggagtgga aaatatgctt agcatgcagc    46680
ataaaaaagt aaaaatatta atctgtgctt tttaatatgg cagggaacat ctattctttc    46740
atttaaactg gagtctcgcc ttctccacaa agacacaggg agaggaaaat aattgacaag    46800
```

```
aataggaagt gaagaattta tgattctcaa taaaagtatg tattgaaaca aaatcagtac   46860
tacacgtctt ctaaaaattg ctgctggatg cctaataaa  gtctaggtgc atgcaagaca   46920
gctgaaaaat gtacttgtta ccacaagagg aaggtgttt  ctccaagtgc tttgcagcaa   46980
tctaccaaag ttttgaagtt ggggcagtag agttgactga catacctga  agccatctca   47040
gtatcagtct agtggtaggg caggaaagct gagagaagtc cctctgatat gcattagaac   47100
ttcaccagct gccaactgaa agctgagtga aaggccaaga gaagtatccc aagttgcaga   47160
aaagtggggg ccatactaca gagaaaatat aactcccaag tgacctaaag agttggacag   47220
tttagttata aagcagaaag acctcttcca tgatttgaaa aacaggtgtc tgtgccataa   47280
agtataaaga gatctgaaat ctcactggtg tataatcctc aagctctgct gaagaccca   47340
attctgccct cagaatactt ttatacaata gtgagctgaa tcttattaaa gttataataa   47400
aattcaaatg ttgcttaaga acagattaaa ttgacccaat tcccaactcc agcagcttga   47460
cagaggagca tgcccttttc tgtagataaa tattgtcagt ctctactgtt ttttcatata   47520
caatgctcag tataagacca ataacaaaaa agacaagcag gaaagtgtta cccccatgac   47580
atgcaattta ctcatgtaac aaatctgcac atgtacccac tgaatctaaa acaaaagttg   47640
gaaaataaaa acaacaatag gatatttaga atatcctcaa atttggaaat taagcaatac   47700
acttgtaaag agttcatgag ttgaaaagat aaactgaaaa ataatttgag ctgagtgata   47760
atgaaaacac catatatcat aatttgtggt gtgcagcagc taaagtatta caggagaatt   47820
tatagctttg aacaagaaaa agggtttaaa atcaattact caagcttcca ccttaaggca   47880
cgcaccacca tgcctggcta attttttgtgg ggatttttt  gaagagatgg agtcccacta   47940
tattgttgag gctggtcttg aactcctggc ctcaagtgat gctcctgccc cagcctccca   48000
aagtgttggg atttcaggca tgaaccactg catgagccat gaaattatat ttatattaca   48060
cattatctt  cagaaaataa aggtggagaa acaactttc  caaatggttc tatgtccagc   48120
ataaccttga taataaaacc tgacacatta taagaaaatt cccaaataat atctttcaca   48180
aacataaaca caaaaatccc ccacaaaata ttaacaaatt aaatcaatca aaatatagaa   48240
agtatttgta atgcaggttg tagtcagggc aactaagtga gaacagaaat aaaaggtatc   48300
cagattagaa agaaagaagt aaaacgattt ctacacacag atagcgtgat ctcgtataca   48360
gaaagccta  aggaatccac taactataaa aactaacaat tcagcaaggt ttcagactac   48420
aatatcaata tataaaaatc aattttatgt ctatacactt tcaatgaatt caaaataaac   48480
tcaaaaacaa aactaagaaa atttataatt gcagcaaaaa gacaggaata aatttaacaa   48540
aagaagtgca aaattaatag tctgcaaact ataaaacatt attgaaagaa attaggtatt   48600
acaataaatg gaaaacatc  ccatgttcat ggatcagaag acttaatatt gttaaaatgg   48660
caatctctat tagaatccca gatatcattg tggaaattga caagctgata ctaaagttca   48720
tataaaatcg caaagggtac ataagagcta aacaatctt  gaaaacacag aaagcaaagt   48780
agaaaaaaat cacacctctc aatttcaaaa tttactccaa aatgatggca accaaaatag   48840
tgtggtgcta gcacaaggac agaatatagg tgaaaggaac tgaattgaga gaccatgttt   48900
ctatggtcaa ctgattttga caagaatgcc acaaccattc agtgaggaga agaatagtct   48960
tttcaacaaa tggggctgga actattggat atccacatgc aaaataatga ggctgaaccc   49020
ttacctcata cctatacaa  aaataaactt aaaatgtatc aaagacctaa atttaaaacg   49080
gaaaaccata aaaactcatt gaagaaaaca tagacataaa tcttcatgac ctcagatttg   49140
```

```
gcaaaggatt cttacatatg gcatgaaacg tatgaacaac aaaagaaaaa aaattgataa    49200
tttgaacttg ataaaaatta aaaccttgtc cttcaaagga aaccaccaat aaagtgaaat    49260
aacaatttca cagaatggga gaaaatattt gcaaatcata tctcttatat gggactttcc    49320
aaaatatata aataacacaa cttactaaga aaaagacag cccaaattaa aaataggcaa     49380
accacaataa acatttcttc aaggaaaata tacaaatggc caataagcac atgaaagatg    49440
tttaacgtaa ttatttatca gagaaatgca aataaaaacc caaatgagat accaattcaa    49500
acacacaagg atggctagaa tcaaaaagtt agataataaa aagtgttggt aaggatgagg    49560
agaaatcaga accctcatat gttgctggtg gagttgtaaa atggtgcagc cactttggaa    49620
aacaataggt aattcctaaa gtgattaaac atagagagac aatatgaccc agcaattcca    49680
ctcctagata tgtactcaag agaattaaaa acatgttttc agtcagatgt ggtagcgcat    49740
gcctataatc ccagtacttt gggaggaaag gcaggtggat tgcttgagct caggctttag    49800
agaccagcat ggacaacaaa gtgagactcc atctctaaac aaaatacaaa aattagctgg    49860
gtgtggtggc atgtgcctgt agtcccagct actcaggagg ctaaggaggg agaatggcaa    49920
ggctgcagtg agccaagacc atgccactgc accctagact gggcaacaga gccacaccct    49980
gtctcaaaaa acaaaacaaa acaaaaacag gcattcaaac aaaaacttat gcacaaatgt    50040
ttttgtgtat acacagcaga attattcata aaagtcagaa agtgtcaaac gtccaacaag    50100
tgatgaatga ataaacacat atggcttatc catataatga aatattatct ggtcataaga    50160
aaaaatgctg atacttgctg aagtatgcat gaatcttgaa aacattgtga ctaaattaaa    50220
taagccagtc acagaaaacc acatattata tgactccatt tatacaaaat gtcaagcata    50280
ggagtatctc tacagacaga caagtagatt gttctttttt taatcctatg ttataaaagg    50340
aatactttgt tatgaccaag tgtaggttat cccaagtatg caacgttggt ttcacacatg    50400
aaaagtacaa catgagtagg ataaaggata agatcctatc atggactcaa tagaaaacat    50460
atttgacaaa attttacact tatgcatgat aaaaactctc aaactaggaa tagaaggaaa    50520
tttcctgaat ttaataagtg caaaatctat agcaaagacc acacttaagg ataaaacagt    50580
gaatattttc ctcttaagaa cagaaaaaaa atgcaaggat gttcattatc acttctattc    50640
aacattgtat tacaagtccc aataaatgta ataaggcaag aaaaagaact acaaggcata    50700
aacattgtgg ggggaaagta aattaacaag tagattccaa aatttacaga aaaaatgcaa    50760
ataatctaaa atagtcaaaa taatgttgaa aacagaataa gtaggacaat acacaatcta    50820
taaaactaca gtaatcaaga tagtgtgtgt tgccataagc aaagacatgt agaccaataa    50880
aatagaagag tgagttcaga aattgacaca cacaagcata gcatccattg atttttttt     50940 ttttaccatt attattttt cttttttttt tattattata ctttaagttt tagggtacat     51000
gtgcacattg tgcaggttag ttacatatgt atacatgtgc gatgctggtg cgctgcaccc    51060
actaactcgt catctagcat taggtatatc tcccaatgct atccctcccc cctccccca     51120 ccccaccaca gtccccagag tgtgatattc cccttcctgt gtccatgtga tctcattgtt    51180
caattcccac ctatgagtga gaatatgcgg tgtttggttt tttgttcttg caatagttta    51240
ctgagaatga tgatttccaa tttcatccat gtccctacaa aggacatgaa ctcatcattt    51300
tttatggctg catagtattc catggtgtat atgtgccaca ttttcttaat ccagtctatc    51360
attgttggac atttggttg gttccaagtc tttgctattg tgaataatgc cgcaataaac    51420
atacgtgtgc atgtgtcttt atagcagcat gatttatagt cctttgggta tatcccagt    51480 aatgggatgg ctgggtcaaa tggtatttct agttctagat ccctgaggaa tcgccacact    51540
```

```
gacttccaca atggttgaac tagtttacag tcccaccaac agtgtaaaag tgttcctatt   51600
tctccacatc ctctccagca cctgttgttt cctgactttt taatgattcc cattctaact   51660
ggtgtgagat ggtatctcat tgtggttttg atttgcattt ctctgatggc cagtgatgat   51720
gagcattttt tcatgtgttt tttggctgca taaatgtctt cttttgagaa gtgtctgttc   51780
atgtccttcg cccactttt gatggggttg tttttttttt cttgtaaatt tggttgagtt   51840
cattgtagat tctggatatt agccctttgt cagatgagta ggttgcaaaa attttctccc   51900
atgttgtagg ttgcctgttc actctgatgg tagtttctct tgctgtgcag aagctcttta   51960
gtttaattag atcccatttg tcaattttgg cttttgttgc cattgctttt ggtgttttgg   52020
acatgaagtc cttgcccatg cctatgtcct gaatggtaat gcctaggttt cttctaggg   52080 tttttatggt tttaggtcta acgtttaaat ctttaatcca tcttgaattg attttgtat   52140 aaggtgtaag gaagggatcc agtttcagct ttctacatat ggctagccag ttttcccagc   52200 accattatt aaatagggaa tccttctccc atttcttgtt tttctcagat ttgtcaaaga   52260
tcagacagtt gtaggtatgt cgtgttattt ctgagggctc tgttctgttc cattgatcta   52320
tatctctgtt ttggtaccag taccatgctg ttttggttac tgtagccttg tagtaaagtt   52380
tgaagtcagg tagtgtgatg cctccagctt tgttcttttg gcttaggatt gacttggcga   52440
tgcaggctct ttttggttc cacatgaact ttaaagtagt tttttccaat tctgtgaaga   52500
aagtcattgg tagcttgatg gcgatggcat tgaatctgta aattaccttg ggcagtatgg   52560 ccatttcac gatattgatt cttcctaccc atgagcatgg aatgttcttc catttgtttg   52620
tatcctcttt tatttccttg agcagtggtt tgtagttctc ctcgaagagg tccttcacat   52680
cccttgtaag ttggattcct aggtatttta ttctctttga agcaattgtg aatgggactt   52740
cactcatgat ttggctctct gtttgtctgt tgttggtgta taagaatgct tgtgattttt   52800
gtacattgat tttatatcct gagactttgc tgaagttgct tatcagctta aggagatttt   52860
gggctgagac aatggggttt tctagatata caatcatgtc atctgcaaac agggacaatt   52920
tgacttcctc ttttcctaat tgaatacct ttatttcctt ctcctgccta attgccctgg   52980
ccagaacttc caacactatg ttgaatagga gtggtgagag agggcatccc tgtcttgtgc   53040
cagttttcaa agggaatgct tccagttttt gcccattcag catgatattg gctgtgggtt   53100
tgtcatagat agctcttatt attttgaaat acgtcccatc aatacctaag ttattgagag   53160 ttttagcat gaagggttgt tgaatttgt caaagtcttt ttctgcatct attgagataa   53220
tcatgtggtt tttgtctttg gctctgttta tatgctggat tacatttatt gatttgcgta   53280
tattgaacca gccttgcatc ccagggatga agcccacttg atcatggtgg ataagctttt   53340
tgatgtgctg ctggatttgg tttgccagta ttttattgag gattttgca tcaatgttca   53400 tcaaggatat tggtctaaaa ttctcttttt ttgttgtgtc tctgcctggc tttggtatca   53460
gaatgatgct ggcctcataa aatgagttag ggaggattcc ctcttttct attgattgga   53520 atagtttcag aaggaatggt accagttcct ccttgtacct ctggtagaat tcggctgtga   53580
atccatctgg tcctggactc ttttggttg gtaagctatt gattattgcc acaatttcag   53640
ctcctgttat tggtctatta agagattcaa cttcttcctg gtttagtctt gggagagtgt   53700
atgtgtcgag gaattatcc atttcttcta gattttctag tttatttgca tagaggtgtt   53760
tgtagtattc tctgatggta gtttgtattt ctgtgggatc ggtggtgata tccccttat   53820 cattttat tgtgtctatt tgattcttct ctctttttt ctttattagt cttgctagcg   53880
gtctatcaat tttgttgatc ctttcaaaaa accagctcct ggattcattg attttttgaa   53940
```

```
gggttttttg tgtctctatt tccttcagtt ctgctctgat tttagttatt tcttgccttc    54000
tgctagcttt tgaatgtgtt tgctcttgct tttctagttc ttttaattgt gatgttaggg    54060
tgtcaatttt ggatctttcc tgctttctct tgtgggcatt tagtgctata aatttccctc    54120
tacacactgc tttgaatgcg tcccagagat tctggtatgt tgtgtctttg ttcttgttgg    54180
tttcaaagaa catctttatt tctgccttca ttttgttatg tacccagtag tcattcagga    54240
gcaggttgtt cagtttccat gtagttgagc ggctttgagt gagtttctta atcctgagtt    54300
ctagtttcat tgcactgtgg tctgagagat agtttgttat aatttctgtt cttttacatt    54360
tgctgaggag agctttactt ccaactacgt ggtcaatttt ggataggtg tggtgtggtg    54420 ctgaaaaaaa tgtatattct gttgatttgg ggtggagagt tctgtagatg tctattaggt    54480
ccacttggtg cagagctgag ttcaattcct gggtatcctt gttgactttc tgtctcgttg    54540
atctgtctaa tgttgacagt ggggtgttaa agtctcccat tattattgtg tgggagtcta    54600
agtctctttg taggtcactc aggacttgct ttatgaatct gggtgctcct gtattgggtg    54660
catatatatt taggatagtt agctcttctt gttgaattga tccctttacc attatgtaat    54720
ggccttcttt gtctcttttg atctttgttg gttttaaagtc tgttttatca gagactagga    54780
ttgcaacccc tgccttttt tgttttccat ttgcttggta gatcttcctc catcatttta    54840
ttttgagcct atgtgtgtct ctgcacgtga gatgggtttc ctgaatacag cacactgatg    54900
ggtcttgact ctttatccaa tttgccagtc tgtgtctttt aattggagaa tttagtccat    54960
ttacatttaa agttaatatt gttatgtgtg aatttgatcc tgtcattatg atgttagctg    55020
gtgattttgc tcgttagttg atgcagtttc ttcctagtct cgatggtctt tacatttttgg   55080 catgattttg cagcagctgg tactggttgt tcctttccat gtttagcgct tccttcagga    55140
gctcttttag ggcaggcctg gtggtgacaa aatctctcag catttgcttt tctgtaaagt    55200
attttatttc tccttcactt atgaagctta gcttggctgg atatgaaatt ctgggttgaa    55260
aattcttttc tttaagaatg ttgaatattg gcccccactc tcttctggct tgtagggttt    55320
ctgccgagag atccgctgtt agtctgatgg gcttcccttt gagggtaacc cgacctttct    55380
ctctggctgc ccttaacatt tttccttca tttcaacttt ggtgaatctg acaattatgt     55440
gtcttggagt tgctcttctc aaggagtatc tttgtggcgt tctctgtatt tcctgaatct    55500
gaacattggc ctgccttgct agattgggga agttctcctg gataatatcc tgcagagtgt    55560
tttccaactt ggttccattc tccccatcac tttcaggtac accaatcaga ggtagatttg    55620
gtcttttcac atagtcccat atttcttgga ggctttgctc atttcttttt attctttttt    55680
ctctaaactt cccttctcac ttcatttcat tcatttcatc ttccattgct gacacccttt    55740
cttccagttg atcgcatcag ctcctgaggc ttctgcattc ttcacgtagt tctcgagcct    55800
tggttttcag ctccatcagc tcctttaagc acttctctgt attggttatt ctagttatac    55860
attcttctaa atttttttcg aagttttcaa cttctttgcc tttggtttga atgtcctccc    55920
gtagctcaga gtaatttgat cgtctgaagc cttcttctct cagctcgtca aagtcattct    55980
ccatccagct ttgttctgtt gctggtgagg agctgcgttc ctttggagga ggagaggcgc    56040
tctgattttt agagcttcca gttttctgt tctgtttttt ccccatcttt gtggttttat     56100
ctacttttgg tctttgatga tggtgatgta cagatgggtt tttggtgtgg atgtcctttc    56160
tgtttgttag ttttccttct aacagacagg accctcagct gcaggtctgt tggaataccc    56220
tgccatgtga ggtgtcagtg tgcccctgct ggggggtgcc tcccagttag gctgcttggg    56280
ggtcaggggt cagggaccca cttgaagagg cagtctgccg gttctcagat ctccagctgc    56340
```

```
gtgctgggag aaccactgct cccttcaaag ctgtcagaca gggacattta agtctgcaga    56400
ggttactgct gtcttttttgt ttgtctgtgc cctgccccca gaggtggagc ctacagaggc    56460
aggcaggcct ccttgagctg tggtgggctc cacccagttc gagcttcctg gctgctttgt    56520
ttacctaagc aagcctgggc aatggcgggc gcccctcccc cagcctcgct gccgccttgc    56580
agtttgatct cagactgctg tgctagcaat cagcgagatt ccgtgggcgt aggaccctcc    56640
gagccaggtg tgggatatag tctcgtggtg cgccgttttt taagccggtc tgaaaagcgc    56700
aatgttcggg tgggagtgac ccgatttttcc aggtgcgtcc atcacccctt tctttgactc    56760
ggaaagggaa ctctctgacc ccttgcgctt cccaggtgag gcaatgcctc gccctgcttc    56820
ggctcgcgca cggtgcgcgc acccactggc ctgcgcccac tgtctggcac tccctagtga    56880
gatgaacctg gtacctcaga tggaaatgca gaaatcaccg gtcttctgca tcggtcacgc    56940
tgggagctgt agaccggagc tgttcctatt cggccatctt ggctcctccc ccgcatccat    57000
tgatttttta acaaaggtac cgacacaatt cctgtattag tccattctca cattgctata    57060
aagaactgcc tgagattggg taatttataa aggaaagtag ttcaatcgca tggcagaagg    57120
ggaagcaaag gcatctttct tcacatgatg acaggtagga gaagtgcaga gcaacggggg    57180
aaaaaacccc ttataaaacc atcagatctc gtgagaatgc actcactatc ccgagaacag    57240
gatggaggaa actgcccgca tgattcaatt atctccagga catgtggaga ttatgggaac    57300
tcaaattcaa gatgagattt gggtagggac acagccaaac cataacaatt cctttgggaa    57360
agcaagttcc caaatggtgt ttgaacaacg gaaaattaaa ttagtaaatc tcaacctcct    57420
acatcactct atgtacaaaa attatttcaa gattaatcat tgacttaaaa taaaagttag    57480
aaaaataaag catctagaaa aaacattgaa gtagatcttc atacgtttga gataggcaaa    57540
gatttcttta gagcataaaa agcaccaaac ataaacaaa acttgataaa ttacacaaca    57600
tcaaaaataa gaacttctgc acattaaaaa atgttataag aaataaaatc aagcttcaga    57660
cttggagaaa atatttacaa cacaattatt ttacaataca aatatctaac aaaggacttg    57720
tatttagaat atataacgac ctgcaaatca ataatgaaga aatctactca ataaatatgc    57780
atataatatg taaacatttt accaaaaaaa atgactgttc aacatgaaca taaaaaggtg    57840
cttatcaggg aaataacaat taaaaccacc acaagataca tactagaatg tttaaaataa    57900
aaaggactga aaataccaag ttttggcaag gaagtgaaac cactgggaac tctcatatat    57960
tgctggtgga aatgtgaaat atcacaacca tttaaaaaaa cctgtggcag tacctttttaa    58020
agttggatat acatggtatc catgaatcca ttcctaggtg tctaccttaa aaaaagtga    58080
aaacatttt cactgaaaaa tgttaaagat gtttcattgt agaacttttt ctccagtgaa    58140
aaagtaaaac ctttaactt tttttttttt tttttttttt gagatggagt ctcgctctgt    58200
cacccaggct ggagtgcagt ggcatgatct cggttcactg caagctctgc ctctcggatt    58260
caccccattc tcctgcctca gtctcccgag tagctgggac tacaggagcc caccaccacg    58320
cccggctaat ttttgtatt tttagcagag atgggttttc attgtgttag ccaggatggt    58380
ctcgatctcc tgacctcgtc ctcgtgactt ccctgcctcg gcctcccaaa gtgctggaat    58440
tataggcatg agcccggcca tgttttcact ttttttaaag ataaaaagac ttgtatatga    58500
atgatcatag ccccccttatt caaaatattc aaaaatttaa aatatctcaa atgtctgtca    58560
tgaaagaatg gacaaagaaa ttgtggtata tctatacatg gaataatact cagcaattga    58620
aaagacagtc tacaaatgga caaaacctca tggattcata tcaaaaaaca ttataatgaa    58680
caaccaaaag cagatacaaa aatatgtaat gtattattcc attagatga aacaaaagaa    58740
```

```
taattgatgc taatgcatgc tgataaaaat caggatggtt gctttcaggg ttgaaagttt    58800
gagttgaggg agatgcaaag cactttctgg tgtgaaggaa atattctaga tcttgttttg    58860
ggcggcagtt ataaggatat ctacaagtca aaactcatta aactgaactc ttaaattctg    58920
tgcattttat tatatacaaa ttattttgca ataagaatta attttttaaaa agcaataaaa    58980 attgctgctc ggcgaaaaca aattatgaat atactatcta acacacttttc tggtgtgaag    59040 gaaatattct agatcttgtt ttgtgtggca gttacaagga tatctacaag tcaaaactca    59100
ttaaactcaa cttttaaatt ctgtgcattt tattacatat aaattatttt gcaaaaataa    59160
ttaattaaaa aacaataaaa attactgttc tgagaaaaca aattatgaat ataccatcta    59220
actctacaga gtacagaaat aaaaaatata gtaatatctt tgacctatttt gaaagtcaac    59280 aaaagaaaag caagaaagtg cctacaatat gattaagtga atggcattta tatatatgta    59340
taatcattta aatgtttaca gtttaaagga aaaaatagtg aggaaaagaa tgctatggtt    59400
ttcaaatcct acggtttgta ctaaagttgt ttgtcttttt ttttttctta gctacctggc    59460
atctgaactc cctttctgtg cctgtgaaat ttccaccttc aactgcagaa gctgcaaagc    59520
cagatacttg ctttcatagc ctccattact ttgagggtag ggcacatgaa taggctcagt    59580
tactctgact tcagcttgga tattgacttg ggaactagtg agaaaagaag cactcagtgg    59640
agaattagtg ctggcagcaa tagtagcagt tacctcgagg atctggtcac agttatagca    59700 gggggggtcat ccagtagcca atgtcagcag caaacaatgc caatgccaat gctagagaaa    59760
tgagaggtac aaaccattca tctagcattt gctggcatca gaaaaaatat cctcactagt    59820
caagttctgc agcataattt tagcttcaaa gctatgcact ttgttttatc ctgcctgccc    59880 atttttttaag ccttttctct agtgttccaa atgactctgt gaactactca atatcctttc    59940
aacaaacttc ttttccactt gaatcatcca gagttaattt ctattgctgg caatactaac    60000
tctgatggaa aaataaaata ataaatgcac tctaacacag aataacgaaa ataatgctcc    60060
acctagttaa caaggatttt acaaacaagt agaagttatt tggtcttctt tttaaaaata    60120
cgttcttaaa aataacatttt tgacaccat gaattccacc tgtgttttca aactattttt    60180
cactattaac attatgtttt aaaggagata cgttttcaaa agatccactg gaaaaaatta    60240
gacttctcct ataataattt acacagtgag tggctgagat tctaaaggaa tatcataaaa    60300
ttatgataat attaaataaa agcaaatact ctcataactt tcaaggaaac atgcgatgac    60360
tgatgtagta tcaaagggat atgttttgga agatgctctc ttctatgtga ctgaaaatat    60420
ggggacatgc tatacattct atttttttctt attgattgtg aatttgttag tcatcaattt    60480
tgctgagtct attcaaaatt tccacttaca taaactcttt gagtaatgag tttcatagat    60540
atattgtgtg ctatgcgaac tagtacctct atttcttggt tccattattc ttgtactata    60600
ggatattgta aataaaccta tgttttctgt aacatatctt tgaaaaaat aatgcatctt    60660 ctcagaaaac ttttcctatc aagaattttt gttgttgctc ttcatcagtc taagaaaaaa    60720 ctgtctttttt tgtcctttttt tattttttgcc catattttcc tcttcatcct ccattcctat    60780
gctcatagcc catcctcact ggcaccaatt ctgtgtttaa tgtaaacgtc cttgaaaaat    60840
agtgttgttt catttcgagg atatactgaa gttacctaaa tttgaacatg atatggattt    60900
cattatttct tatcttgctt ttgtgaagat gacattttat ggagacaaaa gataagttca    60960
cacataaaat ttcaggtagt ggtaaatgta acaaggaaat aaacacggtg attcagtagt    61020
gattgggtta ctttataaaa gatggtctct tctcagaatg ttttatttga gctgagaata    61080
gaaacatata aaagatactg ttactagggg catccagacc aagaaaatgt tggctctaaa    61140
```

```
gcaagaatca gtttgataca cgagacaaat ccaggaggca actactctgt ctgaagcaca    61200
ctcagcacag aaaaggtggt cctagatgag gcaggagaaa ttggcaagga gtgggtcata    61260
tagggtcttg caggctacaa ccagaagcaa gaattttact ctaagaacaa tttgagagcc    61320
attggaaggt tacaaagcag aggagcaatg ttgttttttta tttaaaaaga taggttgctg    61380
tgaaaaaatt ggaaatcatc gaagaattaa tgggatttct tgtcaagagt atcagattct    61440
atcttcattt tcttctgctg tcttccaaaa tcccattaaa atgacagtaa agatataggg    61500
aaaaaaatat atatccatgg ggagaagagt aggagaagtt taatgacaac actgttttga    61560
agcctggaaa gcaaattaat tagtagttag tccaaagcta tcattggaga aagcagagta    61620
gtaatgcatt tcatactaca gaaccacaga aagaatcaag aactggtgga accaagcgcc    61680
tccaaaagtg agaaagatac agttggggag gagaagtagt tgacgctcca tttaccaatc    61740
atttagactc ctcgttcctc tcctacaccc aaacagaagc ttagacattc attcactgga    61800
gaggataaga tagagtgtct ctagaacagg ggctaccagc acagttaaga atcttatact    61860
gaaaattcat ccccagtcct cttctcccaa tgattctcag gtttacacct tccagggtga    61920
ttggaagatt cttctctggg gatctaactt gtcattttgt tttccagcac aatggccgca    61980
cttgggtcag cctacaggaa agaccatagt caataagccc tcctcagact caagagcttt    62040
ttaataagta ttcaatcctc tgttcaatat gaacaattaa aaatcaccag actttagagg    62100
aaagcatctg ttatgaaatg cagagagtaa ataggggggaa aaaaagcagc ttggaggaaa    62160
tagactatgc aagtagatga aacctttaaa aaaagaacta ccattaatat ttttattgat    62220
aatctcagaa agacaaaaga aaaaaatcac attcacaaaa taatagtggt attcaagaaa    62280
aattcagaga acaagaatgt gcttttggaa attacaaatg acagaaaaga aaaactcaat    62340
agaaggctta aaggagtaca ttaagaatac atcctggata tgcaaagata cggaatatag    62400
atcagaaaag ctgccctcct atatagacta gagaatcaat atgttaatgg tctgatataa    62460
taagattccc agagagaaac tgagaataca aaggataaaa ttaataaata tttggaaaag    62520
atttcataat ttaattacgt gagtatttaa agagcacagt aaagcatact gtaatataag    62580
acttacagtg aaatttaaca cattgtggca ataggatat ctataagtat tcagagtgaa    62640
aataataaaa tcactaacaa agaaccaaga atcaaaaata gactggagtt atcaatactg    62700
aaatttagaa aaacaaacaa acaaaacttt taaaatattg aaaaaaaatc catccaagaa    62760
atctatactc agctaacctt ctaattgtga gggtagaata caggtatttt ggatataagg    62820
gtctcaaaaa ctgtatgcat cctaaaccgt tccccagaat attactgtgt aatgtactcc    62880
tccaaaatga ggaagttaac caagaaagag gaagttatag tatacacaaa acaggagacc    62940
taacatatga aagagagaga ggatacagga tttccccaga aagatggtga atgtgcccag    63000
cctgacaatt gtttggatgc agaagtagtg gtagcaaata ttttggttta tccagggttt    63060
ggggttttct aggtaagcac gatggagaaa cagacacatg aattgacagt gaactctttc    63120
actgtcattg ttacaatgag gaaatattaa aaccattctg gataagaata aaagtataga    63180
ctagaggaga atgatagtga acaagtagca aaatcaatgg tttagaagtc ctgaagagat    63240
agaaaaagtt tctagagagc aagaactagc ataaatgagc taggaaagga ggtggtagtc    63300
agagacgtta aggtgatcaa gatgttagag aagatatagt ttctagtgat gaccaggaa    63360 tgtgtggttg agggaaggaa atgtggttgt caaatacaga gagctcagaa tgctggagtt    63420
atctgcacca ataatgaagt cacccatagg gtgacacaag tagaggtata aagaaagaaa    63480
ggccaacagg aactaaagta ttcaattaat gcagggaatg aattaagata aatgacctat    63540
```

```
aaattcatgg ttgacagcag cacgaagggg tagagcataa tatatccaca tgacacggct    63600
tcaaataagc tggggcattt ttgaagaagg acacacctat cccaaatcct agccttgaag    63660
tgcaagagga atgatagaaa acaaaaacaa aaacaataa ccctcactag aattggaaga    63720
tttatcctta attaatgtcc agttcagtta aggcaagaca atacgtagaa ttttcagaga    63780
caaaattgct gatataatag agttttctaa tcaagaagt ttgcagagta gaaggttatc    63840
agaaggtggg ggatttatca acttagagat atacaaagga tgtaggatct gccagggaag    63900
aataatgatg ataatggttg atagagaggc attgacttct ggtcgtacta gaagtaatta    63960
tggatgtcaa gcatggtcaa agtcatcatg gtagtctcga agaaccctgg gcattggttc    64020
actgggtagc ctttctattc aaagcgcggt accagggcca gccgctttgg tatcacctga    64080
aagtttgtca gaaatacaaa attacaagct ctaccccagg cttaatcaat cagaatctta    64140
ttcaatctga ttgattctta atcagaatct tattcaatct gattgattct taatgaatca    64200
aaatcttatt caaactgatt gattcttaat caatcagaat cttattattg tgtgtacaaa    64260
aaggtttaag aagcattact tcaattattt acctctaaaa tatggggtgc ctgttttctc    64320
ctctagctcc tgtcagtgga ctcaccagaa gttgaatatg ttgacttcat catgggacta    64380
tttctcttta aaacatcatt atgagaccac attggtgacc acattactaa actataactt    64440
tctccgcctt cagatgggga ctattttgta tattattagt gcctggtgcc taataaaatc    64500
ccaaaaacag acacaaaaaa tttcctaggt gttgtggaag cctagagagc gagagggact    64560
aggcgtgcag gaggaatctc ttttgcagtt gggctggtga tgtggaaaaa gtaggactgt    64620
aggactggaa aagggaagat tgggtaggtt gataatttgg aaaaggtaat taaaatataa    64680
attcataaaa agatgtcaaa tattttaatt taaaatatac acactacaca cacacacata    64740
cacactacac acacacacac acaatgccac atttgtatgt gtattaattc cttcacagat    64800
attcttttgt agggcccaag gccttttatc tgagtatgaa ctggtttctg agagttctgc    64860
aaacatcttc cttgcacaaa gcatactaaa aatgcattgt ctaaagatat ttatttctgc    64920 tgtcttaaa gtgaattgtg aagcaatctg agtacagaat ctgcctagtt ttttgttttc    64980
cctatctttt acaattctca tctacacata acagcatttt aaaaatgatt ttttctagt    65040 ccttccgata aagtcaacct tgtccttttt gcacttatat tttgatggta tataaagtac    65100
ttaactaaat tgtccaatac tagtctctgg taatataggg gcttaaaaaa tccatcatca    65160
ttggttatag taatgggcaa ttttagtgtg ttgcttattt tctcctatag ttaactctgt    65220 gatccctct cagatttcag tgaacttgcc catcaggtta accctagtgg atctggcagt    65280
gcagcttacc aaccgagagt tcttaggact tggtgctctg gaatgaaggc agcatgccag    65340
gtcttctgta gcaaccagac catttgccat ggcagcttca aattgagcaa gaattccaca    65400
atttcacact tgagtgcagt taagtctcag gtggatggca gccaggttcc ataaataact    65460
ctcggttatc attgttccaa aactcaagac ttttaaaagg cactacctac cctaaaggtc    65520
cagtccttaa tgacatgatt tgtatgacac ttgagcaata gcctgaggct gccaaatcag    65580
gtaagaagga ctttcccata ataatatcaa cctactctaa gtagatttca gttggatcat    65640
gatatatcaa catatgagtg atacatgcag ggcactcact ttggtttttt tgaaaatatg    65700
tttaagttca tttatgaaat attttgaga ataattttg tgtttagaga tataataagc    65760
tctaagagaa atatatgctc atagatattc atgcctagtg gtacttacct tctactttaa    65820
aattatttgc ctttctttct gacccatgag acatagctca aaagtaataa caagtcttac    65880
tctgcctacc atcacttctg atatggtttg gctgtgttcc caccaaatgt catcttgaat    65940
```

```
tgtagctccc ataaatctca cgtgttgtga gaggggccca gtagtagata attgaataat    66000
gggggtggtt ttccccacac tgttcttgtg gtagtgagta agtctcacga gacctaacgg    66060
ttttataagg ggaaaccact ttcacttggt tctcattctg tcttgtctcc ctccacgtaa    66120
gacatgcctt tcaccttccg ccatgattgt gaagcctccc cagccacgcg gacctgtgag    66180
tccatcgaac ctattttcct ttataaatta cccagtctca ggtatgtctt taacagcagt    66240
gtgaaaacgg gctaatacaa cttctgatag aaaattaggc acataataca cattagttga    66300
aataatcaac tggagaatgt aggctttttt ttttttttt gaaagagtct tgctcagtca    66360
cacagactga agtgcagtgg tgtaatcata gctcactgta gcctcgatct cccaagctca    66420
agcaatgctt ctgcctcacc ttcctgtata gctggaacta cagatgcgtg ccaccacacc    66480
taggtaattt tatttttaat ttcattttt aattttact ttttgtagag atgagatttt    66540
gctatgttgc ccaggctggt ctggaactcc tgagctcaaa tgatcctccc acctttgcct    66600
accaaagtgc tgggattaga agctgagcca ccatgtccag ctcagaatgc aggcttttta    66660
atacaaattc aaacttacaa acaaacaatg agaagatagg gtcaataacc agtatatgct    66720
ctttttcgta cagctgaggc tctgccagat ttaaaatatg aaaccgatcg tattttactt    66780
cgggaacaag aatacaggag atctaaatat aaaatgacga aaacaaaaa aaaaagtgg    66840 taaatctcct aagcaagcgt caaatttttt taaaacatca ttctatcaga tgcttaagga    66900
actttatcag aaattaatac aaaattttct aaatattgaa cacaggaatt ttgctattcc    66960
tcattttttg tgccataaga aatatctgat ggttttacaa acaataggcg cttagaaatt    67020
cagcatacaa aattcatttt cccccaccta ttatcaatta cagattttac ccaaaagagg    67080
aaaaaaactt aaccaaatga ttacaatagt gttgaggatt ttttattgtg ttttccacat    67140
agataaaaaa ataaggcttt ttgatgaaaa gaatccatta caaagtcaaa aatccattac    67200
aattataatt gaatcagtaa caaaatttag ctttaaatga gtcaagtatt ctgcatttga    67260
aatttaatat cacaaacatt caagattagt gaattttggt aagaaaaaaa tactagaaga    67320
aaggaaaagg acaccttttc aacagatagt aattttataaa aattttttta aaagtgcttt    67380
gggaaaacac acagtatcat tacttaagaa aagtcattta aggaagactt aagtgcttca    67440
agtggagtgt attacagact aaaaaatgtt ttaaaatttg ccaagaaatt taagtgttaa    67500
aaatactctt ctccttattc agtttcatgt ttaaggaaac atttgacaga caagtaaacc    67560
aaacgcaaaa aaaagttcac ctgcatttta aactaataaa ttctggatct gtaaaagctc    67620
ttggtttgta cacagaggcc aatgctgaca tttattgatc tatttttatg tagttaaaaa    67680
aatacagtaa caaatctttc ttcctatccc cccaaaaaac tagggaaat atttaaatt    67740 gtgagtgtgt gaatgtagct atatatatat atccctaagt gtacaaaaca cacaaacatc    67800
actttacttg gaaaattatt ttcatcatac tgtaaacatc tcttcccta catctggaca    67860 ttttgaaata gtctttggta ttactagtta ttgtgctttg aaacagaaac ttgcagaatt    67920
tctgtagtag tgctacataa agatataaat aagaaaatg cacttggaat aagttacatt    67980
tagctgcttt tgcataattt tcaaaaacta cagtgtatgc ctagtcacag ttttatgaga    68040
aagaatattt ccttttcaa cttaatttta aggaacactt aatcattttg gctaagtatc    68100
cattttggaa gtggatctga tgggttgcat gacactaaac ttgatgctc tccatttgct    68160 gaaaggcaca tttttaagaa tggattgtat agaagttgat cctagaataa aaggaaacaa    68220
cagacattaa attccaagac tcatagttaa gtgacaaata tgaaaagat tttatggttt    68280 cattgaagca aacctaatag caaatctttc taaggtgagc catgtctgat aaactctttt    68340
```

```
tggcttctag tgtaaatgcc accttttaag ctactactct tcaattagta agatattaca    68400
taatgaagag aggcagacag aacaaggttt gaatcacatt ttcaaacaag aagtattccc    68460
ttgatatatc cataagtgac aaactcttaa aaacatcata aattataaaa gccagtgtta    68520
acgttttcta gtactgcaca aaacaatgtt caggtaagaa ttgctatgat acagctaagc    68580
cttaaacatg tttaaaaaca gaagagacct gttatgtatt ctctcaattc taggtttgtg    68640
aaaaagtgct aaaacagggt agaaaaaaat taatcacttc aagtgagaag atataataat    68700
ttttcttctc tctgacagaa aaaaaatatg actgttgcta aaagcattat aagaaaccct    68760
aaatagtaaa aaacaagcga ctaatattaa taattcacag aagtgctcat ctgcatatat    68820
cacggttcaa ccaagcaact taatttttg ttactaagag tacttaattc atagatatat    68880
tctcttatca catgggtaga aacacataat aacaaagtta ataaagggag agaaattctg    68940
atagataata ttaatgtacc atgttccact cattttccca gataagcaag tagagctaag    69000
aaaaatagtt aaatagatga attaattgca ctgaggtacc ttctggatct cccatatctg    69060
ctctccagtg acaactgtct tgtgaccttt gtaggtacat gccttcagct gaacgagacc    69120
ttgagcagca tgaagacata attccttctg gatgttgtgc cgaatttcat gttgagcaga    69180
gtattcaaag tactatggaa ggaatagcac tgttactgac aaaagcaacc catgtgctca    69240
gttgcaaaat aaataataa atcagcaact cgttaaataa taaagtcatt tctatttcaa    69300
caaaataata caataaaaat agttattaga aacataagct gagttttgt gatagacgat    69360 acaatagcct tccttcatca acaggtggtt acttcattaa caaggtgctg tcttcctccc    69420
cataccagaa gttggaagtt atcaaggaga gtggaggcta tcccaggcat tcctcagaaa    69480
agggaatgaa gagttataac aagaacatta attgcctctc tcccacaagt gttccatctc    69540
tcttcttcat ctcaatcaaa ggtgttttca ctaaactagg gacttcaggg tgttcaccat    69600
gcctcagttt tctcactaga aaatgggtaa tttaatagtt cctacccac agggttatga    69660 agataagtgg gttaatacgc ataatacatt tagaacaatg actggcacac ggtgagtttt    69720
catacatttt agctattgtt actactgatg cttctctttc tccacatatc caagtaattc    69780
gtcccttagc tgcactattc ctctcagatg ttaacatccc atccattctc acttccgtgt    69840
actcacttct gttactcaga ctctcagaat ttttactgaa acacctacag ctacttccaa    69900
tttctgttcc tatcatccag caatccaatc tgctgccaga tagtctttta aagcattggt    69960
ttgatccctg actgcccttg cttaagtgaa tcactactgt tgctaagata aagtccacac    70020
tccttaattg gtacatgaaa tctttctttt tgatcttgca tcaatcattg ccccagttat    70080
atattatgct tctttcacac aattctacca atcagaacat atgtatctat aactctaaga    70140
ctttgcttta cagtctgtcc tctgcctgga atacactttt gacccttttc tgcctggcta    70200
actccttttt aatccttcaa gagccaactc aaatactacc ttccttcttt ggctttgcct    70260
gaatttgccc tgctgcacaa aattacaatc ttttcaaggt tcccatagta catcagagat    70320 aactttcta gcactctatt agaattgtgt gtggtgtgta gacctggctt ccccatagac    70380
tgaagtcagg caatttatcg agtcataaca cccatcacaa atccaatatt tcataatatt    70440
gacattataa agataaaata agttaacata attgattttc aataatgaaa taattagtag    70500
gagcactaat atttgttaag tcctattac atgttaggca ggcactgtgt taaactcttt    70560
atgtgtatta cagtaggcac tctacaaaca ttcgctgaat tcacagagcc atatatcttg    70620
agtttcccta ctcttagtct catgcttaat ttatctccgc ccacaagcaa aacatcagtc    70680 attttttagaa ctagtagttc ttcagatgga aacacaggaa gaaactgagt ttagatgatg    70740
```

```
aaaatagcat tctagctata cttggctaag aaagataagc cttaagatct caaaaatggt    70800
aacaaaggct gtcgagtatt ttacccatta ttaaaaagtc attaaaataa aaattacaaa    70860
aaatggaaaa tattgaaagt actttggtaa caaaaaagag cacataattg gataactgtg    70920
aatgttggag agacccatta cttagaacga gtagagaaga ggcaaagcag taaatataat    70980
caagttataa tgactcaaac tgcattacac tagtaatatt ggccagctta gtcacataac    71040
caaaatattt atttttattt ggcatacatg aagttttatg ctataaaaat attatctgat    71100
caaaagtaga aggaaacatg aaaaaatgat caagttatat aatatctaaa aattttagca    71160
ctcagggaac taaaatttgc aaaacggttt aagtgcaatg cttgattaaa aataaaatgt    71220
caaggaaata aagcaaaata aaatcaatag ctgtgttagg gtaacaaaag ctgaagtttc    71280
tatttagtat atacaccaga taatatttat tcttctgctc aaaactcttc aattgtttct    71340
gtcaaagtca gaattaagtc caagtttctt aatggggcca gttaagccct acatgatcag    71400
gtccctatca atgccccgac ctcatttcct agtcctcttt gctagaccac tctgctctag    71460
gtacactggc tatctgcttt ctccatgtat ctgcctctgg gcctccactc ttggaaatcc    71520
ttcctccaag atgagcatct tctcctggaa cactctctca cagtattcag gcctccctct    71580
aagatcgctt ttccaaaaag gtcttccctc acctcttaaa ataaccaccc taccccgaaa    71640
cacactattc ccttacctgc tatatttttc ttcatgccca aaactacata ttttttttctt    71700 tgttcctgtg gaacataagc tccacaagat caggagcttt gtctttttac tacggtaaca    71760
gtcagtacaa gctactttat aggttctaaa caaacactta ttgaaagaat atgtgaatgt    71820
tttcccatcc cccaatttct aaaagatagc tatattctat ttaaaatgta aacatatttt    71880
tgatacagag ctatcataaa gctgttatta tctttatgaa aatgataaca gaaaaatgga    71940
aaaaagcaat gtgtacaata tatcttcagc ttttaagata aaataaatgt aatgctagaa    72000
gaagcctaag agaaatttat agggatttac atttactagt aagatttttaa caaatgcaga    72060 aatatttccc tttgctcaaa atcttaattt ttacaagcat agatcagtgt tatttccaaa    72120
gaatgcaatt atttatgtaa ctattttttct tctaatatat ggagggtaag aaaattctta    72180
aaaagatgca tatagattta tgcacataca catatatgta cagatatata tgtatataga    72240
tataggtata gatgtatgtc tgtctatatg catccatata tatctccatc ctatttcaga    72300
attacacctt aaccatccag caatagatcc agttcaccag ctctggcttc tgggcatctg    72360
tatcatctgc cctcagtaga ttgattggtt taggttaata aggattagaa ctagattaag    72420
ctgagcctaa tgggtaggaa gaaatataga agaggatgga ccaggagata aactggctct    72480
tttttcctaa aactgacatc tcaaagtttc gtcccattaa aataggacat catggatatt    72540
aattattgca aaaatcctcc acacacatct tggactctac accaaaatac ctgcaatgcc    72600
cagaagagat actccaggct cttctcttca tttcactttc cttcacactc ttcttattct    72660
gttgccattc cccacagcca cctcactagc tcctacctac tttttttttt tttaatgttt    72720
tcaaatatca tctttctcag gaaaatgtgt ggacacccag tctcattcaa tgcccttttc    72780 tatacccca gaacactctg aatgctttat cctaaggaac tgctagttta tagatttcct    72840
aaaggagtta gagtctaaat agcttgaact catcagagta tctggcatgc agggctcact    72900
caatgaattt gttgaatgaa caaatgaggg aaatagtcta atctttccag gagttaagct    72960 gcaaaggta aggaaaggaa gcttaaaaaa acagaaactt tgtatataac atgttctcta    73020
cccataggca agtaaatagt aatatttgac atgtgaatct taatcagtaa aatagtcaaa    73080
aggtagtaaa gcaggtatgt cactaatcaa ggagaatctt cctcttttgt tggagaagga    73140
```

```
ggaacatatt gaaataatat tgtgggccac aaaattaatt tataatgctc tattttgtta   73200
ttaacacttg atgtaatttg tgattcaatc cagttatatg tggcctttat gtgtaaactt   73260
gcaaaatcac catgccaata gtcatgcaaa agtaaagca tcaaagagct acatagaagt    73320 ttcttttta aaaaaatttc aaatggcatt attctattat tttctcattt tccttttttt   73380
ttttttaatt tgtttgtttg tttttgagac agagtctcac tctgtcaccc aggctggacc   73440
gcaattgtgt gatctcggct cactgcaacc tccacctccg tggttcaagc aattctccag   73500
cctcagcctc ccaagtagct gggaacacag gcatgcacca ccacgcccga caaatttttg   73560 tattttagt agagatgagg tttcaccata ttcgccaggc tggccttgaa ctcccggcct    73620
caagtgatcc acccacctca gcctcccaaa gtgctgggat tacaggcgtg agccactcag   73680
ctcggcctcc tttttttttt tttttttttt ttttaatgg ttaagctact caaattgttt    73740
tcagagccag agtaaaaacc aaaaaaaat actcatcaat atcaattgcc aaactcagtc    73800
tgaaaacatt tcacacacag cttacccaag tataaagctg ctgtgggact tctgaaaaat   73860
aggcaacatc tcacttgtgc ttgtaaatgc tttacaagtg aaggattttt aatgcagtgc   73920
tcacctggtt tcccccaagt ccatgacatg tatacataat taatggtttg cctccttgat   73980
tgttttctcc aacatccaga catgaggct gaccaacgct tttaatctaa aggaaaattt    74040
tcaagttatg aaaagttttt taatccatgt gatttatata ttttttaaaat aatttagaaa  74100 gtaatgttaa tgattataat gtaaaatctc aaaagcaata agaaagtat ttcagcaatt    74160 ttcttagaac cacataaagg ttggtggcaa ggagtatatt aattaaaaaa ggaacaggaa   74220
aatactcacg tatccagata taacaggatt aaggtctggc acatacacct ctggataaat   74280
gttgttcaga taccatgtaa aatttttaca ctgaaggcgg tgttttattt caaatctttt   74340
tgaaagatca ccaaatgctt tctgtagaaa catgagaaat gaagggaatg cttaattaaa   74400
acaacattga taaagcactt aaaatactct tatttgtatt tctatttagg tatttttaaa   74460
aatccatgct aaaaattcaa gaggcaattc aacagccttc atcattcatt caagtaaaaa   74520
ccatgcctgc ctgttcattt ctggctttaa aagagagtca acaccacttc agtgctgatt   74580
aaaatactaa aatgatgcta ttttattctt catttgtgcc acaaacattc cctacaagac   74640
aaagatttct agtaaaatgc tgtgggcaaa ggaatggtgg taggagcatc caaaattggt   74700
cccaacttta tacctaaaaa tgatctgcaa agtgaggtgt cagaaatcag gtatagacaa   74760
acagtgccaa tacacaatgc aacttctatc tcttctccat caagatcaca gaaaaccacc   74820
agcaagaaat aacccactgg gagtaatttt tctagtttca ggatgttgct tgttcttaac   74880
aatatcccca actgaacctt tagtagaaaa aggcaatttt caagttaaat gaattttgct   74940
ttccttcatt ttaacgtact aagaaaataa cttttttaaa aaaccattat taaacttcaa   75000
ggtatttgac ctacaggcaa aatattagag aaaaagtaca tgtaatatct aaatgtatgc   75060
aaaagtaaat actcaatctt atcagttcaa ctaaagaaaa tattttctta tgccaacttt   75120
gatgtcttga acccaggcgt tttagcaaaa agtatgagtc tttaggactt ctggctagct   75180
tattacattt accatgtaga tctatgtgtc ctgtggtaac caacaggtat ttgctgattt   75240
atgtgcccct ttgtggggga caagcagagc ataagcttca tttagtgccc acttgcctgc   75300
ttagccaagt actattgtac agtacacaat ctgcccaatt tgtcttcatg gccttgggta   75360
aaaagatagc aatctaactc agtagtgctc ttaatttgca tcctaacagg gagatactgg   75420
agaccagaga aaaagggaaa gaggtaacca aatcgttctt caccgcaaca gccaaaatat   75480
tgatacccct gactcccaat aaatactcca ccttccctca ccctgcaaat tagcactatc   75540
```

```
tatttcctac aaagagatga gtactataca ctgaagcatg gtcttaaact atctagttaa    75600
tttaccttat ctaatattat taagactatt ggaactcact tctaatatat taggtttcat    75660
gattctgcag agcagaatct atttatggca ggttaataac aagagtacca tatatttgtt    75720
agcacttatc actttcttat ttcacagcta ctctgggaga gagacagcat gcgtatttca    75780
tctcttaaaa cagggaagga gagaaaagaa atatgttaag catgcactcc atgtccagcc    75840
accttgcagc cactctatga agtgtcttcc ctattttaca ttctcaaagg ctttgccaaa    75900
gtaacatctc cagtaagtag tgaaactaga gcttgaaaaa aaaaggcttg gcactcctgg    75960
tttattctca tgccacatta agacactgtc tctatctcca gtgcaaaaag tcacttagaa    76020
cctttattta ggtgttatat ctcctaaaac cagtaaaaac agttctactt aattttcttc    76080
gagtaaaata ttgaaccagg gcagcaacaa aaatgaacta tctttcatat taaaaacatc    76140
aagtagaatt cctgattttt aaaaagcagt ttacttagtt ttttttcttaa aaaaggaaac    76200 ttggattcat aagtcatgta ctttaagagt taaaaaccta ctttcaaatt ttttgatgtt    76260
ttgtacttga gatgaatcga cgcaaaagga cgtgtgaact tgttatagat tttattgcaa    76320
tttaactact tagctttaac ttacttgttt aacaattttt gctgcatctg tatttctcct    76380
ataaaatatt tccttgtatt catccatcca gacttctgca aggcgaactt ggtttctagc    76440
aatcacctga gtgcctttg gaaagctatg agggcttttg ctgcgaaaaa catgtccaac    76500
aacagagcaa ggcataatct ccaactgccc accacattgc catacctgat aattaatgat    76560
atttgtttaa atttacagta ttttagaaaa atcaaagtgt tgcttttaag ttcacccttta   76620 aggtattatg aaaaacaaaa ttagagaaga gattacaata ttacaaatag tctctgtccc    76680
ctgccatttc aacttaagtt cttaagtgta aggaattatt ttattaaatg gcatagacac    76740
taaagacaac agaagtgcat tttcagtaag ttaacaaaat ggtgatttca gatttttcat    76800
aaaaatgaat tccaggcttt tgtttttgca ataattatg taagttctct aatatgcaca     76860
gaaaactaaa ggctcttatg catttgactt ctgtctgaac tactgacata gtcacttcac    76920
ttaaactaga gtttctcttc aaagtttgga tataagtgga ctcagaccct atttatctct    76980
tgtatattca attttgtaac caagaaaaca attccagatg gctattatta ccaatgatca    77040
ttctactgaa cttgcaaagt agaggatgat tattttaaaaa ttcatgccaa tttagagaga   77100
aaacgtcaaa aaaaatcctt attggcatta atgctaaata aaatggcaaa tcatgaaatc    77160
aatgcctttt cacttaaata tcttaataat tgactctgcc atagttacca agcaaagaat    77220
cagaaaataa gtcatattta atactatgtg cttgtagtag agcaagtgat tacaaatctc    77280
tttctctcct ttctttcttg aacaaatgag aagactcagt gatatgttca attcaacaaa    77340
ctgtgcttgt gacccaacac gtgctagggg ttggaaatac tgaaatgaat aaacaagacc    77400
ccgccataag cagttcaaac ttggctaaga tcatcactgc cagtatgtga tggagccaga    77460
gccaaaactt aaatcttcta actcctagtt cagttctttt tccactacat tccagcctaa    77520
gagatgaaaa atgaatgata aagttactgc agaaaatgaa actcatgaaa tcaaatacat    77580
aaggtacata cggagtctac ccaaagccct tttttatatt aacttataat atgtatagaa    77640
aaaatcaagc tcattcattc caaacagtta agtccaatgt cctttaaaat tattcataaa    77700 tgttttttcca ttctaactcc cttgatgatc aactcatttc ctgaagcact agatttaatt   77760
atatttatct tggctggaat tcagtagcta caagtgcatt aattggtgtt actgcctgga    77820
cacaggagtt taactgattc ctcttgttac actggcgaca atgaataaat atattaagtt    77880
acatattaaa agaaaatatt cttattccaa aatttccagc aattaagttt cagaaagcac    77940
```

```
aaaaagtaga gtgcacacat ctgtaatcat atgtaccagc cgattagaac acaatatatt    78000
tcattgttta atatatctgc tatatttaat ttccataaac ttactctgaa agacatttct    78060
atattttcac ctccccagat ttccatttct tcatcatagc ttccaatata ctcaaaatat    78120
tcttttgata tggaaaaaag tcctcctgca aaagtgggtg ttctgaaaaa taatccattg    78180
tcaaattttg ttataaaaac taaacaagat aaaacagcat attttaagaa ctgaagttaa    78240
aaaattaaag ccatatcaca ttttcaaagc ttttattcag attaataaaa actagaaatg    78300
ctatcttcaa agtcaagatt tttggggtcg gggggagtac ttcgtgtcct ctcccattgg    78360
agtaaactta aatgtcttct cctaaccatg ctttacgatt tttaagtaat gattgatgag    78420
gaagacataa gagctcactc actgctacct cttactcagc aacatcatgt ataagcaagt    78480
acacaaatga atgactttta gattctcttt atatagaata tgtgtgttct ttatcaatta    78540
cctcagaggc aattgctata aagcaaacag tgtgtacata ttcaatgtat ggtatagggt    78600
gtaaatataa gactctgaga gcaatcatct tacttaattg ggtaggtttc atctttcctt    78660
ctttgcttct catgatcagg aagcgactcc cagccaaatg aaagactcca gtcaaaattt    78720
ccacggttat ggttacttcc ataaggagaa ggtttgttga attcaaacgt gttcagatct    78780
atggatgcaa tatctggact tacgacagcc gtgtagttct cagctattct ggccaacaga    78840
ggttctagcc aaccatagaa acactcacct ggagggaaca gaattttaat taattcaata    78900
aaaacattga agttttttc tttagttatt taggtgaagg tttacagaga aatgagaata    78960
acagagtcaa tttgtgtttt gaacatgtat ataatggaga tttctttctt cctcagattt    79020
attgagatat aacaaataaa aattctatac atttgcagtg tatatcatag tgtttatata    79080
tgtatacatt gtaaaatgat tattgcaatc aagctaatta acatatccat caccttatcg    79140
gcttatggag cgggtggtaa gaacatctaa gatctactct tagcaatttt tgagtagaca    79200
atatattatt attaattaca gtcaccacgt tgtacaatag atctccagaa ggggagattt    79260
tttaaaggtt tattgtgatg agatgagggt aggatgaaaa aggtgaaaaa agattcacta    79320
cagttagaaa aattccccta cagatgatga ccttctttct tctacaaaag atgcaaaata    79380
acaccagtgt atttaaagtt tagatgatgt gttaaaatgg cctatgagtc aaaggtagct    79440
ttttgctgtt ccacattacc tggccctaaa agtgttctga tttatttaaa ctcgtatctc    79500
cctgaataag gtacagtaat tgaaattttc atttatctga ctgggtctta ggagaaaata    79560
aggagtcagt ataaattccg attttagcaa ctggagaaga aggaccattc aaagctgccc    79620
cagacctaat ataagggag ggccaaggag tttcatgtca tgataggtct aagccctggt    79680
cacaggccag gctgttttat gtaacacaca gcaagttcag ccaatgcatg tgctgtccta    79740
ttctgggctc cccacaaagc agtatttggc agtcatggtc cggaggacc gtcagacata    79800 tccacccagt gggtagtggg taagaatgtc cagtatgatc ttattgtaat tttgaacaac    79860
gagaagaaat accagaggat ggtattttcc tttttaaagc acctctctag cattacccttt    79920 agtgttctct tcattttcta aatgtctggt attaaaagag aactgaatgt gatggctcta    79980
agcaacacaa gcacatccaa aagcccttct gtaataatcg gtgtgtgctc aaaactagta    80040
attgggtgaa acataaccta agcactggcc aattcaaagc tagacactca tacaaagtat    80100
agcccactaa actcagagct caagggacaa aatgacagtt tagtaataac tagcatgcat    80160
atgacacatt gactctaaaa atgctttcta aatacttcaa aaactttgac tctgaaaata    80220
attaaagtac aaagaaaaac caacagcagc aaagtcaaac aaaaattgac aatgtttatg    80280
taagggatac caaagaagat gggatggggc accctaacc tggcataaaa agtatatata    80340
```

```
taaacatatt ttggttttgt ggtttttatt gaaaattcgc agactccttt ttatgccaag    80400
gagtctgcaa atttaaaaaa aaaaacacac acacaaacta aaatataaaa aaagcagcag    80460
tactaggacg aagtttaatg atagggtgga ttatattcac tcactcattc attcattcat    80520
tcattttgaa acggagtgtc actctgctgc ccaggctaga gtgcagtggc acaatctcag    80580
ctcactgcaa cctctgcctc ccaggttcaa gcgattccca ttcctcagtc tccctagtag    80640
ctggaattat aggcacatgt caccatgcct ggctaatttt tgtattttta gtagagacag    80700
ggtttcacct tgttggccag gctgatcttg aactcctgac ctcaaatgat tcaccaacgc    80760
cggcctccca aagtgctggg attacaggaa tgagccacca cgcccggcta catttaaata    80820
gtaaataagc tttcattcac tttaaagtgt gggaatcaag aaaacaaaca aacaaacaaa    80880
caaacacttt ttttttttaac agaaaagaaa catggaaaaa aaaaaagag gcaaggataa    80940 ctggctggaa cagctagtaa ctggagaaca ctgaagttga ggaaacttaa acacaaaagg    81000
agataagaat tctgcataag tgaaggaat tttctccaca gagctgttac ctgcttgggc    81060
tgtcattgct ataatcgcca gttgaaaacg ctgttaaaga aatgcaatt aggcatttag    81120 aaaagaaaag acttccttac cttttaaatt agagggagag ggaggaaaa tgttacaacc    81180 atatccatac atatatactt acagtgagca tctaaaaatg tgagcgtttc agctgttgcg    81240
actgttgctc ctagcaaccg agcagtgatc agacctttc tttctctttg tctgactatt    81300
tttactatag aaaattgttt tacatattca tctagtttat catgtaagta ctctgtaagg    81360
aaaaaaaatc agggttaatt cttttctaaat gcattttcat atatagctta tgaaagctaa    81420
tgaaaccaca gagcaatgat ccttccaaat tcataatctt aacagttgca tgtgtccttc    81480
cagcaaaatg aaaattttat ctttaactcc ttactgggga aaaaggctag ctatgcaaat    81540
tatcactact gtaacacaaa acactgtaat gcatacttat tctgtacact tcctatcaat    81600
aaatataatg tgtttggagg gaagtgagaa acttcaaatg gagtcaaccc tagccgttca    81660
aaagactcat ttagaggtct gagaagactg actacaagag tgaaagatat ggaatttggc    81720
caaaaagata ttcaatgctt tgaaattggt atttaaatct ggaaatctta agaaaaatg    81780 tcaaatatct aaagacctct gatatttaag caaggatcaa ataatttaa caccaaaatg    81840 ttgagccacg tcagaaagtc cacagctata gcagtttggg acgattccta cacagagtca    81900
gcagaaaaat ttgcgaaagc tttggagtct cctgacagtt ttatttagta aaatatgaaa    81960
caggcaaatt ttagtattgg gtatatactt taagatattc aatataccaa attggataag    82020
gtttgtaata agcaaaattt gagatcatag gttttaaaaa agttattaac aaatgtcaat    82080
ccagtgttgt ttttttgtct ggttttgttt tgagacaagg tcttgctctg tcgcccaggg    82140
tggagtgcag tggcacaact cactgcaacc tccgcctctg ggctgcaagc agttttcctc    82200
agcttcccaa gtagctggga ccacaggcat gctccaacag gcccagctaa ttttcttt    82260 ctttcttttt tttttttttt tagagacggg gtttcatcat gttgcccagg ctggtctgga    82320
actcctgaac tcaagctatt tgcaggcctc agcctcccaa aatgctggga ttacaggttg    82380
agccactgcg cccagctgtt catattctga acaacttct taagcctgtt tttctcaatt    82440 aaattttga tttcttattg agtacaaaat gcagttcttc aagcagcctt cttgggccca    82500
aaacatagcc tcaaaaaaat ttgggaatgt taagaaaatc aataaatgtc ctggggcaaa    82560
agtttgcttc tgccagattt tagaaggaaa tgcagatgac tttgacttta tctgtgataa    82620
tataaccttt ttttcaattc tccagtggtt cagttaagag agctgcttat ttaaagctta    82680
aacattcata agagaggaaa gtgcaggaac aacccttgta gaaaaataaa tctatctaaa    82740
```

```
cactgttgtc tcagagtaat agattaactt tttaacacct tctaactacc tcaaaataat   82800
tctcagatta agcttttaac accttctaac tacctcagaa ataattctca gaaagacaag   82860
cagaattgta actcatctta aatatataat cataaacatt ttctgtttta agaggcttgt   82920
aaaaatttca acattcttgg ttagaattat tttaaatgga gttactacag attgcttcaa   82980
tataccctct cactgttgga atttgttaaa aaaaaattta cttacccaca acatatgaac   83040
ttcccgtaaa tttatatctg caccctaaat ttagctccca tgcacaccct ttatttggga   83100
ggttaagaac agaaagctac atgaaatcag atgccctgat ttcactttat ggcacaatta   83160
cttttagctg tgtgacccty ggcaaggaat tttaccttt ctgcgcctca gtttctttaa   83220
gatgaggata atcggactca ccatcacaag acattgctgg gaggataaaa tgagatatct   83280
gaccttcagg aatctaactc caaacttgga tttattaagg aataaatttt gtaatcattg   83340
aaataatatg tatctgtttg acacaatatt taaaatactt atgatgtttg aaaatttaca   83400
agttagagta tttgttaaat tagccttgtg attccaattt aaaatgtgta atttagtatt   83460
tgacttccaa ttttaagtgg aaatgtacta aagaatttga ctaacattgt aagtaatatt   83520
ggaatattta agaacaccga aataaaatag aacatggtga ctcttttta ctattcattt   83580 atattattta ttgatattta tattaactca ttcagtcttt aaaacaactc tagaaattat   83640
gtactagttc tgtatttcct caattttaag ctacacaatt ggattcttct tataatcaat   83700
ttcttataat caatggcatg ttaagtttaa ttagctgtgg gttttctcta gtgatttata   83760
aattaacaac acataatata tttaatgaaa tatggcatta ttcccatttt gctgataaat   83820
cacagcagag aggttgagta acttgcccaa gtcatatagt tggttaggaa aagagctggg   83880
attcaaatca aggcagcctg actcaaaggc tcaagtctgt gctcttaacc tctatgcctt   83940
actgtaacag tctcacattg aggactacat agttatgaat aatggtgttt catacatttc   84000
tgcatttgaa aatatttgaa tatgtccatc cttggattct aatttcattc accatacccca   84060 ctatccaaac tattatattc aagctctgag atggcataca gagagtacca cataaccaag   84120
tagactgtag ataccacaat atggatttgg gaaacaatct aatttgcatg tgctttctta   84180
ccatctacac tagcatcatc caccaaaatg atttccttca gcagtattgc aggtgaagaa   84240
tagagcacac tgtggacagt tctaagcaac gtggaccacg cttcattatg aaaaactatt   84300
atgacactgg tggtgggcag gggagggcag cgcttaaatt tttgttcaat acatctagaa   84360
gaagtcagag aagtagaaaa acaattacaa attttattat tttatttcac agctataccca   84420 ttgctaacat tatcattatt gaatctttat cactgaaaaa ggatagtttt cttgtatgtg   84480
atataatctc aatgctatat aaaatgtaaa taaatcaaaa caattttttt acaagcaaat   84540
cactcaccca gagatgatgt ctaccaacag agatgacaac atatcaagga ttacaacatg   84600
ttattatagc tttctcaaca atgtaatttt aaatgcaaat aacatttaa ataatgaaaa   84660 taacctacaa tgaggcagca tgtaaaaatg acaaacccctt ataattgctc aaataaaaac   84720 caaattttc ttatttcatg cagaaatcat tcattttttca tatttgcaac tttaaaaatt   84780
gtaccacttt attaattttt ttttttttat ggagtctctc tctgtcgccc aggctggagt   84840
gcagtggcac gatctcggct cactgcaagc ttcacctccc aggttcacgc atttctcctg   84900
cctcagctcc cgagtagctg ggactacagg cgcccaccac cacacccggc taattttgg   84960 tattttagt agagacgggg ttttaccatg ttagccagga tggtctcgat cacctgacct   85020
tgtgatccac cgcctaggc ctcccaaagt gctgggatta cacgtgtg ccactgcgcc   85080 cacaatatta aatcattttt ataaagatta tctttaatta gatatttacc taagtatgta   85140
```

```
atataggttt cttaagtatt tcctaggttt attgaatcaa tttacttaat ctatacacag   85200
aatcaaaagg gaaaaaatag ctttattgta aaacctatgt tcttcttatt tttatttaaa   85260
atagagacag tctgtgatgt tgcccaggct ggtcttgaac tcctgacctc aagcaatctt   85320
cctgcctaag cctcccatag tggtgggatt ataggggtga gccatcatgt ccagcctaaa   85380
cctatctttt tatgatgttc atcattcagc aaatacttat taagtactgc catttgccat   85440
gtgttaaaga ttttgctcca ataatttgat ctactatcaa ataagactag cgtttaaaaa   85500 aacccttaa aaatacgtag aaataaagat ctaaataaag acctaaatcc atgttaaaag   85560
tcctgtgctc atgtcaccat ctaaaacatt gattgggcac agggagagag accctaagtg   85620
cccttgactg attagtggta ctactatcca ttagttaaaa acattactta taaattgatc   85680
tcaaattcat ttgtatagga atgtctttcc tcaatgaaaa atatcttcat attaagccac   85740
tggggtgcag gagagtctgc atagtctcca gcctttgagg ctagagatgt agagataacc   85800
acagtgccaa gcctgctgaa tggaggtgag gattaaatga aagaacatat aggagagggc   85860
ttcaagtcac tgggacataa aataaaactg tgtgaggttt atgggaaaga taagcaaata   85920
aagcaactat atctttaagg tcacttaaaa accataaatt ggagataaaa gcccatcacc   85980
cttcagttcc tctgccaggg ccaatgggga aactgtagcc tccagtgtga tattaggggc   86040
ctgagaaaac tgccctaaaa aaagatacac aaattatccc attaattact ttcatagtca   86100
tacctcaata ggaatgtctc tgataccctt ttttaacagc aagtctttag aatggattat   86160
ttgtagtgat taaaaaaagg agttggattg gggtaaaata tcaagagaag atgtcaacaa   86220
cagattagaa aaaggagagg atggattctg agtgaaagtg gcattgctct tcagtttctt   86280
catgatttca aagcatgata caggtgcatg ggcggaaaaa ataagcacct tcttcatcat   86340
tcataaataa aaacaaatta tttattctaa attgaatttt ggataaacta ccaattaata   86400
aaaaagctca aacacaaact attaatatac acacttgaac cacaactaca cagaaataaa   86460
tgactaaata taagcttata ttttgaaccc ataaaagttt ataaccaaca taaactagaa   86520
gtaaaaatta tgaaaaattc catattgtgg tattttattt ttaaagaaaa aaaaagagg   86580 aaacctatga tttgttataa gcattttgag gagaaagtga aattctgagt ataagatttt   86640
tttcctacct ttatttgcta tgtggttaat taatatagta ttaatcgata attataaaat   86700
ggttttgaag atttaaagta taaaatttca caaaaattca tactagtaaa atgttatcac   86760
tttaatcttg caagattttc cgtcagttta aactaggatt tatttgctta actgataatt   86820
accaatatca agtacaaatg tcatatcaat acaagtaata aaatttcaca atataatttc   86880 ataaaccccca ttcattttga aacaacatgt taaatgtatg ctttgaaaat tgttttacat   86940
atttaaaata gtgcaattaa aataacttgc caaagtgact gtatcattcc agtcaaacca   87000
tttgaaaaac ctggcacata gaaacatgct taaattatca gtcacatgac catctggctt   87060
tgggagaaac taggtctata tttctaatga gcatggaaaa cattagcagt tcttcagaaa   87120
atgtgttatt tgctgatact ggttacattc aaagtaaaaa acaaatcttt ttttttttt   87180 tttttttttt gagacagagt cttgctctgt caccaggctg gagtgcaatg gtgcaatctc   87240
ggctcactgc aacctccgct tcccgggttc aagtgattct cctgcctcag cctcccaagt   87300
agctgggact acaggcgcac atcaccatgc ccacctaatt tatgtatttt tagtagaaat   87360
gaggtttcac catgttggcc aggccaggca cagtagctca tgcctttaat cccagcactt   87420
tgggaggcca aggcgggcag atcacgaagt caaaaaacaa atctttacca cctgtacaaa   87480
accctgtcca aagtaagaaa taattaaatc ttcactccaa ccaaaaaatg ttgttaatgt   87540
```

```
gcttacttgt ttttcactta cttagcgatt aacattattg aaaattattg cagcttctta    87600
atgctatatt gggagaaaaa agctcattt gagctgtcac tgattgtcat gtcaaaagaa    87660
taaaaatcat gattattgat ttttaatgta gattacttt caatcaaaac ctctcttcaa    87720
gtcagtaaag tgcaatactg cattctaatc tattactgta tgaaggaac tataatgtgc     87780 cttgttatat cagctagaat attttataga tattagtttc tttacacatt catttaaaaa    87840
ttatgagcaa cctaaacttg aatcaatcag attagaatag ctcaacagaa atctaagcta    87900
cacagtttca atgttaaggg actcatatac ttggatccag tattgataat cctaaatcta    87960
gaaaaacctg agtgaaacaa tagaccaaaa gttatcttca agttcactgc caaatgtaat    88020
tctctaatat ccagaaagca aagcaaaata cacaggcatt gtttgcttcc agtttgctta    88080
tcttgtactc tttttttttt tttttttttgg agatggagtt tcgttcttgt cgcccaggct    88140
ggagtgcaac ggcacagatc tccgctcact caacctctg cccccaggtt caagcaattc     88200
tccagcgtca ggctccccag tagctgggac tacaggcaca cggcaccctg tccggctaat    88260
ttttgtattt ttaatagaga cggggtttca ccatgttggc caggctgctc tcaaactcct    88320
gacctcagct gatctgccct cctcggcctc ccaaagtgct gggattacag gtgtgagcca    88380
ccaaacctgg cctatcttgt acacttaaaa acttactgag gggctgggtg cagtggctca    88440
cgcctgtaat cccagcactt tgggaggctg aggtgggcgg atcacttgag gtcaggagtt    88500
cgagaccagc ctggccaaca tggtgaaacc ctgtctctat aaaaatacaa aaattagcc    88560 ggacgtggtg ccacatgcct gtagtcccag ctgctcggga gcctgacact ggagaatcgc    88620
ttgaacccag gaggcagagg ttgcagtgag ccagatcac actactgcac tccagcctca    88680
gtgaaagaga aagactccat ctcaaaataa taataataat aataataata ataataataa    88740
ataaataaat aaataatctg ttgagggtgg gccaggtgca atggctcatg cctgtactcc    88800
cagcactttg ggaggccaag gcagatggat cacctgaggt caggagttca agaccagcct    88860
gggcaacatg gtgaaacccc gtttctacta aaaatacaca aaattagcca gctgtggtgg    88920
cgggcgcctg taatcccagc tacttgggat tgtttacaaa aataggca ttctgaaata     88980 taattaggta ctcaaaaact ttgagtcaaa gtaatcacaa agtctgtgaa ttgctttaca    89040
catatataaa atattatcca acagttccaa aatcttggca tgttttaaa cattttatt     89100 ctaaagaaat acagagaaat ggaaacaatt cctctaccct ctacttccta tacaaattgt    89160
ccaataattc cccctaaata gatgagaaaa ccacagtatt taggaataaa gaatttcctt    89220
gtggatagca gtcagatcta gaattcagtt ttctaattc caagctaata acttttcata    89280
tctgcactgc ctcaccaagc ataaataggg atatgtagcc tcaatcatta taagcaaaaa    89340
ataaatacaa caggttaaat aaacagtatt tgctgatttt ctgccttaga gtagctaaaa    89400
aacagataac ttccttagct caccctctc tcccctgcaa agcctggtga taaagaataa    89460
acaataaata ttcttcaaca tactcaggag gtcgagtgtc tggtccaaga tctcggtgca    89520
aagaaatcct gtcacttgcg aaagcattaa agcagtgttt agcttcccca cgttcctttt    89580 cctttgctc ttcaacactt aaattggttg tcttgaatgc tttaccagaa gcaccaggtg     89640
catttgaatc ctgaggtgga cggtcaagga caggcttcaa ttctgctgct gtataatatc    89700
cttgcaaaca aggtctctca ccagcatcaa tgttttgcct gacaggtgct cctatttgca    89760
tttttggcat ggcatcctta atattgttta cagcttctag cattaaatcc aacatcttgt    89820
ttttgttttt catgttcctt tccatccttg attcctcttt ggaatattga acacttactt    89880
ctctttgcat taaaaccaaa actattataa agaaaaaaat tactgcacca agcttccaga    89940
```

```
acttttatg gtaatgtctt ttaatgtgta attttactag tcgctttagg tgagccattc    90000
tgacattaaa agcttgtcac ttgacaaata acagttattt cttcttctgt tacttatatt    90060
ttttatcata gatttgctga gaagaaggta tctttaatgg tagtacctat aaacagaaat    90120
gatcgatggt attagtagct attcagtcct acaggcatgg ctcaattcat tcatttaacc    90180
aacaactgaa cataagctac caatgtactc ttatggttaa tgagaataca aagatatctt    90240
gtcctcaaga aaattacact tttggaagaa ataaattgtt acaatttact acaatttatt    90300
ggggttgcaa aaatattgat attcctctcc attaaaaaat acattctttt taaactctaa    90360
tatccactat atactatgta taaaattaat tttataaata tattttgagt taaaaaagaa    90420
tatcttcact tgataaccaa ggaatcaaag gacctcatta ataaattac aaaaaagaga    90480 gctccataag gaagtaaggg tatactgata agtactatta ggcatccatc taaaatagtg    90540
gccttcattt tatgtagttt accctcaaac tgtgatctgc tccagcttaa tgaatgataa    90600
tacagcagtt tcatcagtaa gtaaactatt attctcccag attttccaac ccaatagtac    90660
ttgtgactcc tgaaggaacc cctaaaaaca agaaaatcaa cagcatttaa tttgttgtta    90720
tataacagct agtttttaata gctcacagaa atacaagatc taatagtaaa aagagaattc    90780
attagcttta cttgaagtgt ctgtagggag cctatagaag tcataaagtt aaaaaagcag    90840
aatttggttt gataaaatat tgcttgcaat tgacctaag aacaggacag caagtttatt    90900
aaaccctaat atgggacaac aggagcaaag gaaagaaaa ataggacttt ttaggaaacg    90960
attacatact atgagccgcg atagccagtc aagaaatttg cagggacgaa ggggagggaa    91020
aatgcctgtt cttcctaagg tctaaacata ttttaaagaa aatatcattt atagcaatga    91080
aaattaactt ttgacacctt ctttaacttc tcttccaaag ttctccctaa atttaaaata    91140
agaaaaccag gttctaagat ggattctctg gcttttggca ggaaatttta agctgaataa    91200
acaaaatagg cagaacttag ttctatatac tatttctaat tggagtgctc tatattcttt    91260
tcagtatgga gtggatactt ctgctccaaa agataacccc aattctgaca tatattgctc    91320
ataaaagtga gattccaatc tttctgaggt ttggttgctt taagaacttc aggtaaaaaa    91380
tgaaatgacc tcttaagctt ttgaaaagaa tataagaagt tatagaacca cactatgaca    91440
gttgtgtaat taattatgtg tcaaatgttg tggtaggcta tggttaagaa attaaagata    91500
gcccttacct tcaagaagca gaattgaaat ataggaagcc agaggacagt cacaaagcag    91560
tgtgatatgt gctacgacag gagactaaga aagctacaca ggcttggaac agtggctcat    91620
gcctataatc ccaacacttt aggaagctga ggccagagga tcacttgaga ccaggagttc    91680
gagaccagcc tgggcaacat agcaagaccc catcctacaa aaaatacaa aaattagtca    91740 aatgtggtgg tgcacgcctg tagtcccagc tactcaggtg gctgaggtgg gaggatggct    91800
tgagctcaag aggttaaggc tgcattgggc tatgattgtg ccactgcact ccagcctggg    91860
tagcaggaca agactctgtc tcaaaaaaaa aaaaaaaaa aaaaaaaggg aaaacaatgt    91920
agaaggtcag gagaaatgtt aaggaaagtt tcctagagat gacactgttg agcaaaatct    91980
tgaaatacaa gtcattttta ggcagttaga caggagggaa aatagggaat gtcagatgca    92040
aaaccataaa agcaagaaaa ggcatggtca gtccttgagt acagcataag tggaaggcac    92100
agggagagaa tgcaactga tgtggcttga aggtcagtta aagatcagtt cataaaaacc    92160
cttgtgcatc tttcagtgaa tttggaaatt accaattttt tccaaaatag atggaatgga    92220
gaggactgtt tttaagaaaa gaccacaatc aaatttatgt tttagaaaaa tcacaagttt    92280
ttcagcccca gtaaaggtga tagatattaa tgagatgagg tgggtcaaag gatggagtgg    92340
```

```
aatgatttca agagagtcca ggaagtggaa tcaaacaaca ggacttggtg agagaaaggg   92400
aagaatggga gatgaatggt gatatggttt ggctgtgtcc ccacccaact ctcaccttaa   92460
attgtaataa tccccatgtg tcaagggcag gggcagatgg agataatgaa tcatgggggt   92520
ggtttccccc atactatttt tcatggtcat ggataagtct cacgagacct gatggtttta   92580
taaatgggag ttcccctgca catgttctct tgcctgccat catgtaagac gtgcctttgc   92640
tcttctttca ccttctgcca ttattgtgag gtctccccag ccatgttaaa ttgtgagtcc   92700
attaaacctc tttttcttta taaattatcc agtctctggt aagtctttat tagcagcatg   92760
agaacaaact aatacaaatg agtaaagtga taacattaac aaaggcaaga aacacaggaa   92820
ggatagattc agggtaggaa ttaaggagat aatttgttca gttttggaca tagcaaatgt   92880
aatatgctaa tggaacttcc aaagtgagtt tccaagagca aaaagatata tgggactgga   92940
aattaggaaa aagttctgca gtagagatga aaatttgagt cagtcttggg gtaaatgtaa   93000
aacaaagagg atagagaaat acctacattt aagagtagaa aaaagagac tgactggaaa    93060 gtccaatttt tccaatccta tgaaggaggg gtggtaaaaa aaaaaaaaag acaaatgaaa   93120
acacagataa attatccacg tcaagtggaa gtaattttac aatcttatct cactcttgag   93180
agatgttaaa tgtgcaacag ttggttgacc tttaaaactg aacttcatta gacctggcct   93240
aatgggcttt agtgaaaaat gagaagagaa ccttggcaga gagagtagtt gtagtcatgc   93300
cttcaagatc ctaaggctta ggattcaggg cacttccaga ataatagggc agcaacctca   93360
cctatggggt tccggaagat aagaatggtc aaaatgttgg ggtctcacag gaaagtggtt   93420
cccagttgat gaactacaac ctcatcccct ctaactgtat cttgacaaaa ggtagatatt   93480
catcaacctg tgttcacctc ctttctgttc ctgaggggac taccaaaaat ccccttcccc   93540
agggctatcg agtgacagtc aatttttctg cagctagaag taggctaaat taggaatttg   93600
agaagaattg agctggactc cctattttga cagaacatgg aaaaagagtt cagagaaagc   93660
acagaatagg aagatatgac agaactagat tcttctacag tagtgatagt tttcccaaaa   93720
cattttatgt cagaaatcat acttgtggat agggtgggaa ttgaaaagaa ggatagaatt   93780
aatgacgcag ataagaagata gttctttttta gaataaatca taaactagag gaattgttca   93840
tcagaatgac agtaatccta tcattgtgag tgcatgtgta tctatgtaaa gacccattca   93900
attagtaggt tttagtttgg gatgcttctg ataaaggagt caaggaaagc tcatgagaga   93960
catggatagc atcttattca tggctgtttt tctggcccttt accacaatgt tgataacata   94020
gtaggcaccc agaaaaattt attgactgga aaaggaaga aagaggacca agatttcatc     94080
agaaacaaca acaaaaacaa aacttaactt gtgttaaatg ttgactaggt ctctggtatt   94140
aaataacatt taatacataa gttctcattc tcccagcaat attgtgaagt attcttcttc   94200
ttctctcttt tttttttttt tttttttttg tagagatgag gtctcactat gctgcccagc   94260
caggctgatc ttgaactccc aaactcaagg gatcctcctg tctcagcctc ccaacgtgct   94320
gggattacag ccatgagcta ctgcgcctag cctttgtaat tccaatttta ctgacagaca   94380
gggagagtca aagagattaa gtggcttggc catgccagtt cagtttaaga ccagcatttt   94440
tctaactctg ttcaaactca agttcaatgt aaaatcctga gcttttaact gaaattatct   94500
aaaataaaat gtttaagagt caagaactga tatcctaaat aaaaggcgat aagaaaaaaa   94560
actgaggaaa aaccataaaa actacaaata gcttcctatc attgggtaat attttacaaa   94620
taaatgattt ttaaaaactt ttcaaagcac catttcagta ataagattg aaaataagat    94680 tgtagatctt aaaatggaag attaagaggt tgagaacctt acagaggcag agcctagaag   94740
```

-continued

```
taggaagatg atgttttgat cttttcagac tatttctgaa gggattaatc ttctcttatc    94800
aaccctgatc acttaaagat tccaacattg atgggatttt cattatgact tttctgtact    94860
ttgctgttaa tgtgcaatat taggcttcca ttaatgctga atgacactca acactaagca    94920
tctccatcag ctgtcttcaa ttctggatat acattagtga aaagctctta aaaaaataaa    94980
gtgccttagg cttcacctct gatttaattg atgtgggggc agggcatata ctctgctttt    95040
gttgttactt taagctctcc agataattct aacaagcagc aagggttaag aattacttgt    95100
ctagatcaca atattttggg caaatcaaaa ctagcatctg ataagggttg tatctgtcca    95160
aaggcaacca cattactaat ttctaataag ccaaagatgg gtgtttcaaa atagattctt    95220
gatgtaaatg aatagaagtt atttagacat ggagatacac gataaaatcc aaggcaagaa    95280
tgacccacag ttttccaaaa agactcaggg atttacgctg atataaatga ggcactgagg    95340
ttttactgca aattatgttt ctgtaaaata attttataaa tattttattc caatcataaa    95400
aatgggaaaa ttgatacctg aacaataaaa gacataagcc aaaagataca caataaataa    95460
atgagtaaaa tgaaccaggt attttttaatg ccttttttccg ggaataatgc catgttcctt    95520
gtcagtacta cctgccaaat tggaagccct acgtaaaaac agctcgtgaa acaaaacaaa    95580
tctctcctac agtcaacttc cagttggact cagaagtttg agaattgata agaaaaaaat    95640
cagcacaaca gcaaactcag gatataacat gtcatatttg cacattagaa atgattagca    95700
gataaagggt ttgttcttct tgtactcttt ctaaaacctt taaacacacc tatccaagat    95760
ggctatttgc taattaccaa agatcagatt cacagaggaa gagaagtcaa aaatcatgaa    95820
atagttttta aaaactaaaa aaaagaaaa aaaagaaaag aaaaattcag agatcttcta    95880
aattctaaat tcttatgaat tcctaagagt gaaattcaga gacctggttt taaaaagtta    95940
ttaatctgta acctggtata tatgtagcca ttgcaaaaag tcattaataa aaatattcat    96000
aaagtgaaaa gctaaagcaa tatacacaat tttaactggt tgtgacactc gctatgttaa    96060
aatcaatgga ttattctcag gggtaaaaat atgcttccat ctgaaatctt acaaatttaa    96120
aataatctaa ctaacaagtg gtagcttcca gttatctaga ctacagcttc tcaaacttta    96180
aagtgactat gaatcacctg gggatcttgt ttaaacacaa attgagaagg gaaaatatca    96240
aggtaagatc catcatgatt gtccctctag gtgaagaagc ataggttgca gaaatattag    96300
ttgttcattt aacctaaaaa ttccaactgt agcaattttc tgaagtagtg gaaagcagaa    96360
cattataatt ttacatgaaa gtaacattta atgaaataag aagatagtgg ttcctctcac    96420
ttcttgtttc catgtttgtg acaataaacc attcaactc cagaagttta aagtctggtt    96480
cctgatgaat ttaattgctg tgatgtctaa tttggtatac aaaacttcct tactactgag    96540
ttaaggcatg ctgtaaagag ttaggggtaa ccacactaag cagaaaaaaa acaaaattac    96600
atcccaatat cctaatatag attatagatt aagaaaagta cactattgtg aattattata    96660
aaactcattg gatctttgcc acacattatc tatcatctgt atttcctaat tgaattcaaa    96720
acaaaacaaa gaaaaacaaa atttaaagac cttgccctga taataaaccct ttaagtgctt    96780 gggtagaagt tttattatgt gcccctcatc tactggttaa agtgttaggg aacagaggag    96840 tgcagaaag tcatttctgc ttgcatttat tggtgggtca aatctcatgg tgttttgctg    96900
ctgtagtttg ttagttttga ttatgtttaa gttcatgttt acattcttgg cagcatttct    96960
tctgagcagg aagtggcatg tggatgtatg acaagagaca acactgatg caaagcaaac    97020 tgcatgaaga cagccacatt ctgtctcaga gggggcagca gtagacatac ctcaaagatc    97080
tcagctaaag gcaaagtaga gttactctgg gtggctgggc aatgccacca gtggatgact    97140
```

```
aaactacttg caattgttat aaactaagaa cagctttctg aaccaagata tctgcaggct    97200
gtgagacaaa aagctcagtg acagagttaa ccatcagcaa ccgtgaggca caggtttcaa    97260
tactgagaag gacagggtca gacatccaac ttctcagcta cccctggtca ggtagacatc    97320
tccctcatcg tcatctctga atgtgaaagg ttgctgatag aatcttgatt tgtgagctag    97380
ccaactctat cttgacagtt tgacacaaac aagtaattat gatactacat tatctgtcaa    97440
gggagtcaca aactcagggg ctcacatgct ctttcctgcc acatctacac ctgtgaatga    97500
cttttacatt acatatgaaa gatatgcatt gattacttat ggcatactac agagtagagg    97560
aattctgagg agtgatttag gtggatccag agattattca tgtaactggt attccctgcc    97620
ccccaggtag aggcactgca ttttaaaaca tttgtccatc tatttacctt gtaaacatag    97680
ttgttggctt ttggattagt aaggagatag aaaccacatg ctaatttgaa cagagaaagt    97740
ttaatacaat ctggtattaa aagaggattg gagtaacagg aaattgccta gtgggagtta    97800
aggagaattc taaagaatac aggagttgta aatacagtat aagggcaac cactccccct    97860 atggctgaaa taagtgttca aggaagggct ctcctctcac cagggctgag atccagagat    97920
gtctatggga atgccctagc tttgactacc tggtaaaaag tcatagaagt acttcattca    97980
tgggacttac cagaaatctg cccctgaagt tccagaagag gccattcaca gccggggac    98040 agaaccctag aactagctag gtgctgagga aaactgctgg ctgctgaggg aatctggaat    98100
cacagaggtt gtcccctgca ggagtttagt gaactttcat gtgccacaca ggtaacaacg    98160
gctctgggct ggctgcctgg gacaaaggtt gggcagctgg ctccctagac acccagtctt    98220
gtggggcccc gagtttggca tgtgtggatc tgaggagaga gtttggggag cagtgactta    98280
ggtgacagag caggtccatg gtgtctgtgt ctcaagggta caccactgct gcctaaatca    98340
agctctaaag aaagtgcagt gtgtggggaa caccaactct agaaaaagct gtgttctgca    98400
gatacctagt actggagaaa atcatactgg ggagtgagca gtggaggaaa actatgctca    98460
aaaggagctt agccagtgag catcacagaa accagaaaga gaagcctcag ccacttcagt    98520
gtccctccag tgccctctac tgacaaggct taacattgta cgagccagca aaaagaaat    98580 ttacaaggcc cagctccatt attacagagc aggctaatac agtaaatttg gaactaagag    98640
acagtaaact gataagcagc aaagtctaca cttttcacta ctcagcttcc acatgcaccc    98700
tctcccacac actgaaactc ctgtacaata acaacacaat tctatatttc acctaacaaa    98760
gtctaactgt ccttctttat aagtgaagaa gttctatctc ctcaaaaacg agagacatag    98820
agtcctaaca gctattgtag tcattgctgt gactctgagt tactccttaa attctgtcac    98880
agtcccacta aatattctgt tacctaaatt ggaaagttga tctccaacgg cttctattta    98940 acattttta aatgaaaatg agagaagaaa attgttaaca tatacaaaaa aaacctagat    99000
ataagaggca aagaaaaat gtgcattgaa cctgagaaag ctgattgaaa aaaatttt    99060 aaagaaaaaa tacgcaaacc tacaataatc ctcacttaca taattggctg cgaggccata    99120
atgaatatct atggcttctt tcttacacta actactactc tgtattcacc atgcccttaa    99180
gcattctagg agtccacaga tgttggtgat gtcaaggaag ggcaaatcca tatgtagaat    99240
acttgtctat tctagtgagg agaagtctct gccccctcaa tgaaggaaga aatccagtat    99300
aatgaacctg ccacccagag gctggctgat ccccgcaggg gctcaatgct ggattctgca    99360
gattaggaac tcagcagcag cgctatccca gtcaacttta caaggggaa gccatgttgc    99420 tgagcccatg catacacagc tccagtcttg ccaccaagac tcctgtttat gggcccactg    99480
agacagctgg agagataggc tgactgacat gcagaatgtg tcatttgtc cacttgatta    99540
```

```
ttaagagcct cctctgcaat ggatgtgctt ttgtgggcac tcagagggga tacaaattct   99600
ttcagggtct tttcattttg aaaggttcat tcacatacct cttcctcaaa ctaactacct   99660
tgtcaccaat cttccaatcc tgttccttcc aactctgacc ataaaaacca ttaacaacta   99720
cccatcgatg accaatatag atctgtattt ctaggcatgt ctcattccca acatggtgga   99780
caaccatatt tactgttcaa atctctgcct acagaaaagt tttccttatc cagtattatt   99840
cacagttact cacgagtagg gctatagtgc tacacagtca ttaatcttgg gtagtactag   99900
tgttttgttc agattcatct gcaaatcagg tttgagggt tttttgttg ttgttgttgt   99960 tgttgttgtt gttgttttt cttctaacaa atggactaag ggaatcgcca agaagccaca  100020
ggcatgagtt gaaagagaca aggcaatgcc attagagttg ctaccaaaga agtctgagtc  100080
cctggttcat gcaacttatt tgtcctatcc agatctgctc tagttctgtc tcatgtacta  100140
tttccactca atgatatatt gctgttgtac atcgctaacc ttatggaaag ataggtcaga  100200
ttttacccag ataatgatgg gaaacttggt ccacatgata acctgacact ccataattat  100260
gcattcaata tctacctagt agcaagtcag aaggtgttta tcaaaaagta aacagttatc  100320
tgaagaaaat atttatttca aaaccctaga tgtctgtatt gtgattctgc tattggcact  100380
ttccagaggc tccatagagc attcctcttt ggcacagata ccaagagagt cgttgagttt  100440
gctagatcat aaagctgaag tggtagcata gcctgtactg ctgggcttgc tgcagagcct  100500
tcttctactt tgatcatcat taaaaactgg cagccttatg agttactctg taaacaggtt  100560
gaggtagcat attcaaatgt tgtaaatgtt gcccccaaat tcaaaaatga ctattgaggc  100620
tgggtgcagt ggctcatgcc tgtaattaca gcactactga ggtaggcgaa ttgcttgagc  100680
ccaggagtgc aagaccagcc tgggtaatat ggcaaaaccc catctccaca aaaaaaatac  100740
ataaattagc cgggtgtggt ggagctcacc tatggtccca gttactcaag aggctgaggt  100800
aagaacattg cttgagccca ggaggcagag gttgcagtga cccccagatc ccaccactgc  100860
gttccatcct gggcaacaga atgatactcc ctctcaaaaa agaaaaaaaa aaaaagccta  100920
tcgagcatag tggctactga atgcccagaa gttttgctga atttttgtgg ggctgattta  100980
tcaccttcta attcttatat gctctacaag gatatctaaa gtatttgcta ctttcttctc  101040
atcagagaca atcagcatat tatcatcaat gtagtggatc agtgtgatga cttgtgaaat  101100
gttacgatga ttaagattaa gaattgatct agccctgagg caagactgtg aagccatatt  101160
gttggctctg ctagataaaa acaaattgtt tttggtggtc cttgtaaatt ggcagaaaaa  101220
gatattaact aagtcaatag ctacatacca atgccaggg gccatgtggt ttgataaaga  101280
tattacatct gggtcagcaa ctacatttgg agtcacccaa taattaagtt taggggagtc  101340
tacagccatt ctctaagatc catttaactt ctgccgaggc aaaataagtg agctaagtgg  101400
ggatgtgata gatatcacaa gtcttatttc aaatctttga tagtgacatc aatcttgaga  101460
gtttcctcag ggatatgtta ttacttctga tttactatct ttgaagaaag gggaaattct  101520
aaagccttct actcagctct cctatcacat ggtcctctct ctatgggtta gcagggggtgt  101580 ccaatctttg ggtttccctg ggccacatta gaagaagaag gattgtcttg gccacacat  101640 aaaacacact aacacgatag ctgatgagct gggggaaaaa aagaattac aaaaaaaaaa  101700 aaaatctcat aatgttttaa gacagtttac aaatttgcgt tgggccacat tcaaagccat  101760
ccagggtcgc atgtggccca tgggccacag gttaaacaag cttggtttag agagtcaata  101820
tagagattct gccagttacc cagtatgtct attccaatta ttcattaaag aactggggaa  101880
ataagcacag gctagatctg ctgaccccct ggacccacta tgagtacaac tggagctaag  101940
```

```
actccatttg ttacctgagc acttttaagt ctccactttg aacagttggc cacagtatttt  102000
ttgggtcccc ctaggaatta gtatgaaagg tctgattatt tccttttccc caaagcatag  102060
tctctggtaa atggctacag gtcccttttgg ggaaaagctc tgggagtgtg aattgactta  102120
ggtctgaaaa ctgagtgaga tgctgtgact cttgattgca gcaactaaag ttaactttt   102180
tgctaccaga gctagagatt ttcctattat atagatgaag ggatgctata gtactgctta  102240
cgtatttcat tcattagcta ccactaggca tataccaaag acattatctc agctgtcaga  102300
aacatctgca agccaatgtt ttctgatacc tctatggccc agcttttcat tgtgggagat  102360
gtatatactt tgtatttggt gtataagggc ttactgccac ttggcttttg ctactatgga  102420
atttcatcat ctccagtaaa atcagagagc caatttcaat ggtctacaaa ggagagcagg  102480
cacagatttt ttcatggatg cagggaatcc cttcactaat gtacttctta atactttagt  102540
gaaaggagtg tctactgggc cttttcatgg catgtatttg gaggatgggc aggttgcatt  102600
caattaattc aaccaaccat tcctttttg aaggagtcca aacacacaca agcagtaggc  102660
aatttctctc cattcattct tcctttgagg ccccaaaaat attaaggaat aggggtgaa   102720
ggaataaaga agattgcttg ctcaattgtt atcattttgc attcaccttt ctacaggttt  102780
accaatgctg atgtgataga cactcctcct ccatctctca gcttccatta ccctctagaa  102840
aaagtgtcaa caaactttttt ataaggact agataacaaa ttttttttttg ctttgctggc  102900
catatggtct ctactgcaac tattcaattc tgttgtagta caaaaagac aatttgtaaa   102960
tgaataatca tagctgcatt ccaattaaac tttgttttca aaacaggta gtggatcaaa   103020
tttggtctaa gaactatagt ttactaaccc ctgctctaga aattctaaaa gacttcaatc  103080
tcaatatttg taagtctccc catatttacc ccttccccat tagctgccac ctccccagat  103140
ataaaacaga atttttttca agtcttccat aacatcattt tttattatac ataaaatctg  103200
tgtctacctt taagattagg ctatatatgt gcctaatttg aagcgaacaa tatccctcca  103260
cttctccaac taccatctga aattcctgca ttatccactc ttcatggtta aggcacaaga  103320
aaagctcctt taatgtaaaa tttgggttgg aaataaaccg gtctcagcct aaactttaat  103380
tcttctatca acagctggcc tcaagtaggg taattttacc cagaaccatg catagtcaat  103440
taccatacac agtgaggcct actaaacaca cactggatgc caagctccaa ataggggagg  103500
gtggggtgct taattcagtg ggatttatat ttaattcttt aggcaaaggg agaggccctg  103560
atgagttttc agcaaggtga tgacctaatg agaacggaag tttagaatga ttgtcgttga  103620
agttgtgctg aatatggaat ttttggggag gtagaaaaac ctgataggag gctaaaggca  103680
attaggatac ccttaaaagt agtccaggca agagataaat ataaggggca tggaagctta  103740
gaaacagatt ttggaagtag agttagctga actcagcaaa tgagtcaatg tggaggctac  103800
agaggttgtt aagttgtgac gggtgttaag gatgtgttct ggacttgttg aaaggtgcta  103860
gctagctagg tgcttgtaat cccagctact cgggaggctg aggcaagagg attgcttgag  103920
cccaggagtt caagaccagc ctaggaaaca catcaagacc ccatcctgaa aaagaaaggt  103980
gctagcagat ggaatgctct ctcttctgca ttatcttcag tggtagacct agaactcaaa  104040
aatatgagac aagaggccag tgaaactaac agaggcaatg atagagggta gagtacaaga  104100
aggagactga ggtaacaaca gaaacaagtt ttatccagtt caaatgatgg ggtcacatct  104160
gaaaaaacaa aggtcatgtt caaaaagctc aaagaaaaca ataatttcta tgagaaaccc  104220
tgtctgcttt attaattgtc ctctagaaat gagcccctc tgccattaag tatttactat    104280
caggtgtttt tccccctttc tccttatctc atttgactca gaattatcaa acttgcaggg  104340
```

```
ctgcttacta ctgtagtctc tataaaagca tcaatcagat gtggggatga cttctagaaa    104400
tcccatagat acgctaatgc actagtgaaa tggcacacct gtaacttgca cattaaagca    104460
ttgttctaat atcaaagggt tgaaacaacc gagaactcta ccaatgggaa aagagataaa    104520
ttatgatgga gtaatatgat taaatattat gcaaagtaaa aaacaaggcc aatttatatg    104580
ctgatatgaa atgatcccaa tatagttaaa tgggaacaaa aaaagcaaga attatttgta    104640
ttttaaaaag agggaaaaaa catacatatt gttttatat ttttaaaaaa tagcatcggt    104700
tacctctggg gaagaaaact ggtgtcagag ggcaacagtg aaaggaagat ttatcatata    104760
cctctcctaa cttttgaaaa ttgtgaactt caaacaactg gagttcacaa acaactgcaa    104820
ctactaacac attttttaaga attaaataaa acagaaagga aaatgtatga aggtagaata    104880
aagagtttta gacattcaat atctcacatt tcttcattcc atgcaccatt ttccagcaag    104940
ctagtggtgg atatgtgttt catccaaatg agggggtgaa taaaaaacaa aagtcatagt    105000
atctaaggaa cagaggctct atcagagatg tcagcaaaaa gaaattccga acaaccacca    105060
cggaacaggc ctagagagca acagtccgaa caggggcaag aggacagatt gctccagtaa    105120
gggacaaata aatctgttat gttagactac atggaaaacc aagctgaaaa gatgttagag    105180
tacatagaaa ttgtactcca atagatatat ggaaacacta agccaagtgt tttcttaaat    105240
gagttcatta ttacttctag gattaaaaaa aaattctaca agtaaggaat cctactcgta    105300
atatgcttgc ttgactctgt agtaaacaat atctatgtaa tcacagtaaa taaatactaa    105360
aatgcaaaca aacaatgtga gaattatgtt ggggaggtcaa ggagggagag tagaggtggc    105420
tgtgtatgaa agagctaaat atttatctac cataatagga agtcagtaga tattgccaaa    105480
tattgataca ttaagaaaca gcagtataag catattattt gaaaaggtaa gggctagaag    105540
aaacatttaa ataaatgaaa gtagttgctt ttaggcaaca ggactgggga gacgagaaag    105600
gaggggcaga gttgactgga tttttattgt tgttggaagt cttttaataa ccctattta    105660 ctttatttac atgtaagtag gataaatgta cagtcatgtc ctggtatctg caggagattg    105720
gttccacaac ccctgtggac accagcatct gcagatgttc atgtcgcttt tataaaatga    105780
tgcagtactt ggatttaacc tatgcacatc atcccaatta cttaaatca tctctagatt    105840 actttaatg cctaattcaa tgtaaatatt gtgtaaatag ttgttatact gtgcttttt    105900 atattatttt ttattgttgt gttacttttt tcctgaatat tttcaatcta aggttgtttg    105960
aatctatgga cacagaactc atggaaacag aaggcgaact gtgcaggatt tggaattgta    106020
ctgcttcgac ttgagtcttg gctctaatct ttcactaacc ttgtaaatag aggcaaaata    106080
cttaatctct caattttcct atctttaaaa tagggaggaa aatagtatgc acctcatagg    106140
gttgctttga agactaaata agtaaactca tgtaaattgc ttaaaatatg cctgccatgt    106200
aagtgttcaa tagtaaataa ggaccagtac ttattatgag aataaatata aactattatt    106260
acttgataaa aatataaagg cattaataac taaaatctat ttttaaaaat atgggccata    106320
tattaatgtc tgcctccttc gtggggaaac ttttgttttt ataagttaat gctcccaggt    106380
actaaatagg actttattttc tttagcctac agccttcact ctaacccata gttagggga    106440 aggatgtggt gagactgttg aaaaattcca agttacagtt agtgatgaaa agtgggagc    106500 tcaaactgga atttgaagac tgcatgttaa gtagttatgc caaatgggaa gggaagagcc    106560
ttccaggcca ggaagcccac ttgcaaagac ctagaggcag aaggaacaga gcaatataaa    106620
aagattggtg gagctggagc aatgatgagt gtgctatatg tttgatggga gccaaatcat    106680
gccaggcctt tgggcatgtt aaggagtttg ccttatctta agggccatga agggctttat    106740
```

```
gcagggtata acataaccac atattttgaa aagatcactc tgggtgcagg gtgaggaact  106800
aacaagcaag aagccagaat gagctcagat agacaaacag cgaggccatg gcaaaagtcc  106860
aggcaagaga tgatgataga gataggaatg aataaaagta gatggatttg aggaatattt  106920
agaaggtaaa acttacagaa cttggcatag gactagccaa aaagagatga aaggactgct  106980
aattccaaga aatcttttgc ctcattttat ttttgttttt ctttgtttgg tctagtctaa  107040
ctcaattata ttttttaagt aaaggctgct cccttcaagc tcctcaacaa taataatata  107100
ctcaattgtg gaatatgtat aagcaaaagc tgcaagacat ttcaattaca aagttaactt  107160
ttcactttta aatgataaaa ccccaagatc ttggaacaga accaaaaggt cccaaaataa  107220
aatagaattc aaagtaaaaa gatagaagta acagcaatcc aaattaaata gactaattaa  107280
gtcagtgaaa caagttcgct actccccagt ttctttggtt acttcccatt aaaaaggcag  107340
attgggccag gcgcggtggc tcacacctat aatcccagca ctttgggagg ccgaggcggg  107400
agattcacaa ggtcaggaga tcaagaccaa cctggctaac acggtgaaac cccgtctcta  107460
ttaaaaatac aaaaaaatta gccaggcacc tgtagtcccg gctacttggg aggctgaggc  107520
aggagaatgg catgaaccta ggaggcagag cttgcagtga gccaagatca cgccactgca  107580
ctccagcctg ggcgatagag caagacatca cctcaaaaaa aaaaaaaaaa aaaaaaggca  107640
gattgactta tattgcctgc cgatgcctct ccccttctg tgacatttct accccaaaat  107700
ttttattcca caaaaggctt aatggaaaga gaaattttgc atgttttgca ataatccaa  107760 aagggtgtgt gtgtgtgtgt gtgtgtgtgt gtgtgtgtgt gtgtatacag acaagagcaa  107820
aagcagacta tatttatatc gtatcaagca aataatagaa gtatacacag gacacctcac  107880
cctgctcagg tatatgtgga ggtgtgggtg aggggacaca gtttcccaaa tgaagcaaga  107940
ccttctttga gttttaagag ccattaagag ctatagatag atgtaaagat agaaggaaag  108000
gcactctctg cagtgggaag tgcaaaagaa aagcacacaa gaaaaaaaaa acaataagaa  108060
gtctattgct gggaaataaa atttcggctt atggagtatc actccagagt taagcaagtc  108120
tcagatccca tgggaccatt ttaagggctg tgggttctat ccggtaagca acagaaaatt  108180
gttgaaggat tttaagtgag agagagaatt tgcatttcta aaaagatcat cctcatcctc  108240
cagatggtgg acttgaggtt gacaacacta tctgctgaga taccaggtag gaggcagcta  108300
tgataccttg gttgagagat gttaagacct taaactagat cagtagaagt gaaagaattt  108360
atggctggga gaaaggtata aaatgttaag tggattcagt gttctaatgg ttgttgtctt  108420
agttcatgct ataacaaaat accttagact gggtaattta aacaacacaa atataccact  108480
cacagccaga aagctgggaa gtccaatatc aagctgctgg cagattcaat gtctggcgag  108540
ggcacatccc tcatagatgg cctcctaggt atcctcacat ggaggaaggg caaaaggcta  108600
acaagctttc tcagtcctct tttataagga cattatcttt tacaaaaaca cacgaggcca  108660
aggccctcgt gacctgatga cctcccaaag accctactcc taataccaat acattggatt  108720
tgatttcaac atatgaattt tggaaaaaca caaacattca gaccatagca gttgtagagg  108780
ctaagaaaaa gagtttaaaa ttacctctgg atttctggta tggcacctgg atggtagtac  108840
acatttatga ttcactctcc caaatctctg cagcaaaata tatttcaaaa ttcaggatt  108900 gacagcctgt agtctcagct acttggaagg ctgacatgga aggatcactt gagtccagga  108960
gttcaagatc agcctgggca acatagtgag accttgtctc ataaaaaaaa aaaaaaatct  109020
gatttttttg gatgttagaa aggtgatatg gtttacataa tcaatgtaaa agtgtacccc  109080
agcagggcct gggcagtatt atgtaatcaa acagcactat ttctgcagct ggacataatc  109140
```

```
cactaagttg aatacacaat cacaatagcc tcctgacagt tcactcaggc tttgctccaa 109200
ctgagttcaa gttttgctaa caaatgagtt aaattttgtt ttgctttgtt ttcagaggat 109260 gattttttgaa ttatagataa gaaatggtac aatgtactac tatctataaa tagaatacag 109320
agagtgagca ggttgtttgt tcatttgttt tttgatgaga tgaaggttct ggtttgaaca 109380
tatataatct ccagtgatga acaaatgtta aagatgtcca ataggcaatc atatagaaaa 109440
gaaaattagt ttggacagtt tgaaactgaa acaattatag ggaaaaggtg tacttggggg 109500
aatattctct ctttagtgcc aaaaataaga gcccaactct gagaatgacc caaggaagtg 109560
tcatataatt gtcagtagtc tctaatgacc tagaattcag agtcctactt gtctttgctt 109620
tgcaataagt gaatgtactt ttgtctcttg ccactgctgg aattgatttg aattcagttt 109680
tcccccttag tgtacatgag ttgtgttaaa tttcacccaa attacatagt atgaattatt 109740
ttgatactaa ctaaatgcat aattgaacag ctaactgaaa acaccttcct tttcaatagg 109800
attttatatc tataaagtat ctatcattcc aaatgtattt ttgcacttga tggactaaag 109860
aactgaatac atgtgaagat gattcaggca ctgatcattt ctaaaatcct aaatatgata 109920
atattttcct taggagaaat atttcaccca ccaagaatgt aaaggcaggt taaaattgaa 109980
agtgtctacg gaaggcttaa ttatccaatc agagcttcca agactacatt cctacaaatc 110040
attgagggat ctattttaat ctctcaatgt agtcttttg tggagagggg gagtgtaatt 110100
cctacaattt gtctcatact tgtttcatag taaaaaagaa aagcattaaa tattaacaga 110160
atataaacca aataataaac tggctatgtt ttctctaata aattttcaga ctccacccag 110220
aactctaact cagtcataaa actttaagag ttcagaatag agctggacag aaggtttctc 110280
cctcaaaatt tcactgaatt cttatcatca aaatcccctc agaaaaaaat atttctagtt 110340
tttcctgttc ccaaatacac tacagcatga tgagaaccca tttaacacaa aatatgtata 110400
atgaacaagg tttcatgtag ttcttaatat ttgaaagatt taatctagca ccaaggtcct 110460
ggagcctcaa gccctacaat acatgtttaa ttaggattac agtaaagttt ttaagaaata 110520
atttattttc tttcatgtga gtgggtgtgt gcctgtgtgt gtgtgtgtgt gtgtgtgtat 110580
acgcatgtat gagacagaga aaagaaagc tggtagaaaa atcagccttt aaaagaacaa 110640
aaattcaaca gaatagtgct attttcacat tgagggctcc agcactttcg tggtcataaa 110700
gcagtctaat tgtttagacc aacgttttta aaaataaaat aataaagaac atacatgttg 110760
taaggttaag cactgttta tattaataaa acttgtttca tttatataca ctcacattgg 110820
agtttacaga gttgaggcag agaataaatt agttattgag gattgcagta aaaggaaaaa 110880
aaagtttaaa gaaacttagt gttaaggaag tgtgcttgaa ataaaaaatc tggagtgttg 110940
caaatggatg aaaggcactg ggtagctgcc tcataaaata tattttaagc caatataata 111000
aaaagatcag aagactaaat aatgttatcc acattgactt aaaaaattaa ctgtggcttg 111060
gaaataccaa gaaggaacta aaagtctcaa ctgacatggc atcatcaata tgcatgctat 111120
tccacaatga gaggagcatg atgccttcac tgggtagttt ccacgaagtc aggcaatatt 111180
tggacaagta gaaatgaggg taaatcagag tgaagaaaga gcaatggaca attctgtaat 111240
tacaaaggcc ttacaaatta tatgaaagaa aaaagataaa catcttatgg taagtgagga 111300
tgtgggtggt gaaaagtaag atacaggagt catgagtcaa gccactggaa tgatcatgcc 111360
atctctgagt gaaatgaagt tagaatacct ctcttggctt caattttca taaatggatg 111420 gtttgagtat tgaatctcca aagtgagaaa gggatctcga gaatgctagg gctggaagat 111480
actcctgatt gttttttaagg ttttgttatc ttaatctagg aaagtattat ttttcctatt 111540
```

```
taacagatag attaagttac actgttactc tagctaatga aaacatgtta catttctcac   111600
tagaggttaa gaggaaagac agtctggtaa catctgccta gtaagtaatg aagactaata   111660
ttcaaaattc agggaacaac tcctatatct catatttaaa cagtatttag cacatttgtt   111720
tctctgtatg gagacaagat taagaggtca ggtgagatcc ttttaagaaa tgtagaaaag   111780
tggtgattga attaataatt acatcatgtt atgctgtggt tggcttttag atttccatct   111840
aatcttaaaa agaagaagaa aaataacccc actacatgtt gcatcaggca ttttaagtaa   111900
aacgtgcaat ttaaaaaata tttttaaaat gtgtggagat agaacaaaac aatggaattg   111960
ttattattat cagaaacttc tacgtaaaaa tgttggttaa agcaatatat aaagattgat   112020
tctcggtaca aattgcttgg aaagtttaac atgtgcacta gatttcagat attaaaagtt   112080
aaattaaaaa aaagaatcta atggcagcgt gtgactttaa cctcatggat tttagccaca   112140
aacgcaaaga aaatatata caataaaaga agcaacagat tttcccacaa gcagagattt   112200
tctaattaaa atgctgtcac tttaatattt tttagctata gaatttgact gtaaatgtct   112260
tcattatgta gtgtaacttc tatagcaagt tatgttaacg ttttcaagaa tcggaaatat   112320
tggtaactcg atggggttct taaaacagaa atagtttctt tgatgagttg gaaagagaag   112380
gaaataaaag tctaaggtaa gcgccagttt caccctcaat tcttaggctt cagaaaagcc   112440
taattaggca gggaaaggaa tctgggcctg gcacacccaa gcttagacgt ggcaggatcc   112500
tgaaacaatg ttttttttgaa cctttgagtc atatgccaca ggcaaaccat agccgcgata   112560
tgcaggtcct taagtcaaca ggtcctctaa cgagatggtg agtggttggt gcgtggcagt   112620
tggatttctt cccgccacgg aagaaaagaa ctcttctcca ttgatcagga aagtgggccc   112680
aactctggcc tggagagcgc acccggaaaa gtgcagagtc gaaacagaga gagggggtg   112740 tccgcgtccc ggccacagag ccctttccaa accactcgga aaccatttaa atggctcggc   112800
ggccgcggtt tgcagcctag aactgtttgg ggtccccggc taggaaagtt gcctggcaaa   112860
gccatgtctt tcgctgtcgc gggatgtcct ctcgggcaga gaggctggag gagacaggca   112920
acctgctagc cggagtggaa gcgcgcccgc ctcccgccgg gccctccctc tcagggtccc   112980
cacgctgcga ccctcccaag ggcaagtccg gggccaccag gtctttggtc tccgtccagc   113040
tcctcagggg ccgccccata gggactggcg gggcaccgt gggcgagagg gtgtgaccgg   113100 gctcccccc gaggcgccac ctgccccttg gcccagggcg ccccttttcgg gatctctcca   113160 ggggcaaccg acacactgct ctcgagaccg tctccaaccg gccacctgga ccgtagccct   113220
gtccccaaca cgtgaacccc tgcggccgtc ctcccgcctg ctctaacgca gcccagggt   113280 accgcgtctc cctccgcctg ccgccggctt acctggcggg tgggcagggc agggtggcgg   113340
gaagcggcgg ccgggcaggc gctggacgtg ggctaggcgc caggtgcagg tggcggcggc   113400
tgcgactccg gttgctgtcg ccacagttgc ggctcagtag agctcctcct ccgccgccgc   113460
ctcctgcctt cccgctgggc ctcccgcgtt gcctggagag gcagaaccga ggctcggctt   113520
ccacttggag tctcccaggt gagctccagc ctgcgacgtc ggcaggggcg aggccccact   113580
tccgcgcctg cgcgccagcc tcccgccccg cccagccct acctgagcgc tccaggtgag   113640
aaccttggat cgcgcgcgca gggtgggggc gccgtccggg ccaagcctgg ctgtcgcgcg   113700
gcttctctct gagtggtcgg cgaggctgct gctccgcgca agttgtggct cccggcccat   113760
ctacattgga ggaatcctgc actgacctgg tggcagtgat caccttgtag ccagaacaca   113820
gtctgctggg tccttgggga accagaagtt ctagatttcc cccacacggt tcctcccttc   113880
ctcctcggtt cgccaaaatg aagggggtgcg ctgcctccga ggaccacttc gggagggcag   113940
```

```
caactgctgg ctcatgtggt ttcttcgggc agggttcagc agcttctgtc accagttagg  114000
tttcgtgagc ttccttcccg tgtagtcttg atttcatcac ttgactcact tcagcgcagc  114060
tagtggtttc cgtttctgta cgcgggcgct ctggtagggg cgcctcacgt ccaaaggagg  114120
agtcttcttc caaagaagag cctttggtat ttggcagagc ctcgccaatt tggggcgcac  114180
ctccccttcc tgggatgctc tcagaaggca aaccaattcc cagaagagag ggaaaaacag  114240
ccacaacaga gagaaccttt gctgtccctg tttggaaaga gattgggatt tcctggagag  114300
ggcttgcttc tactgcaggt ttgtttaaaa gctcaacatc tattctggaa gagaacaacg  114360
cagactccag gaagatggtg ggttttgctg tttttaagac aaaaaaaaat tgttaaacag  114420
tatttgttcc atttatgaca caactttctg tttcagcctt ccttctgctg ctgcaacaaa  114480
cattgacaca cccaaaacca ggacttaaaa tggcctttat acctttctat gaactcattt  114540
ctttggccct atcccaaaga tatctaggga tataaataga aaactagcta aaaactttt   114600 ggtgtcgtgt ttaatcacat ggtggtaggt tttactatga agtttagttg tggccttcct  114660
cctacatttt gacatgctct tatggtgctt attcactgtt ttattagtgc tatgcgtgac  114720
ctaaaaataa ggtttaaaat acagtttagt atagtatcaa caagtgtatc tttagtattt  114780
gactactcta agacattggt tttagcatcc atagtgctat tttatactag gacatctatg  114840
agttagggtt taagacttta gtaaactagg tagttctttg cttgttttac atgtcatggt  114900
tattttgcga gcaccaagga acctccatgt atttgcaaca ttttaatatc agtacctaca  114960
agcaattgcc aagctccctt tccctccaaa aacaaacaaa caaaaaaata gttcaggaga  115020
tacttgtgtg tattgatata ctaacttggc agtgtttttc cttaggtcca ggtccagaac  115080
tgaaaatact aactactgaa attctcttct ccttctcctt cttcttcgtt gtgccacttt  115140
gtcgtttacc cctaaccaga ggttaatgtt agtctttgga aaatttgtaa ggtatcctaa  115200
atgtataacc aagaaacctg taccctttg cacgcaccac ccatctctga atgaagagcc  115260
aaagattgtc agagttttga tgtcccacca ggcgaagagc aacactttc actgacaatc  115320 aggacagagc agatggatat agaataacaa tctggaatcc aaggactgag atgcattgac  115380
agcaagacta gtaacgtcaa ataacaactg aaaagagaag ctagggtaga cctattaaaa  115440
gagagagcca gcaaacagga ccaaaatgct ggatgaggag tctaaaaaga acagaagaaa  115500
caaaaaagat caggagttac taaaatttga ctgtcagttt tacaatggag acagacaatt  115560
taaagaagga agcagttttt ctgagtgtgg cattacttgt gcacgttgag tgtcatatat  115620
atagagagag agaaagagag agagtgagag agagtgagag agagagagag agagatatct  115680
tggggatgag acctgtctaa acacaaaatt catttatgtt tcatatacac cttatacaca  115740
tagccttaag gtaattttat aaaacattgt aaataatttt atgcatgaaa caaagtttgt  115800
gtaaagtact tatgtgtgga attttcaact tgtggtgtca tgttggtgct caaaaagttt  115860
tgaattttgg aacattcag attttggatc tgtggattag gatgctcca cctgtactat  115920 tttacacaac gttgcttgta ctatttcaaa gcattctgaa agcaaagtct taatattaat  115980
aaaaaatttt ctatgtgaca ataaaattaa aatgctgcag gcccaagaaa aaatatat   116040 catattgaaa tatttaatgc cccaaatcta atcagatgca ggtttttgaa agtaccatcc  116100
tattcaaaat tatgaaataa agaatttgtt tcataaagag aaattagcat ttcatcataa  116160
ataaaatcca ggaaccttag tgtagacatg cttcagaaat aagctaattt taatagtata  116220
tgtttgacat ataatgacag ttaagataga aaactgggca gattttacac aggaaggaaa  116280
caaacattct ctctctctct ctctcacaca cacacacgta cttattacac acacacacac  116340
```

-continued

```
acacacacac acacacacac gactagccac aaaatgctca tttgcatgga tttgaaacaa    116400
tactcactcc ttaatacttt ctgttaacat ttaaattaat gccaagacca gcacctggca    116460
cttagtaggt acttaataaa tatgtgttaa atgaataaat tgacccatca agtaccataa    116520
aaaaaatgcc tagtgtcttg agcaatttac aggtctaaag aatggtttta cccaacagta    116580
atgacaaata atccaaggca gataagaaca ctagactggt aatctgaatt gcaaagttct    116640
aagaacaata gctaccagct ttcacatacc tacatttcaa aagacactac gcaaacaac     116700 ttacactcct acaaattact ttacatctgg cttaaatatt ctcttccaca aaacaaaata    116760
gtggtacaag atgatctaca ggcttcttta cattctgatt catataaact ctatgccaag    116820
agaattgggc aaataaataa ataaataaat gaaaccttct ggatatagca ataataatta    116880
atgggacagc aaagatgaag aaactgaaat tatttagctg agatcgaaat tttaattcat    116940
aaaaaatagt tgtaatatat aatgtaacaa gtaaatgtgt aaagttacta agcctaactt    117000
taaactattt tagtttgtta attgtttaat tgttggttac acaactttgc tttgaaacat    117060
actctagaaa cagttttgcc tcatgaggga actagagctt ttagtgagga tctcaaagtc    117120
agactgagag atttggctca aagactgaac agactggaat aatttcttct caaagcagta    117180
aaagtgttga aatgctattg attcaagcag agaatagagg tggtatcaca gtgaagagcc    117240
acaaacacgt gggtattttt taaataatga tccaacataa ttctacattg tgtttaaaat    117300
atagcaagtt aaaacaggga aaatataaat aggttatttt agtatgaact tttttggaca    117360 ttgtttata tgattcttcc ccctgtagaa tctcagaaca atcatctcag attttcaaag    117420
tggttcacat actatgaggg gttgacttag attacaacaa aactatgtct tgctaatctt    117480
gtattcttag tacttggcac atagtaggca ctcaataaat atttgatgaa atgtattgaa    117540
tagagtgcat tgtttcaagc ttttaagcat tagcataaga gcaaaagaa atgtcatgct    117600 gagtcagaat aatattcaat ctaactggct ctaaattctg acagtggcac caaagaatat    117660
tttgtggaaa actatggtga tagtcttgca tgatgttgac ctcagtgatg tactcgagta    117720
tccctcactc actctttttcc taaattgatt tctcttttc tgtaacatgt ttctttaaat    117780 tgaaagaaa ttaatattca ttacagagaa atcagaaaat acacataact gcaaagaaac    117840
tagctttgaa atactcagaa ttccttatac caagatgaat cagtgctatc agaccctttc    117900
tatcatgtat ctttgcagat ttttttttatt gaaaagttg gcaggaggca cggcatggaa     117960
tggggaacat agagggatac agagacaggt ttgtaaaata aaaactagat cattctgggg    118020
acttgttttg tagccagagt tttctacttg acatataatt aaatgtcaat aaatttattt    118080
tacagtatta ttttaatggc tgcctgatat ccctttgtaa ggatttaatc tgtcaattac    118140
tgttggacaa tgaagattgc tcccaaattt tgctattgca accagtgcta taatgatcat    118200
actcttcatc tgttgaaaca tttattacga ttttcttcta attgactttt attttgtttt    118260
tgttttatat agagatgggg gtttcactat gttgcctagg ctgcaattga actcctgaac    118320
tcaagcaatc ctcctgtctc ggcctcccaa agtgctggga ttacacgcat gagccaccag    118380
gccagggata ttttttgtctt ttgagacagg gtcttgttct gttgtccagg ctggatcaca    118440
gtggtgcaat catggctcac tgcagcctca acctcccagg ctcaagtgat ccttccacct    118500
cagcctcctg aatatctcgg actacaggca tgtttcatca tgtctggctt ttatttatt     118560 ttatttatt ttttggagag atgaggtctt actatgttgc ctaggctgtt ctcgaactcc    118620
tagactcaag caatcctcct tcttcagcct actgtagtgc tgggcttata ggcaggaacc    118680
accatgccca gccctgactt ttattaagcc acattgtgtc aattatccag atcctaaact    118740
```

```
atgacaatgt cattagaggc atcatatcac aaaaacaaga ggtagaatac ctattaacaa 118800
tttacaattt tctattggta agaaaaataa taagaatatt aattctagct accagacctt 118860
catacaaaga acgttctatt caatgaacac cttataattt tagaaatatg gaaatagaat 118920
acgtcactta ttttaaaaaa aaactcagat ctcttatttt cctctgatca taccacagtc 118980
agtttcccac ctgtgaaagt ctttgtatct tctaatatga ttttcttccc cctctccaaa 119040
tcccctccag cccaactgaa gaccctagtc tcccatggag tcttgatatg gtttggcggt 119100
gtccccaccc aaatctcacc ttgaattata ataatcccca catgtcaagg attggaccag 119160
gtggagataa ttgaatcatg gtggtggttt tcctcatact gctcttgtgg tagtgaatac 119220
gtctcatgag atctgatggt tttataaatt ggagttcccc tacacaagtt cttcttacct 119280
gccaccatgt aagacgtgac tttgctcctc attcgccttc tgctataatt gtgaggcctc 119340
cccagccatg tggaactgtg agtcaattaa accttttttcc tttataagtt acccagtctt 119400
gggtatgtct ttattagcag cataagaaca agactaatac aagcctcctg gatcagttca 119460
aatcaccttg atatttctta attccaatgc attggcataa agtaaatttc cttcctccct 119520
tggccctcac ctctctcttg actccaataa gggagagttg tggagagatg gtacctgggt 119580
ttgatataat ttgttgccag ataagttata ataatttgtt aaggaattca agccgtagag 119640
gatgaggatg ctcttttagc atattaggtt tgaggtaaca ggccaaaagg aatagcattt 119700
ggttattaag gtaaaaagag aaataatttt tatgcatgtt agaagggggaa ttttgaagga 119760
aattcactt tttctgtata tttatatatt ttactttta tttaccagga gaaaaggcat 119820
ttgctgccca aggtagaatc ccatcaccat actccttttcc tacatccaat cacaaaatca 119880
gaatatgcca attctctatt cccaagtaag tcaacagacc ctaagattac attccctttc 119940
tcccctctgc aaagcttcag ggacaggagt ccctgacagg cagctgacat ttgggggttgc 120000
atacaaaaag tcaagtcatt gcaagagaag gaagtttgtt tctattggaa gagttagtgt 120060
acaacatata aaaacggagt gaggatgggg atattgtagt agggaggggg ttaaagggct 120120
tagaaaatga ttttttttaaa ggtggacagg ggaagagtag aaggcaaaaa aatgtcatcc 120180
atgtgggaca tcttctgaac gcccaaggag aatctttggg gatacattcc ccccaagatt 120240
taaagaagtg gcttcactcc tgagaatgta cagggagcgg agaagctaaa ccaggagcaa 120300
catccaattt cttttgtctct ccttctcttc tcactgcaaa ctctgtacag gtttggcata 120360
actatctaaa ctttctagta aaaatcatag ccttcatgaa gatccattgt gtatttgatt 120420
cacagaaagt tggtattgaa ttgtaaaaca cggctacaaa tttctccctc tccaacaggc 120480
gtgtcatttt ggaatgtgtc ttgctgctct tctcatcaaa ggtaaagtcc tcttcttcac 120540
cttttaacct agagtagctg tgcaactttc tttgaccaat caaatatggt ggaagtgatg 120600
ttgcgtgact tccagatata agtcttaaag agattttttca ctttctgctt tcactctctt 120660
ggaatgttgc cctgagatca ccacaccatg aagaagtctg gggcgaaagg ccatgtggag 120720
tgagaggctc agcttcccag atgatctcac tgagcacagc ccccagccac ctgccagctc 120780
aatgcaacct ggtgatggac ccaagcaaat accagcagaa gaatcacctg gtcaacccac 120840
agaatcatga gaaatactaa tttgttgttg tcttaagcca gtaagttttg agagagtgtt 120900
ttaactgttt cacctaagtt tggtctctta acatgaacat aagcactttt ttgcatttgt 120960
acatcctttg tactcttcct gttcataccg agaaagcttt tgcaatgcaa aagctcaaat 121020
gtattggaat tttagaagtt taagccttga aggactctgt acaaaaccat gccaaaaacc 121080
atatattttg aagaatatgt tctcagtctg agccagtttt ctatttccac ctcaaatctt 121140
```

```
gattggtgca gactggagaa aggagaagag agtcagggt aagaccgtgg gtcggaggtg  121200
gatatcgaca atgtacctga gtaaaagccc tgtagcctct caccatgttg gaataccata  121260
tggcacaact acatggaccg ccatttacat agagtaggat gtttagtact gcgtcttgac  121320
ctttgaaacc agactggtga gaggactcac caacaaaagt gaagctaggg tcataggccc  121380
taccttggag attggtaaga ccccagagtt attccttgcc caatgttaag taagaacaga  121440
aaacatttct aaagagggtc ctgaggcaga caggtcttaa gcagtcccac agccctcatg  121500
tgccctagaa agatgcagag cgcccagaag cggttttca gtgcaggtga aatggttta  121560
gatccacatg ttttgtaaa ttagttttta ttggaagaga ggcaaaccca tacatttacc  121620
tgttgtctat ggctgctttg acactacaat agcagagttg ggtagttgtg acagagatca  121680
tatggtacac aaagcctaaa acatttacta tctggtcctt tatttttaaa aagtccttat  121740
attagatgaa acacaaagaa ctggtaaaac ttaagccttg tgtaataata caaacaaaa  121800
atataccatg tagaccataa tcaaagggcc cattgtcttc agccgctgac attgggacca  121860
gggtgtagtg tcagaacatg aaagcctgga tacctacaat ggcctaattt tctcatacaa  121920
atgcatccta ccactcccat cccatacctt atgctagata ggatccatgg aattagctgc  121980
atctccagtg aaacaggaaa agtccctgat tttactgaga tttagctatt gtcacatggt  122040
gtaacaggga tttaagagaa aaaataacct caggtataga cataggaaaa taatgttaga  122100
ttaagtttct tatacacctg gttctgtctt cagaaactgg cacccactat aaagccttcc  122160
atagtgataa ttatcgcaca aaatcgatac aaaggaaata cctgctgaat gttctgcctc  122220
agtaggtttt cctttggtct tttaccttag aaaactgcat gatagcattt ttctattatt  122280
ttgacatttc atgtaggaag catgttattc acaacttatg ttttataaaa tcttttctg  122340
atgatgatga tgatgacact tgttaatttc catctccttc cttcactgta agttttcta  122400
ttccctgaga caactatttc tctcacttgt cctaaacccc aaggatacaa gagatgcata  122460
ggaaaatatc tatgaagtgt gtgggaggag acaacagggc agggttccag aggtctgtgg  122520
tttattgcac gtaaaacact ggaaagtgct ttggatgata aggaagtagc ttgttgtcct  122580
ttgcaatggc ctgacattct tacactgaga aaatcttact ccccactttg agctgggatg  122640
tgggagctgg gaggacattt actgagtatt aactctgtgc caggaattat tcctacatta  122700
tctcatttag tctccggaaa accctacgta acaggtgaga agacctcagt gacaagctca  122760
aagatgcata gctaaagagc tgaaatgtaa aagcaggtct gccagactca aaaacccatg  122820
ctctataaac tacatcatag aagttgtaaa ataattttac cttgaatcca agggtgaata  122880
atttgtcatg gttagcttgc cctttggcat tcataaacaa tttctactgt cccagttttt  122940
gttccattca tataggagta acatgtggaa gtattaagca atagaaggct ttgttttcat  123000
gtataaattt ttacgatatt ttcaaatata ataaagccaa aattgttaat ttcacttcat  123060
gtagagattc cttcaaatat aagatgctat gaaacagtgt cataccaaaa agcaaacaca  123120
ctgatttcta taatcaaaac attgaggaac acaggaaact ctagataact cagaggaaaa  123180
agggagtaca aaatcgggtt gacacaatgc ttcatttaag aataggaaca ttgtttgttc  123240
atttgggtac tttataactt taagtataat gaggtttctt taaaaaattg taacaatttt  123300
ggtataattg tataataact tggtatgtgg tattttatt tctatttatt tatttattta  123360
ttttgagaca gagtctcact ctgttgccca ggctggagtg cagtgatgtg atcttggctc  123420
acagcaacct ctgccttctg ggttcaagca attctcctgc ctcccaagtg gcctccacgc  123480
ccagctaatt tttgtatttt tagtacagac agtgtttcta ctaaatgttg cccaggctag  123540
```

```
tctcgaactc ctggactcaa gcaatctgct ggcctcggcc tcccaaagtg ctggaattac 123600
atgcatgagc ctatcacact cagccgtagg tgttatttt aaaacatatc caaaatgatt 123660
tggatcattt ttaaaatgat cctaagtaat tctttataat attaatagta taatttggtc 123720
cattaaatta taactagaaa aaaataaata aaattcttcc aaattgatat attgatgtaa 123780
aaataagggt ctctccttta agtctctcca taaactttag ttgagagtga aagacttttg 123840
gaccaatgat tcttaactaa agcaatttct tgacagaagc aaaagtgtga aatgagaaga 123900
tacaataaat ttaacatcaa aacaagaact gtaagttta tcatttaatt gtattgaaat 123960
acatacaaac cactagatat gtggaatttc agaggcattt aaagagtcat tctaaaagta 124020
tatgaaatta tttcatgaaa aggtcgatca aaataagaag aggatcctca taaataaaaa 124080
tgttttataa tatctcgatt ataaaagtaa tttcacagta actttccctt tctgcatctt 124140
gtgaaacaca atagacctga gacagcctgt cagtttgctt tatggaattt gacttttttgc 124200
agcctcacag accacgatga actggtatta ccagttttgc catcttatct tttatttaa 124260
acagcaatta aacactgcca taatatcata taaatcatta ataatgttc cagaccacac 124320
acaagtggat gagttatgaa agactgaagg attatattac ttttaaaata ttttgcttag 124380
atagaataat ggcaataaat attagcaccc tttgttat acttttacca aatattgagt 124440
agtttcaaag gaacacttac taaatacatg caatacataa ggaatcataa tacaataaac 124500
aactatgtac ctactactta cttaaagaaa aataatattt ttgtatctgt catggaaccc 124560
tctcagatcc tgtccctcc taattttgaa ttttgtgttc aatcatttcc ttgttttct 124620
ttagaggttt actgcatatg cctaaacaaa acactggtta atttcatggt ttttacagct 124680
ttgaacatta atgaagtgta tcgatattat tttgctactt gattttttg cccaaaattg 124740
gatacatgag attcgtacat gttgttgcat gtagctgtaa tcaattaact ttcacaccgt 124800
attatgttaa tccattctgc tcttgatgaa catttgaaaa atctccaggt gcatgtttat 124860
gtgtgagaga gattacaaat agtgctgcta agaacatttt tatactaccc tggttaaaga 124920
gcatgtgaaa gatcttctct tggaaaata actaacagtg aaattgctgg gtagtagcaa 124980
atttaccaga taatgccaat tattttccga agtgcttata taacacaccc ttatggtttt 125040
aatggcatgc ttcttactaa atttatctct ctctcacaca cacacaggca cacacacata 125100
cacgatatag agatatatcc ttttaatata cattactcct tttctgaaaa tgatttata 125160
tactaaaaat ctaaataata gtattagtgc tggcttttca gaaaacctag aattgtgaaa 125220
gatgtggttg attgggaatt tttgtcattt gttgccagga aacaaatat taaggaaaaa 125280
atgggaagaa tgttttagtt gtattttttt tttttttttt tttttttttt gggacagagt 125340
ctcgctctgt agcccaggct ggagtgcagt ggcgtgatat cggctcactg caggctcctc 125400
ctcccgggtt cacgccattc tcctgcctca gcctcccgag tagctgggac tacaggcgcc 125460
tgccaccacg cccggctaat tttttgtat tttagtaca gacggggttt caccgtgtta 125520
gccaggatgg tctcaatctc ctgacctcgt gatccgcccg tcttggcctc ccaaagtgct 125580
gggattacag gcgtgagcca ccgcgcctgg ccagttttat cttaacgat ggaaaaacaa 125640
atgtatttat ctttcatatg ccttctatta cacttctgat gtcttcattt ataggctaa 125700
aatatgcatt cactctattt tcaatcttgg tctttggtct tttaagaag cccaagggct 125760
gactggtgac attcaaaata atgtgttatg caagaaacca atttaggga tgaacgatac 125820
ttcttcagct ataactccta aaaatcatca gaattggaac actggaaaag aattaagat 125880
attttttgtct actctgtaac tctttttgta catttttttct cttataacaa gcatctactt 125940
```

```
taagttgaag aggatccgtt aactatccaa ctaagtatat ttcaaatgct ctaaaagttc    126000
agacttgact taactaaaat cctctaggta caatactacc agaagcacat gcttctcatt    126060
tttatctaat aaagtttctt taatcagtga aggcctataa gaatgtgatg tcccttaaaa    126120
gaaatgcatt gcaaaattcc aaaaaattat ttcttttata ctctctttgt gtaaatatcc    126180
tacttttcaa aatttaccaa tgttataaga actccaaatt atttaaatta gaatcaagca    126240
aatggtaata ttatttttaaa atgttcctag agtggtaccc tcccagctct tgcactctgc    126300 tgttttttaat gtgtgggccc ctgatggtct tccatgagaa ccagaaatct gtaagactct    126360
atcttgcatt taagataaag tggtttaggt acttcattac gtgttcattt taatggtgca    126420
gtgcactcat taatatgctt tatcaacact aaataagtaa cctagtgtat gtatgagcaa    126480
tcattgatat tagcctaatg agaaattact gggcagtaag tactatgata agaaacatat    126540
cataggttta tattacaaat taaatagaga attgcaaaaa ttttctgagt tttctaagca    126600
aaatatattg ggccctaaat tatttggcta ttgttattgc tttgttgatg gagaaatact    126660
cagcacagag atgcttttct aatctataat ccagtatcac aaaggaagca tccaccatta    126720
aaaaaatcaa aaatcatacc tcaaataata ataaaaatat caatggaata ttaatgattg    126780
cttattatat gtaccaataa ttttacatac tctaatttgt acaaaagctt ttcaggtagg    126840
taatattatt atcatgttgc agatgaggag attgagtttt agaagatttg tgtgaattac    126900
ccaaggcaac aaagctagtg agcagcagag tgaggattca gttcatgcca gctgatgtag    126960
aagctatgtg cttactatac tattcaactc taataagata tgtctttcat tagtacccttt    127020 cttctcatat gtatgaactc tgatggtcca aacatatata agcaccaggt acatacactc    127080
atgcctgaat gaaatgcctg ctgtatacac tatgccatgg gaagtaaagt aaggactcat    127140 tcacccttttc ctcaaggagc ttacaatgta gatcgagggg ataagacgtt aacaaagata    127200
cgtataatca caagcaaaat atgtcaatag ccataagaaa catattctgg caatgcacgg    127260
aagaaagaaa tcctgttggc taagtgggac aaaaagagtc tttataaaga aggtaaggtg    127320
aatcttttgg ggaacagtga agtggaaaat caggattttg cacaaagcat gctttatgcc    127380
aaaaagctta aggtacgttg taggcatgac ttgtttttatt ctggctgggc tgggacaggg    127440
catgtataaa aactgcctag agactgggca ctctttatac tctttgatga atttgtacca    127500
aattattaaa cagtgggaaa ctattgaagt tttttttttt ttttttttt tttttttttt    127560 ttttttttga cacggagtct cgctctgtcg cccaggccgg actgcggact gcagtggcgc    127620
aatctcggct cactgcaagc tccgcttccc ggcttcacgc cattctcctg cctcagcctc    127680
ccgagtagct gggactacag gcgcccgcca ccgcgcctgg ctaatttttt gtattttag    127740 tagagacggg gtttcacctt gttagccagg atggtctcga tctcctgacc tcatgatcca    127800
cccgcctccg cctcccaaag tgctgggatt acaggcgtga gccaccgcgc ccggccacta    127860 ttgaagttttt gaagtaagga atgatatcat tcattcaaaa actatttgtg gggtgtcagt    127920
atgtgcctgg cactgtgaca gatgatggga atattgaggt gaacaagacc agtccatttc    127980
ctgccctcat agatcctaca agttgatggg gagaaagagg ctaattttca ctatgactaa    128040
gaatgtgatg gccctgcatg aaacagaagc aaagcctctg agtagaaaaa actttgatgg    128100
tttggtttac atttcctcta ctacctttc ttaaagtaaa tattttatttt tagaataatt    128160 ttagattcta ttactattag agtctaatat catttaaagg taatttagaa aatttatttc    128220
aattactatt aaggttgcta tttgatcatt taatgcgtat ccttctatgt cataactctg    128280
tgggacaaat ttcagaaaga ctaacacatt taaacatcag ttagttgcac aatctaaact    128340
```

```
gctactgcaa ctaggtagat aaacatgtta aagaaatgtc tttggtacat ctgtacttgg   128400
ctctgatccc tctgagcata gcaagttaca aagtgttgag ttggaaaact ttgtaatgac   128460
caaagaggta ttacaaatac agaaaggcca atttttaaaag aagtcaacga gaaaggtata  128520
caaactgccc aactataatc aaacacttgc atgaaaaaaa aattgtaggt aagacctgct   128580
tgtattaaag gtttttcaca gaaacataaa actcagagat ttatgaaact aaaaagtatg   128640
gaagattact gaattaatcc tgaggtaaat aatgtcccag tagaaattag cagtaaggta   128700
agcactccaa aacaatcaaa ttagcagggg gacataaact gatatgaggg taaagggacg   128760
actagtgaga aataagaaat cagactacag ccaaattaaa aaaaaattta aatatattga   128820
tgcttagttt cctttaagca ttgcaacata tgatattgac aaatgtggtg acagctggta   128880
aaaactgtat atgttaattg ccaacatcac ataactaata tttactataa aaagtgtccc   128940
taaaataact ttctttcatc atcagatagc catatccatc tagcattccc tgtttatgtt   129000
ttgaaatgta tgtattacat ttttttcttct ccttttagga ttaaaatata aagttttatg  129060
ttccctaata tatctacttt aagaatattc taaatattga aaataaaaaa ttttttaata   129120
aaataccact gacagctgtt ctctacttat catttcttag cagggtgaag actatatttg   129180
ctcacataaa ttgtgtcctt ataacagaaa aagcttctta gggctggtgc ggtggcttat   129240
tcctgtaatc ccagcacttt gggaggcgga cgcaagcaga tcacttgagt tcaggagttc   129300
tagaccagcc tggcctacat ggtgaaaccc cgtctccact aaaaatacaa aaattagaca   129360
ggcatggtgg tgcatgcctg taatcccagc tacctggaag gctgaggcag gaaaattgct   129420
tgaacttggg aggcagaggc tgcagcgaac caagatggga ccactacact ccaaactggg   129480
tgacacagtg agactccatc taaaaaacaa acaacaacaa caaaagaaaa agcatctcag   129540
aaaaacgttc cccttttttca ttgattccat gcaaatgata cttcacccta tgtttactt   129600 gtcctgaaat ttcaaagcag cagaaattct gctatacatt atcctttttat ctggtattta  129660 ttgaaaatgt atttggctat gatttgaaat atataacata gtgtcaggtt tattttctca   129720
tgtaacgagt caagaagtag gtggttgctg cctttctttc agttattcaa cactataatc   129780
aatcactgtc ttgtcttttt atatttctgt tcgctatctt ctatgtgttg ggtttccttc   129840
ccggtgggtg tcatatcagg gtcacaaaat ggctgctatt gcccagtaat actcgaatgc   129900
tcgagcgagg gcaggatgga gggaggggct gctagctgta tctgtctcct tttgtcagaa   129960
aagcaaaagc tttccgggaa gctctcctag cggcgactcc ttacatctca aggccacaaa   130020
tttcaaagag tggaaaagca gaaaacaaga ttctcatttt tggcaccatt gtgagacatt   130080
gcctaggaaa ggcatattga caattcaaac aaaatcttaa attctagtag caaaggacac   130140
agaggaatga atatttggta cgggacagaa aggatctgcc taaatgccct agttcatttg   130200
aatgtaaaat tcttaaaggc tgggattgtg cctgttctct tctttgtgta taggactcag   130260
atcataagaa aaatctttga cactacaaat tctatacact aaggcagtat ccccaaattt   130320
cattcaattt ttctaatatg ggggtgctac tgagcacaaa actagaaaga gattataaat   130380
atacatattc ttggtcagtt tagactacta tagcaaaata tgatgcacta ggtggtttaa   130440
atgatctcct cttagggccc ttgctgtgtc cttgtatggt ggagagacag ttctctggcc   130500
tctcttctct tcttataagg ccactaattc catcatgggg acttcaccct cacgtcctga   130560
tctaaacctg agcaccccccc aaaggttcca cattcaaata ccatcacact agaggttagg   130620
gcttcaacat ataaatttgg gggaagataa gcgtttagac cattatttat ttatatgtta   130680
aaaataatat agaatattcc cagaagtcaa tttttgctcc atgtattaga atacttatta   130740
```

```
aaccttccta tgcccagcaa aattgtagac actgaaaaaa taccaacaga aaatggtcca    130800
gcttttaatg catttaagct gaaataagaa gtggtgaaca cagatccaaa ttgaactaaa    130860
atgttatgta atctataata gcaacctttt atctggtgtc tattatgtga taatggtata    130920
acgtacttta tctaatcttc acaacaacac tgctaggtag ttattagcct catcttaagt    130980
gttagaaaac agagaacact gagaggctaa gaaattcatt caaggccacc cagggcataa    131040
gcagtggagc tgaagtttgg acaagatttc ttttctccc caagccatgc ttgcacataa     131100
tgcacatacc actacatgct gattaattca ttttatgaat aaaatcttcc ctcttataat    131160
tctgctttgt ttttatgctt tttcattcct agctttctca ctggtgactt atgtggatga    131220
atcaatggga acaaggtcag atcatggaca gatgagaaaa taatgagaca ttagattatt    131280
aagagagatg aagttaagag tgagaggtga atgaaaggga agaaggggtg aaagctcagg    131340
attatgaagg gaataaacag gaaagaggag agagaagaag agaatgaata ctacccagat    131400
atttctctgg gcactgtgga tctgatgaaa tggtggtatc ccaccctgta accctgtctt    131460
ctctgatctc tggccaagtg tgtggcttgg cactgcacaa ctaacagtta gcagcattct    131520
ggggagaggc tcatggtagt gaccaaattg cactttccct agctattctt gtgttctaat    131580
cctcccctga aggtctttta tggttaatct caaaccatat aaatatttaa ctctccttt    131640
agttacattg cagaagcctg ttctcaaaca agtataagtt tcagtaacca caaattgata    131700
ctaatctacc ctaatgtcac tgtgttcctc ttcttcaagt gagttgaaag catggatcca    131760
tacaatttgt cttgttcagt ttgtacctac ttgtatcttc cattaacaga gcatagactc    131820
tcaggtatgg agaacagatt aagatccaat tactcagcca aaatttcaat ccacctctct    131880
ccaggacatt ttttgtttt tgtttttgtt tttctttaac atcctccaaa ctggtagtat     131940
agctatatcg agtacttcca gtccatggaa cctaacactt cctcaagtag tccttttccat  132000
gcttagacaa cttcgacttt agagtgtggt ttcttatttc accagtcagg atagctaagc    132060
tgttctgcag taacaaacag ccctaaagtg tcagctctaa tacaacagag gctttctttt    132120
tttttttttt tttttggcta acattatgtg cctatcaaat cagcttggct ctggtatata    132180
ttgatatcca tctgggatcc tggctgaggg agaagcccct ctctgggaca tttctgatct    132240
catggcagag gaaagaggt cctggaggat cgtatactgg ccattagagc ttccacatgt     132300
cattagccaa catgcatcac atggagtcat cccacagaga aggacagggc caggagcaag    132360
acaacccaga gaacagccgt aaatatctgg aataacagtg caatgtacca catagttatt    132420
gagtcaaatc cttttccaag tcatatccct ccttccccat tgccttttct ctttaccagc    132480
tctacaaatg ttaggaatcc ttagccatgt tttcttcgag ctgtctttct tctagtctaa    132540
ttggctccaa ttcctccact gacctgttcc ctgtatctag tggtcttatc tgacattctc    132600
ttgagccttt tcagctgtct caagtcaact ggtgagagaa ttgttggtct attctccaaa    132660
ggaagtggtc ccttgacata ctttccttta ggatgatggg tttggcgatg tggctgagcc    132720
ttctagacaa aaaagctttt ccttaaacaa tatctcaact aatcagtctc caaatatttt    132780
agtagcttaa atctttaggc ttttcacaaa tgcccagaca ctttgcctgt tatatattag    132840
aatgtagaga tgtttgagca cttccagagg gcaaatgtca catccctgac tatactttag    132900
gtaacttagc aatatatata catggttgta ttgacaaaac tcctcaagcc tactattttt    132960
tcataggact ggctcagaat gtggactttg gaaataacca gtcttggatc aaaccctgat    133020
tccactcagt actacctata cgacctttga caagttaatt aatcctgagc tcttatttcc    133080
tcatctaatg agatacagac aataagagtt atctttctca tgtggctgtt gagaggatta    133140
```

```
aatgacaaca gtggggctca atcagtgtct tcttttgtta ccatactggg gtcctagcac 133200
tcagagctat ttctggtctt actcaaggac caggtcctct agcatccctg ggtttaccat 133260
ggttatgcat agctccctcc tctctcccag gtgtccttct ctcctcctga aatgtttcag 133320
cctcaagtca gcatcatccg agcttgacca gtatctctca aggtgttgtc caagaacaag 133380
ctgcactgga atcacctgga ggcccacgtg gctccatttc agactaactg acagagttag 133440
aagatgaaac tagtaaatct gtattttaac aagcttcccc cagctagagg tgccagataa 133500
attataggac atccagttaa atttgaattt cagataaaca atgaacaatt ttcagtataa 133560
gtatgtctgt cccatgcaat atttggaaca tacttatact aaaaaaaaat ttattattta 133620
tctgaaattc aaattaaatg gagtatcctg tacttttaat tgctaaatct ggcaaacaaa 133680
tctcagggat tccaattctt actaaatttg aagaccactg gtttaagata tttggcaaaa 133740
atctcaaatt caacttcatg agcttccaag gagggaggga gggaagaac gaaggaagga 133800
aggaaggaaa cgaaggaaa gggaaggaa ggaaggaagg aaggaaggaa atgaaaggaa 133860
agggaaggga agggaaggga gggaagggag ggaaggaagg gaagggaggg aagggaagga 133920
agggaaggaa gggaaggaag ggaaggaagg gaaggaaggg aaggagagaa ggagggagga 133980
aggagaagag aggaaagaaa gaaggaaga aagagacaaa gagaggaaag aaaagcaaag 134040
caagcgaagc ttatagacgg aacacagatg gcccatgcat ccacaaaaca aatatgcaca 134100
agaccaagta ggttagcatt tgtttcagca gccacagtgg caaacataga caatccagca 134160
gccagagaaa aatccacttc cttgtttctc tagtttggaa ttgggcttta ggtgtctctg 134220
tctccttctg ctgctttctc cttttttttt tttttttttt tttttttttt tgtctaaaca 134280
tctccatgct atgctagcca acacctactc atcctcattt ggtatttcct cttttgcttt 134340
tttgctttcc tacaaagcat cttgggccca tcctcctctg tctgccccaa acatcagaat 134400
acctaatcaa atagtcatat agccatcttt ctccctctaa tattaagtgt ggactccctc 134460
aatttttagtt ttctgatggg attttcctaa ttctcaaacc attctgtctt atgtgtacta 134520
gagtaatgca ttgtgttttt ggttcgtgta catttacaga ggccttaaaa gagacattag 134580
ctgattttttc acaataaccc cataatcgag gcagatgaaa aacggagccc ttttattcct 134640
aggccaagac ccttcttact cagccattgt ctcatctcag gttattatac tcacatcatt 134700
catttgtcat tttagaatag tgattaaagc acagctgtgt gccttggtta gttttatttt 134760
tttcttaacc aatctaagct tccatttcct catttgtaaa cttaggttaa caatagtgcc 134820
tacatcatga gcactgggtt tagtcagatg atcaaagtct tagcactgtg actgcaaatt 134880
gtaagcactc aaaatattag ccattattaa aactatcttg tgggccaatt cttttccagg 134940
cccagctttt ctcttgttgt ctttcagcaa atagagatat aaaatggaaa acttagacta 135000
aaaccagcag aacaagaagt atcaatggct gcacaaggaa gtaatgcaga cctatgctaa 135060
attttctctt ggtaaacact tccttttttca taccctctc ccttgaactt tttcacctcc 135120
actcctacaa ttttatgtta tgcagagtca aaatataat catcctaaac taggctcagc 135180
agtgtggaca gtaactgatt gaaatatgag gttctttaat tagaagcagg aactagagta 135240
tagtactaag aataatggta atataattat ttgcatcttg tctaacttcc tcatttacac 135300
tggccttctt catttctatc tcattccctg ataaatatgg tatctcaaag ccaaatgttt 135360
gggactccaa tattatcatt gtgttcacct tctttaccca ttagggcctt tatatgataa 135420
taagtgtaat atgatatccc caatgaatga gatagagtgg cccatacagg agcgacctca 135480
aagcactttt tctgtactgc agatgcagtg caaaattagg aatattagga aaattacgac 135540
```

```
tgctttcttc agaaaatact cagggcaata ttgttgtgga taatgggaaa taactggtgg   135600
tttttgaaca aggaaagtga atgtcggtta tagtattgaa tagaatagtg ttctagaaat   135660
agacaatcta tgtagaccag taagtctgaa gtcagggtca ctgtgcagca acagaggaca   135720
taatctgaga ggctacccttt tcatgactgt gtcagcaaat acaccaccat tgcttttcat   135780
cttagaggca gcacaaaact atgcaaaaga aaaatcaatc aagaacatat ttaggacaca   135840
gcagggaagg ctcctataaa cattttttg ggaagaacat agatatatga tgcttttta   135900 aaaagttatc agtggaaaaa attggaattt cacaggactt tgttatattt gttttggct    135960 tagagtttgt tttgtttggt ttctttgttt aactatattt ttggaagggt agaaggtgga   136020
tggacattgt aatcttcttt actatttaga aactctaaat gtcttaatct gattcagtcc   136080
aggactgcat aggaattact tgattttgc catcgacaca ggtatcataa tcccttact    136140 gctctatccg gagaatgttg tgttttttcc cccctttaag atgaggaatc tgtcagtatg   136200
gttgctccct tatgactaac aggttagatt atgcttaagt attctacgtg gtccctccca   136260
taaaaactgc ctcagaaacc tccagtgcct caaatactct tgtccttgaa tggtacaagg   136320
aagtagagga ttcctggggc atatatgata cttaatctct ctctctgcct actgacattc   136380
taacattttg gtgagcccca ttttatttgc tatggaattt gacaaacagt tcaatcccac   136440
aaacatcgag tgagcaagta ccatgtgcaa gcaattcatt caatgaatat tttcaactcc   136500
tactacgtat catgcataag attcacccta atgaaggaga agaaggagga gaagaaggaa   136560
ggaaggagga caaggaggaa gttgggagga atccctgttc tcaggagctt caaatcctgc   136620
tggctagaag atatgtaaac ataagggcaa tagaaatctt atgctgcctc tgtggactga   136680
gagtgacagg ggatagatcc ttgaagaaat agcagtgtgc ttgggggaaa cagatgctgg   136740
gcaggcaaaa acttctcctg aaaaatacaa actgtgactt gagccatgcc tgagggagaa   136800
gtagaacttt gattccagtt gaagcatagg cagtagaaaa tgtatggatt tgagagttaa   136860
aaataatttt gaacccatct tcaccaatga gctgtggtga ctgtgaataa gttatttgc    136920 ttctctaagc ctccactcta aaataggaat tgtgatgttt agcccaaagt gttgaggtat   136980
acatctcctc aggcctcaat gcagtcttgt ataatgactt agagcatgga ctctgaagcc   137040
aaactgcctc agtttgaagt ctggtgctaa cacttagcta ttaaacttgg gcaaattatt   137100
gaatttatca gtacctcagt ttccacatct gaaaatagaa atgataatag caaactgacc   137160
tctcagtagt tgtaaattaa acagacaggt taatgatata aagtacttta ataagtgact   137220
acacatggta agccctataa ccatttgcta ttattaccaa gtgtttagtg atacaatata   137280
agccattaaa ttaccatatt acctggttag tagatgctat ttttattat agtgcactgt    137340 gataaacatt gtaagaaata taaatgttcc ttgtattttt agggaagaca tgaaagaaat   137400
tatagcctag tcataagtga cactcacaag taatcataat aaagatggta tgtaataaat   137460
attgcaagaa agatcagata tgtccaactg atagttcaga agaataaggg atcaggaaga   137520
aaaaaaaact ataatagaga catggccttc tcatcatggc ctgggcatga tagcaagacc   137580
ccatctcttc aaaaaatgaa gagatatccc ctaggagcat gcaatcctag aggaaggcat   137640
gggtgtacct tccagattgg aaggagaggt aatgattgtt gagtcagcaa tgcaagatta   137700
ggtagactat tgctgggtgg attagtgcag ggaatgcctt ccctgatgaa accaacaatg   137760
gttgcaaagg catagaagca tgaaagggca aaaagtgtgt gtgtgtgtgc atgttacaga   137820
aaaagcaaag cagtcaagag agatggaaga tgtgtacttg gggacatcac atgagcgatg   137880
gagacacaaa gatgaataag acatgaagga aatattttg gatgatgcat gctggagact   137940
```

```
gttttttgttt tttgtgtcct tttgtccttta acttcctcct tcctttttc cttcaaaata  138000 catttactga tacctacaat gtgctagaga aatatgactt tccttatatc acctgttata  138060
taacagagtt ttgtcccatg ataagtgata aatagaaat cgcctcatat gaaacaaagt  138120
tatgttatat cagaaatgtg ataaataatt ttccaagtta caccgaaact aggcccaaa   138180 tagggctctt tcattaaact cttttgttcag ttgctttctc tcactccat gtccctaaag  138240 tacatggata gtagagaatc cttttttttt ttttcagttt atgtgggctt agcaaagagt  138300
gggcaggcaa tagagacttg cagatctcaa ctgaattact ggagaattta attttaaatg  138360
ctctagaagg ttatcttctt cacaacttgg tggcaaattc tttcaggaac tgaaagttgc  138420
atgtgtttta aaggggcata agcttgtgga gaacctttct ctttggttta gctgcatcga  138480
tatgctgatt ttttaaatg cactgaacat gcaaaaatga gtatattatt gacctcaaat  138540
caatgcccat cactgtttct atcttataca gtgagcttct tggcttttta atattttcat  138600
tgtgaagtta ttccaatgaa gacaaaattt tgtcaaattt attacccagg gagctttcaa  138660
aatgaagcag agagactttg accgagcaat ttcacttctg gaatttatt ctacttatgc   138720 atacttatac atatgtgcaa agacatatat atctgaaagt ttattatttt tcgaagcat   138780 tgtttatagg gagaaaaagc aggtaacagc ccaactgtcc ttcaaaagag aactagttaa  138840
tttatgatat atccatataa ttaatattat tcagtcatta aaaagaataa tatagatcta  138900
tgtgagctta tttggaatga tctccaggac atgttttaa attaaatcac aaatacaaac   138960
aaaagaaaga gagaaagaaa agtacagaat aggtataagg aagatttcca tttgtgagac  139020
ataaatattt atctgtgctt tgtatattta tttagtacac atgaatgcta tgtaggcatg  139080
gaacatttct gaaagatca gcaagaaagt acaaatagtg attatttctg gatgggaatc   139140
tggactacgc agcaggcaca ctttttcattg cctgtcctt gtattatgtg attttacca   139200 tgctaatata tttttattaa aaattaatta aagaaagaat aactactgga gataagccat  139260
ttttggtcaa ttccatagtg gctagttaga ggctaagtaa tatgcaatca tgaaattaat  139320
gctcaaatta ataaaacagt atttcccaat cttgatttta ttacaagttc atttctgagt  139380
agttcaagaa cttgtagaat tatttaaag atctcaaaat aaaagaaagt ggtaatctaa   139440
ttttgaaagg aaatatgttt cacacagttt gggaagaga gaagtattgt tttcaaatag   139500
ggagcagtgc cttagtgagt aatttcattt gcattcctgt gtatctttaa gctgagtaca  139560
aactaagaaa aactgttctt gcagaataca ctgtaaaatt actttaatca gtaattactt  139620 tgaccttttcc ctatcaaagg tcaaaacacc ggacagcctg ttgctcttaa catcagctct  139680
tctgcgtaat atttctcttt gctctggaac acaattagct cttgggaaaa gaggccaact  139740
tttcagtttc tgcctttcat ggtttctgtc ttccctctg cttcagtgca ggtcagtcac   139800
acagataagc attatgccca gaataaaact ggctctgttt atctggacta ataaatgaat  139860
ggaaccagtt attttcattg gcttggtctg gaaggaaacc aaaactaattt ccacagacct  139920 taaattggac ctaatccaag ctacttgtcc tcactaataa gagcaataac aattagtata  139980
aaagcaaaaa ttttttacaaa agcaatccat atttactgct gggcaagaaa attggataaa  140040
actaggaact aacatgaggg actctgaaag ctctgagaaa tccacttcat ttgtatttca  140100
atgagtctga gctttgcagg tgaatacaac cttttctttag gttctagata ctccagtttc  140160
tctctggtca attttttctaa tcaagttgtg ctaacttccg ctgatgagca gaaagtatgt  140220
gtatggtaca gtcaaaactt ttgcactttt gtcttactta agaaacttaa aactcacatt  140280
tgtattccta gggtttctga caagtcggca tactttattt cacaatgtgt tcatggaaca  140340
```

```
gtgagatttt gacttccatt gtgcacatgt aataaaatgt tctcattagt gatattcact   140400
cagtgtatga aagcagttac tgcctctgcc caaaaggcat tgctgtttcc atttaagatt   140460
tatggttggc cttttaatta tactcccaac actgcccta aatatatccc catggaaaaa    140520
tatataaaag tatttcactt aattattatc ttgctcaaag atcagggcaa tatcttggag   140580
ctgcttccaa gactattgct ttatgatttg aaagctgttt agctattttt accaaataat   140640
taattcagat atatcaagaa tagggtaaac tctttattga aacgatttgt agggaactta   140700
aagagtaatt aattttccat atgtattttt aaatgaaaat aacttattct ttctttctga   140760
tttaaaaaaa tgcctacttg tagcaaaaca aaataggggga attcattaaa aaattgttta   140820
aacccaatgc aacccaccta tatttctagg taccaagaat accactatga aaatgttcat   140880
gaacatcctt tcagacattt atatggatag acattaggca tacacatttt ttaaaacaaa   140940
tgagataata ctgaaggagt tcaggacatt ccaccccaaa atatgtccct ttggcgtatt   141000
gattattttg atttaaagac acctgggggct gggcatggtg gttcacacct ttaatcccag   141060
cactctggga ggccaagata ggcgatgact tgaggtcagg agttcagatc agcctgacta   141120
acatggtgaa accccatctc taccaaaaaa atacaaaaat tggccaggag tggtggcact   141180
cacctgtagt cccagctact tgggaggctg aggctggaga attgcttgaa cccaggaggt   141240
ggaggctcca gtgaactaag attacacctc tgcactccag cctgggtgac agagtgagat   141300
cctgtctcaa aaaaaaaaaa aaaaaagaca cttagaagac aataggtatt agaagggctt   141360
tctgaccacc ccttttctat ttaaaaacag tccataaaat ttcctatgaa aaagctgcct   141420
tccttgtatc aaaaagtgaa gaacatcctt atcagcagag actgggaatc aacactaaaa   141480
tgaatccata tacacaaatt tactaaaata actcttattg tccaccagtt ttccccactt   141540
aatgttttat cacttccccg caattaactg cccctagccc aaaccacttt gtcttgtcat   141600
ttcttcacaa attcatcact tctttgtcca aaaggtacat atgctttctg ctctggtcct   141660
ttcttcatgg tttcattttc ctgtgaggat tcccatgcac atgtgccatt ctaataaaac   141720
atatgtgctt ttctcctgtt catctatcta tgtcaatttg acttttaggt ccagtcagag   141780
accacaagaa cgcagaagac acattttatt tcctctataa taccatactg ttttaaaatt   141840
aacaatatat tctttaaaat atgtaaatat aagtagatga ttagatagag agatctccaa   141900
ctcaccactt aaagtgctgc atcatattag attctgtttt catattttac caatccacta   141960
ttgatgaaca tttaagtaat ttcaattcaa ttttaaataa cactatagca ataccaatg    142020 tgtgttttttc tgattatctt tctaggtttt attcccaaag gttactgact atggatattt   142080
aaaatgtttg aaatgtattc ttaacttccc cttcaacaat gttaaaacca atggttttaa   142140
tatccttaaa ggtagtttct actttacaca aaagttattt ggaaggagat ttggggtaaa   142200
ggaagtgatt aggaggaata gaggattaag agatgaggat gatactggat atatttctta   142260
aaaaagtcta tgagaagata gaaaatgag tacagcttag atgctgaa atatcataac      142320 agtaaaaaag gtatgtgtta catgaagtta ggcaccaatc caaagaagtt gctgagagaa   142380
caatcttgtg aacctacaag ttaattgtag gagagaaact cagaagtttt agtatgaatg   142440
agctggaagg ttactgtttc actcaggaga ttagaaagat aacaagagac attgcttaaa   142500 tctatttca aatataatgc taataatttt ttcagtaggc tataaaaaca agtcttccct    142560
ttcctactgc agttaaaaaa aatgcattgt ccttttcccc cctcacactt gtttgtatc    142620 aggaccttct tgtttagatc aggttactaa atatctttag aagacactac atttagaaaa   142680
agaaattatt gttttgaagt ttttccaaag caaataaaga taattcttat acttctatag   142740
```

```
atatttaaat ccaaatgtgt ctgttcaatg gataaaacca tagaggtctt taattttgca  142800
aaacaagccc atggcaaacc catgaaatag aaaaatgtat tattttgaat actactatcc  142860
aatcttcccc cacgctttct ctggtgccca gttttccag gtgacactgc tatacctcag  142920
cctgaagcct ctaccctct tgttcagctc tgtccctgca gacagaactt ctaggtgggt  142980
ccccaaggac cagatttgcc tcactctata ccctctgaat gctttagcct ttgacttgtt  143040
tcctcaaggc actcctaaat gatgctcttt taactgatga actattttga aaattagtga  143100
ctgagggtag accagtgtgt tactactcca agtaacaaga gcaatttaaa agtgtccttc  143160
agtgcttcag tggaaagaaa tctgttccat aaagggaatt caggcttcct gcaacaggat  143220
gttttctgtt caatccatag tcataccaag cagggcaaca gctcttagtt tctagtcaca  143280
atcatagata caggtaggag atactgataa atatttgata aatattattt cattggagct  143340
tcaattctat ttaatttta attttatcag agtaatgcac agatacatgc ttttataaag  143400
taaaatagca cttagagagc ttttaataaa attagcttgc ctgccgcatt gccccacttc  143460
aaaagcagga tcttccacac ttgatttgtt tatgtgtact tctgaatttc taaactacct  143520
gcccacttta ttgacttttc aattttagat atcattattg aatgatatcc ctgtaagaga  143580
aatgaagatt aagcagtctg atgcacgctt ctcaccacac accacaaata catgtccctc  143640
cttccatctt cttattctgt aacagacttt ggggttaaat taatatttaa tatttccatt  143700
gatgtcactg tgtctatcac tcacatctga aagatgccat gttttgtaat ttacatttct  143760
tttctcatat taattttcat tattcctaaa ctttaaaata gccatgcact gttttgtttt  143820
cttcatttcc tatgtgccta tcatttacgc aatctcaaat tttctgatac tgctgctaaa  143880
ctctcagtaa aatcagacac attaggtgaa ctatcagtag tacttctcct ttcatggaga  143940
cattactcct ggggctgtct gtccttttgc ttctctggtc tattgcagat aatctgttat  144000
tcctaactgt atctcttcat tcaaatgaca ataaagctca atatttagtg aagagcaatc  144060
ttgacatgtg attcgaagac ataactttat tttcattttg attattttc ctatgtctca  144120 aataaggttt cttgtgtgag tgagggataa ccaggaatga gcaaatgttt ctgtgttttg  144180
cctataaaac agacacagag tcccaagact gtctctctag aagaattttt ccagagattc  144240
cttagttcat cctactctca aatggctaat tttattcccc ttgcaagtct ttaccaaaaa  144300
tgattttgta gcctgaactg ctgtggtact agaaatttca tctgcttttt tctgagtatt  144360
cccattcctt ctcattttta atcagccctg tatagtttag atttcatgtc ctcctctttt  144420
ttatttaccc tctcattttg aagaagcaaa tagttcaaca gcctcttgag aaggaggact  144480
tgagaggtaa atatattgag gtattgcatg tcaacaatat ctttattctg ttctcatgct  144540
tgattgtggc ttggcacagt gccaaactca aggttggaaa tcattttccc tcagaatgtt  144600
gaaggcagtg ctccgactgg aatggagccc atgctgctgt tgagaggttc agtggaatct  144660
gatccggatt ctgaatcctt gtaatgagaa ctgattttc tctctgggag acttttaagg  144720
tcttttcttt atctctggct tcctgatgat aagccttgct tcatgtgggt ctttcttcat  144780
tcattgtgtt aggttcttaa tcagacttt caatctgaga atgtgtcctt cagtaccaaa  144840
aatgtttatt ctatgatttc cttgataatg ctatcccctc tgttatatct ctttcctgtt  144900
tgtgaaactc ctattaatcc atttatgcct agtgttccat tattggaaca ctaagcttgt  144960
gagagttatt tatatcttac tgcccaaggt catcaccaag gtctgatttt tcacacaaaa  145020
aaatttgcaa cctcctgcat aaatgggtta attggatgtg aaacctctga ttcttgtctt  145080
ttctatactg ttttcatct ctttgatttt tatttcagtt tctgattttc tcaaattttg  145140
```

```
tgtttaaatt cttctgtttt tatttgtgct actgtatttt tttttaattt aaagagcttt   145200
taaaaaattt atttctttta gatagcattc tgttcttttt catgggtgca aaatctactt   145260
ttgtttctgg ggatattgct tacagaaact tttcctgtta ctccatgaat ggtttccagt   145320
atatggtgta ctggctggaa atttagactc tgcatccagc ttaaatgtca atcaacacca   145380
ccattgactg tgcctatgac cttgggcaag ttatctaaac tctgctcatc agttgtctca   145440
gtaaaataga aacaataaga gtatacagta acgcatggca ttattgtgag gtacaaatga   145500
gagcaaaatg tattcggcac tcagaacagt aactggaaaa gaggaagccc atatgatatg   145560
ttattatatc catttcctcc aagttccttt ttttcctgtt ttatttact ctttatcatt    145620 tgtgttagac attttctca aatgcctgat gatccttggc tgtgtgttca tatttaataa    145680
tgaggaacta agaagtaaat tggaaacctt ctgtgtgcct ttgaactcct gaagagccat   145740
gtgggaatat aacaccccac agcttcagtg ctggaaagac ctcatgatag agagtggtga   145800
tcaaggagca ccagatgttg caatcactgc ctgcagccat atcagatacc ccaataagaa   145860
ccgcctcgct gagtccagtc agcacccaaa accatgagaa gtcataataa caacaagtga   145920
ttgctgttga tttgttccac caagtcatgt aacaatagac aaatgatgca gagaagaata   145980
ggccctagaa tgagcaagag ccccacctag tatcagatct tgtgacttga aagtttccct   146040
tcccatctag gaacagcctc tcaatctcta ttcctctaaa atctactaga caatatcctt   146100
gtttgattct ctatagatat tttagtgtta atctttcctt gaagtttaag acaggtcatc   146160
caaacacagc tgaaggtaaa tcggagtgtt ggagatgatg ccactctaag gcatagtaag   146220
ccagttttct aagagttgag ataacacata atgataaatt acctacgaca aacacaatat   146280
aactgttact tggattaata accctctttt tctcttcaca tctcatcagt tccctctgtc   146340
atctaaatac attcctatgc caggaataga atttcagaaa acagtttact ttgcaaattc   146400
aaaagtatct caaatttagg gaaaagaaag tgagatgaaa gtttcagtga agtcttctcc   146460
aaagctaaaa caatcatttg aaaatagatg cccacaaatg ttgcagcttg atttatagag   146520
gcaaataatt cagcattaaa tgaggagcaa catgattgct aagagtatat atgtttaaac   146580
tgtgtcaaca gctattacac tgtgaagagg gatttggatt ttgaacatct tgtcaagtca   146640
agagacgttg tttacattc actgctcact ttatttctgc taccgagaat gagatttgac    146700
ttcttccaaa gaactcattg ctacaaggaa gggtaaatac agagagtagt caaggtgatc   146760
tcacagggga gaaggtaact aagcatccaa attgaaacac ttaaatttaa acagctgtaa   146820
aacatgtaat cagccattca aaatgtaatt gtcaaaactg gctacactta ccgaacattt   146880
cactctgcat ttgtttgaaa tgttttgaaa ctctaagttt aggttgaaca ttatatttgg   146940
ttagcaggga aaatttgcc tattctgatt tacagtgaac tacaggaagc taataagttg     147000
cctgggagat actgactgaa actatgatct gcataggtca cttagttact aattggttat   147060
gggaaaggca tggctaagcc tactgcactg aagatttgaa actatgaaca ccacacacag   147120
gaggaacctt aacccttagc agtcaaatgc tgcatgtaat aatatgcaga agaggaaaat   147180
ctatccttta agtttgttaa gaaccagcag ttttaggagg aatcatttgc cattctctga   147240
cagtttacat gtgtttccct gaaaaatgag ataagtaaa ataaaacaaa aataagcaca    147300
agtttactca gagatgatga aaccccaaac tagattggtg gttgagaaac atgatattca   147360
tggccttcat agtaaaagca ttgttgttaa gcactctact ctcattacct cttttagccc   147420
ttgtaactgc tgtgatggat atgtctatat ctccccctct atatttgagg aaactgatgc   147480
ttaaagagac taagaaatag gttcagcaac catcctgatt tgcccgagac tgagaggttt   147540
```

```
cccaggttgc agaattttca ctcttaacac caggagactc ctgggcaaac cagaatggtt   147600
ggtcacctta tgcagcagca ggtcacttac ttactaactg gttatggaaa aggcatggct   147660
aggcctactg cactaaagct ttgaaagcaa ctccacatgg cagcaagcat ttctttctgt   147720
gttatagggt atcttacttt tttggagaca gggtcttgct ctgtcaccca ggctggagtg   147780
cagtgataca actatagctc actgcagctt cgaactcccg ggctcaaagg agcctcccac   147840
cttagcctcc caagtagcta ggatgacagg tgcctgccac catgtctggc taatttttta   147900
atttaaaaaa ttttaaattt tggggtctca ctatgtttcc agggtgatct caaactcctg   147960
gactcaggcg accctccttc ctcaccttcc caaagtgctg ggattacagg catgagttgc   148020
catgtccagc cttatagggt attttttcatt gtactgattt agatattcaa ccctctccac   148080
tcatccttag acctgagaga tactcactcc atatgatctg ctaaaccatc caaatgtgaa   148140
catcctcccg tgcccctgag gctgaaatgg cagcattcac atgtatctga tacaaaatct   148200 tattttttatg atagagaaaa ctaaagctca gagaggttta agtagttaac caaggtgcca   148260
tttaacttga cttctgtaaa tcaccttgag acttaaagga acaaattgtt tttcctttaa   148320
attagaaatc tttaatacct ggattaggtt caaagggtaa actgtcaagg gtaaatttca   148380
agagagataa tatttcaaat tggtggtatc gaatgataaa aatacataat ctgtaatgtg   148440
tatttgcaag taattaattc ggctgtagaa ggcaagaaaa caaacaggat gggtgaagct   148500
cagaagatgc attaagcata gataagtaaa ttagtaatct gtaagacgtg ttcaatataa   148560
ataaggtaag tggagcatat gcgtgtgaaa atagaaatgg ttgaaaggac gaagtgactt   148620
taactattca tgatatacta attatatatc aagcatgtgt gttcccaact agtcacatta   148680
catgaagtat gtaatgtaac gtgtaagtac tcagaagagg aactcttgaa ctatatatga   148740
aaggtaagtt ttctagaaga ggtgatacct aaaccaaatt cttaaggctc tgagaaggta   148800
agggtgggct ggggagggc attcagatgg agacaaccat aggtagttgg gtatatggat   148860
ggatacaggg taaggaatca ctgtaggtta attctatgaa aatgattgaa gtcaaaacgg   148920
aagcacagtc taaaaagtat gcaggatgga actcaaggag ctcacagact gtcaaggaaa   148980
gaggacgata tgtagcatct gacttactta tattgcaaat aactcaaagc atgtattaat   149040
atctttagta ataatagatc caggttgggc cttgggaata ggtatagatt tggacttatc   149100
atgtcaaaag acattaatgt tcaaaaattt tattaccatg tcatcaaaaa tgtctttact   149160
taggaaccta agaggttttc ttttaatact aatacagcaa ctgaaaagag taaaaccttg   149220
acatgcatct gttaaagtcc catctatagt catcattatc atcattgtta cctttattat   149280
ttaagtaaat ctagactgtg ttaaataacc accacacatt atcttactta atatgtaata   149340
ctataaagta ctatacaata tgctatacta atattataaa ataggtacaa tagtccccca   149400
cttatccatg ggggataagt tccaagaccc cagtggatac ctgaaaccta gaagagtacc   149460
acacctgatg gccatcaatt ggaatacact tctgttcatg tcttccattc acaagtttaa   149520
tgccttttcc atttaaccaa gcacttagca tgcactgtgg ctgtaatttc tgcaatttgc   149580
gatgtgacaa ccaaactggc agaaatttct tttccttctt cacaatttca cagatagaac   149640
atcttagcaa tctcagcata tgattctttt ccttcctaaa gttgacaact tttatctttc   149700
acttaaagga agcaactgac agcttctttt tggcatattc aaattgctag tatccttcct   149760
cttgcacttt ggagccatta ttaagtaaaa taaaggttac atgagtccaa gcgctgggct   149820
gccaggacag tcaatctgat aaccaagaca gatactaagt gactaatagg tgagtagtgt   149880
gtacagcgtg caggctctgg acaaagggag gattcatgtc tcagggagga cagagcagga   149940
```

```
cagcacgaga tttcatcatg ctactcagaa gggtacaaaa tttaaaactt aagaattgtt  150000
tatttctgga attttccatt taatattatc aggttgacca gggctaactg aaactgcaga  150060
ttgtgaaact gtggataatg ggagactact cttgacttaa atagacttta actgaaaatg  150120
aggctctgag agttgaagtt tatacaatca agaagtggca aagttggcct aaaaagccta  150180
atgtatatga ttccaaaaca ataaggtttg tatctagaat cagatacatt aggcttctta  150240
ggccaacttt gccacttctt gattgcataa acattatcag aaatacattc tgataataaa  150300
tattttaaca attagacttt agttaacata actcaagtca gtacaaattt caacaaagct  150360
gatagtacca ggagtcgttc caagtgcttt tcatgattat ataacacttt tctattcttc  150420
catagccatg agcaaaaagc aagaagcaca atctgagtgc caaccctgcc cacaatgttc  150480
agtagacaaa aatttcccat gatactcaaa attgcctggt gcagtctcac ctaccaccaa  150540
taccactgtg aggatttatt tagcagattc atgatctatg cattcttcac catcaacatg  150600
aaaggctaaa tagcatcaca acattaacct ttctccagag taatttatat accattaaga  150660
gatgcagtct gtcaaaggaa aaatgccact gatggtagaa ttttaatcat tgacaaacat  150720
ctttaggaga cattttgtgg ttttcttttt tttagattag ggaagggaga tagagatagg  150780
atgtcagggg gtatgataga gagtagtttg gggaaaagca aaccctctct tgccataggt  150840
ccctcacttt atttgtaatg actctacctc tggatcataa atattgggaa aaaaatcatt  150900
aatgagtgca aattgttgta aatgacaaaa tagaaagtta ttagtcttta gctacacata  150960
tgtatgtgtg tgttatcaat acactgctct aaacactaca tggtgtgtta tgaatttacc  151020
actaaaaaca ttatgcataa attggaacaa ttatctgtat cacgaggtaa gatctacctg  151080
tcaaaacaag gggcttatag tgccaggaaa tggagtggga ggattttatg gcataccccca  151140 ggagaggcac tcgtgattag cggtccactt cccataagac aaccaaagtc agttgactgg  151200
tgaaaaccaa aattcagtgg cttccagggc cacttctact tagaatacca agaaaaatgc  151260
ttctgctgtc cactcacctg caaagaatgg aaggaccttc tccaactcac aggaaatgca  151320
tttctttcca acctgaagaa ttaagagttc gctagtcatt ctccctactt tttgttttct  151380
ttcctgtatc ttggtcaaaa gtgtgggaaa atcgaggcat gctaaagata ttttgagctc  151440
tcctaatcct cagttaaaat tgtctgctct gctgaggcag gagaatggcg tgaacccggc  151500
aggcagagct tgcagtgagc cgagatcgcg ccactcttgg acgactgagt gagactctgt  151560
ctcaaaaaaa aaaaaaaaaa aaaagaagt ctgctctgga gaatggtaat gaaatgtaat  151620
aagagctcta gaatgaaacc ccatacgtaa aaacttttca tcacaccaac tggttattct  151680
ttctgagatg ggcctgaaat taaaccaatc tttaaagaca gaagttcata gcaatctcta  151740
ggatgagaaa acctgggctc attcattcat tcatgcatcc attcattctt tctttcaaca  151800
atatttacca agtgaattct aggtgatgct gcacttccat gtcttcttgt tgagcgttga  151860
agcagaaaac gagtgggagc caaaccatga caattcaatg cctgacactg agaaactaga  151920
aaattcaaat gcagatgggg cttcattttt gtctactgat aatgttttg aaagccttga  151980 tttcctcccc acaactgaat tcccaataaa ggtatgaaaa gttcattgtg caatggccgg  152040
ggaattcctg ggtcacttgc accgcttgaa gaagcgatta gggatggggt cactgtgttc  152100
cccagtgact gtagtaaaga gctgggaagt caaggaccca gtcactttct gagcttttgt  152160
ttcctcagat ttcaaatagg cattaaaaaa acaaaacaaa acaaacctat ttcaagaaga  152220
attaaagaga gaacttccac aaagaacctg atcatggtat gtgagataac atacaaaatt  152280
gctaagtcag gaacttgaac caaagacctt ctggttcaat ttgcaagaga tctacatagc  152340
```

```
cacttgagag ggtcagacaa aaattttact attaaaggag ggcttgactg tttttctctg    152400
gactcctgac cactcagggg ccatgtgatg tgttctgaga aatggtgtca cggcagtaaa    152460
agatagtggc cttcttcaga gtcatgcctt acagagcctc cttagtgttt cacctggaca    152520
aaaagaaaaa cagaatttca cagaaaatta aagccttact ctctttcttt gacaaagata    152580
tttggcaaga ttcatcatac aattccacaa gcattagtca ttgaaggatc caaagcacgg    152640
actgaagaac agaaaaacct gctgatacaa gtcccttctc aggaatggct tggactgacc    152700
aggctggttc ttccacccaa tttggccaat ggatttcaaa gacaaagttt tggacttgaa    152760
tttcggtaac tttaagtcta cggaagaaac ttatcgtttt gacaaacttg aaatatgatt    152820
tgtgtgtact tgtctattct atctaatgag agatggcaaa ctccttaaga acaagaattg    152880
tgttatgtct ggcacattgt aggtgctcaa gaaatatatt cactacatga ataaataaat    152940
aaaggtcaac aaaagcctgc aaaatagttt gtgtgattat tttttggaaa gttttaatga    153000
taaagagtgt ggtaaaaatt aaatagaata ataagaagaa atgaatccac gaattcatgt    153060
tatttaaaaa aatttgaaat tttaaaaata acaaataaaa ataaaaataa aaaaataaaa    153120
aataacttga aaagaaagcc aatatatcca gaaaagcaga gcctgagaaa ctgcagaaaa    153180
atggagcaga agcctacttt atctctggac ttagtgttga acaatatgt ttcctcattg    153240 cttaagccag ttttctatt atttgcagtg aaaaagtgct ataattgatt caaaatcaat    153300
gcatttgctt ccagtggggc atattctttc caataaccac aaggcattgg ttgcttcccc    153360
tagacactcc ttcctctatt ggaagatctg ggaaaccaaa ttagttattg gaaatttctc    153420
tgcctcaact cctcccttcc ctcctgaggg tgagttcttt aaaagagaat gggatgaatt    153480
ttcagagagc ctgaaataca ttttagaaa tcctgttgaa gtactgtgac ccagaaacaa    153540
ggtcccctct ccagtgactg agagattcaa gacactccac agtgagaact ttttttttct    153600
tcttgaacaa tggtgaagac cctctgtcct tgtcttctcc tttgcttctc tttgtgtaga    153660
ccatcattgt tcaaaagtg tacatcacat gagcttctca tgcaaactac atatatgtaa    153720
tttaaatttt tctagtagtt acatttaaaa agtaaaaaga aataggtgaa ataaagtta     153780 aatttattat gttttattta acccaatata tctaaaatat cacttcaacg tgtaattaac    153840
ataaaaacta tagagttatt ttacatttt ttatactaag tcttcaaaat cctgtgtgta     153900
ttttacactt agagcacact gcaatttgga ccagccacat ttcaagtgct caatagacag    153960
cacagttgta gccacacaca aatctccttt acttctgtta cagcataaaa ctcttagaca    154020
cacagcgttt agcatctaat taattatgta actgtattac actgttattg caataatcat    154080
taaacaagtg tcattccaac cccctatctg ttttaatgca atcttacatg aaacagtttc    154140
ttatattgag atataggcca gtcttgatgg gtatagagat gtcattcctc tttatccaaa    154200
gatttcctta ttattcttta ctgaatgtca catttacagc tattagatgg gaagattata    154260
atttattcta gaaacttcta ttttttaaact atgtattaac caaaattaca catgtatggg    154320
gtacctgctt atttctagta agcccactag ctgatgtagc aaataggtag ccaggccaaa    154380
agcaaaattt tgatagttgg cctttgtttt aaaaagtgtt ttatatctga ttagctgaat    154440
tctaactatc ttaggaaata aatcaactaa cagtgtaaga gacagtctac tatggtggaa    154500
agagataaac ttcagagtca aacaaactta accctatcac ttactagctt tgtaatggtg    154560
gatatattca ttagcttctc acttgtagaa tgagaataat aatatattat gtctgagact    154620
gctagtttta tcccaatatc cattctcccc ttcttcatca gtaaataacc accaaaagtt    154680
agctagacac agatgcccag aaaaaagtcc atgtttcag ccctttcttg cagctagatg    154740
```

```
tgtttatgtg gttaaatact ggacactgag gtcaaaataa aagcggtgtc tgtaacttcc   154800
aggaagtatc cttttaaaaa gcagggagaa tgctattttc ttccttatgg ctagaattca   154860
gacatgatgg gtggagctag agaagtcatc atgaaccatg aaatgtaaac tgtgttgaga   154920
acagtagaac aagagcagag ccctgggtct ctcctgatca tggaatcgcc accaaagccc   154980
agggttttag aaaagaaaga aatgcatttc tattttttg agccattgtt gttacttatt    155040
ttctctaact tgctgctgaa cctaacacat gcttaatccg tagcatcttt ttgaggatta   155100
aatgggatgg catatgtagt ccactttgta cagggcttgg cacctgggaa tgcaggtgct   155160
taatatagga ctgtttttat tactagcata aaatatctcc ttaaagggt cactataagg    155220 gtcagatgaa acctataagt gagcttgctt ttcaatctgt aaatctgaga atcactgtat   155280
aaatgttggt cataattatc atcatcacca ttaaattatt acaaggaact ggctaactgc   155340
cagcatgctc tactatgatc aatctatatt taggtcaatt aaaaatagat agatacagac   155400
ttctttgctt ttgttaggtt tacttaactt tagtcaactg tgaatgattg attataggct   155460
tgccattaca ttgttgcttc agagcttaga tgaaacactc atttgggtag tataaagaaa   155520
gcttagaact tgatgaggct atgacatctt ttattcattt acttttacct taaaaagttc   155580
tctattacaa aaatcaatat agtgtttgtt gttaaaataa attatagaga catgagtaaa   155640
gtgaaagaag agagttcacc cccttccttc ttttccatcc cattctttag aattaaccat   155700
attacaatgt aaccaattat tccttgtatg taaatatcat ttttatataa tgggatatac   155760
acatgtataa tatacatttt ctatttccaa atgaaaaaca aaatcttttt tttgcagaaa   155820
gttcaaagtt gttgaaaaga aaatcttttg caacagcttt tttgatttgt tcgtttccca   155880
atttaaaatg tctcctgggc atcttttccat gtaaatacat attcatcaat cccatttaa   155940 aaaccatata cagagtcatt taaacatttt tactaattaa ttattggaaa attgtttgta   156000
aaataaagga gactgccctt aaaataaaat agcaacttag ctaggattaa attaggcaat   156060
tcagaaaaat gcttagcaaa tgtttggcag attgtaaatg attgataaat aaatattagc   156120
cattatgata ttgatgatag tgatgattaa agatgactac tctctaagc tcactctcaa     156180 taaatttctg ttgtcagaga ggtggtttat tttatttaat tgcccaatat gtacatttat   156240
atataatatt cccatttat attttcattt taaggacgta cttggctgtg ttatatggtg     156300
gaggtgggtg ccgtgttctg gaaggactgt cagactcaag ttggttctct tcaggatctg   156360
cccaacccat ggcgacctag tacagtgcca aaattgaaca aaaaaatac aatccatcca    156420 tctgtcagtt agtgaggcag caaagaaggt atttagcttc taggacattt aaaaacctaa   156480
gttaattcta tctaaaagaa agacatctgt ggggtgggac tcgcctcctc tgagcctttg   156540
agaccagtgg ggatttaaac aggtataaat aatgactctt gaatagccac cagacagcca   156600
gtggtgcaac ctactctagg gagatgagtc acaggctgag ccgtgggtag taagtcccta   156660
ggagaaggga agaggggtgt ctgggatccc aggaagagca ataaatgcag tctgtcagct   156720
ccgcagcaga ggaggggctg tgacagcagc cctcacccag aagggggtgaa tggtaaatct   156780 acctcaatag acagtggcct gtgcattgta aatctgatca tttgctgtg cccaaaacat     156840 cttaagtata attataccaa agcctgaaaa aagactggct aaagagaaaa ctaaaataga   156900
ttttttaaaa tgcaaacaca caattctgcc tacaaaaatg ttaagtgcca aggaaaatat   156960
tgttaaaatc caagaggacc tccttttccta agctgcagtg ttcaggaatt tatatgtata   157020
taaggttggt agtgaccatg gacaaatcat tgcctacacc tctgccagaa catctgtcat   157080
ttctcatgaa gccggaactt taaatgtcac aactagatca gaaataacat tgatatcaga   157140
```

```
accatcatgt actttttttc tgctctgcat gtgagcatct ggggtgccta aaatccaacc  157200
ctcacagctc ttgaaaagtc ctgtgtcttg cagaagggat gcctttcagt gatgcatccg  157260
tgaggaggcg gcgccttttg ataattcaca caaaggtctt gctagtagag ggaggcctta  157320
ccttgactgg aggagagacc tacgtttgga tctcggctaa agtatcttcc aagagcaaca  157380
ttcttgttag cataacatgc cattttcatg tcctacagat tcatagattt atggagtttt  157440
gaactagtta aatgccttag aaatgaccaa tacccaccca ttttgttgat aagggacctg  157500
aagcatagag aagtcagata gtttgaatat ttgtccctac ccaaatctca tgttgaattg  157560
taatctccag tgttagaggt ggagcctggt gggaggtgtt tggatcatgg gggcaaattc  157620
ctcatgaatg gcttgggcca tccccttggt gataagtgag ctctgagtta acactgagat  157680
cacatagttt aaaagtgtgt ggcacctccc tcacacctca actctctttc ttttgcttct  157740
gtttttgcct catgatgtgc ctactctccc ttgac                             157775
```